US011530411B2

(12) United States Patent
Zhao et al.

(10) Patent No.: US 11,530,411 B2
(45) Date of Patent: Dec. 20, 2022

(54) METHODS FOR REDUCING LRRK2 EXPRESSION

(71) Applicant: Ionis Pharmaceuticals, Inc., Carlsbad, CA (US)

(72) Inventors: Hien Thuy Zhao, San Diego, CA (US); Holly Kordasiewicz, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/125,738

(22) Filed: Dec. 17, 2020

(65) Prior Publication Data

US 2021/0340546 A1    Nov. 4, 2021

Related U.S. Application Data

(63) Continuation of application No. 16/063,903, filed as application No. PCT/US2017/012374 on Jan. 5, 2017, now Pat. No. 10,907,160.

(60) Provisional application No. 62/424,346, filed on Nov. 18, 2016, provisional application No. 62/275,121, filed on Jan. 5, 2016.

(51) Int. Cl.
| | |
|---|---|
| *C12N 15/113* | (2010.01) |
| *A61P 25/16* | (2006.01) |
| *A61K 31/712* | (2006.01) |
| *A61K 31/7125* | (2006.01) |
| *A61K 31/7115* | (2006.01) |
| *C12N 9/12* | (2006.01) |
| *C12Q 1/68* | (2018.01) |

(52) U.S. Cl.
CPC ........ *C12N 15/1137* (2013.01); *A61K 31/712* (2013.01); *A61K 31/7115* (2013.01); *A61K 31/7125* (2013.01); *A61P 25/16* (2018.01); *C12N 9/12* (2013.01); *C12N 2310/11* (2013.01); *C12N 2310/315* (2013.01); *C12N 2310/3231* (2013.01); *C12N 2310/3341* (2013.01); *C12N 2310/341* (2013.01); *C12N 2310/346* (2013.01); *C12Y 207/11001* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |

(Continued)

FOREIGN PATENT DOCUMENTS

| | | |
|---|---|---|
| WO | WO 2004/094636 | 11/2004 |
| WO | WO 2006/045392 | 5/2006 |

(Continued)

OTHER PUBLICATIONS

Alegre-Abarrategui et al., LRRK2 regulates autophagic activity and localizes to specific membrane microdomains in a novel human genomic reporter cellular model: Hum Mol Genet (2009) 18(21): 4022-4034.

(Continued)

*Primary Examiner* — Sean McGarry
(74) *Attorney, Agent, or Firm* — McNeill Baur PLLC

(57) ABSTRACT

Provided herein are methods for decreasing LRRK2 mRNA expression. Such methods are useful to ameliorate LRRK2 associated diseases. Such LRRK2 associated diseases include Parkinson's Disease, including non-LRRK2 mediated Parkinson's Disease.

25 Claims, No Drawings

Specification includes a Sequence Listing.

(56) References Cited

U.S. PATENT DOCUMENTS

| | | |
|---|---|---|
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,029,986 B2 | 10/2011 | Meitinger et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,187,811 B2 | 5/2012 | Ericksson et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,669,048 B2 | 3/2014 | Reijo Pera et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,840,710 B2 | 12/2017 | Hastings et al. |
| 10,907,160 B2 | 2/2021 | Zhao et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2012/0135941 A1 | 5/2012 | Collard et al. |
| 2013/0130378 A1 | 5/2013 | Manoharan et al. |
| 2014/0107330 A1 | 4/2014 | Freier et al. |

(56) References Cited

U.S. PATENT DOCUMENTS

| | | |
|---|---|---|
| 2014/0128322 A1 | 5/2014 | Chen et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2012/0052487 A9 | 11/2015 | Khvorova et al. |
| 2017/0137826 A1 | 5/2017 | Hastings et al. |
| 2018/0362988 A1 | 12/2018 | Zhao et al. |

FOREIGN PATENT DOCUMENTS

| | | |
|---|---|---|
| WO | WO 2007/124096 | 11/2007 |
| WO | WO 2008/091799 | 7/2008 |
| WO | WO 2009/099991 | 8/2009 |
| WO | WO 2011/114106 | 9/2011 |
| WO | WO 2013/173635 | 11/2013 |
| WO | WO 2016/097212 | 6/2016 |
| WO | WO 2012/131365 | 3/2017 |
| WO | WO 2017/087282 | 5/2017 |
| WO | WO 2017/120365 | 7/2017 |
| WO | WO 2019/118325 | 6/2019 |
| WO | WO 2020/006267 | 1/2020 |

OTHER PUBLICATIONS

Atashrazm et al. "LRRK2 Inhibitors and Their Potential in the Treatment of Parkinson's Disease: Current Perspectives" Clin Pharmacol (2016) 177-189.
Bieri et al., "LRRK2 modifies α-syn pathology and spread in mouse models and human neurons" Gitler Lab (2019) 1-41.
Branch et al., "A good antisense molecule is hard to find," TIBS (1998) 23:45-50.
Chan et al., "Rael protein rescues neurite retraction caused by G2019S leucine-rich repeat kinase 2 (LRRK2)." J Biol Chem (2011) 286(18):16104-9.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cho et al., "Leucine-rich repeat kinase 2 regulates Sec16A at ER exit sites to allow ER-Golgi export" EMBO J (2014) 33:2314-2331.
Cole et al., "Antisense Oligonucleotide Therapeutics for the Treatment of Neurodegenerative Diseases" Presentation for Genetic Epidemiology of Parkinson's Disease (GEO-PD) (Sep. 12, 2014).
Crooke et al., "Basic Principles of Antisense Therapeutics" Antisense Research and Application (1998) Chapter 1:1-50.
Crooke, St., et al., "Antisense Drug Technology" Second Edition, CRC Press (2008) Chapters 1-28.
Daher et al., "Abrogation of α-synuclein-mediated dopaminergic neurodegeneration in LRRK2-deficient rats" PNAS (2014) 111: 9289-9294.
Daher et al., "Leucine-rich Repeat Kinase 2 (LRRK2) Pharmacological Inhibition Abates α-synuclein Gene-induced Neurodegeneration" J Biol Chem (2015) 290: 19433-19444.
Daher et al., "Neurodegenerative phenotypes in an A53T α-synuclein transgenic mouse model are independent of LRRK2" Hum Mol Genet (2012) 21: 2420-2431.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Genbank Acc. No. NM_198578.3.
Genbank Acc. No. NT_029419.11.
Gautschi et al., "Activity of a novel bcl-2/bcl-xLbispecific antisense oligonucleotide against tumors of diverse histologic origins" J. Natl. Cancer Inst. (2001) 93:463-471.
Guerreiro et al., "LRRK2 interactions with α-synuclein in Parkingson's disease brains and in cell models" J Mol Med (2013) 91: 513-522.
Henderson et al., "LRRK2 activity does not dramatically alter α-synuclein pathology in primary neurons" Acta Neuropathologica Comm (2018) 6: 1-11.
Herzig et al., "LRRK2 protein levels are determined by kinase function and are crucial for kidney and lung homeostasis in mice" Human Mol Gen (2011) 20(21): 4209-4223.
Herzig et al., "High LRRK2 Levels Fail to Induce or Exacerbate Neuronal Alpha-Synucleinopathy in Mouse Brain" PLoS One (2012) 7(5): 1-14.
Hinkle et al., "LRRK2 knockout mice have an intact dopaminergic system but display alterations in exploratory and motor co-ordination behaviors" Mol Neurodegener (2012) 7: 1-17.
Hirst "LRRK2 ASO: Path to the Clinic" Abstract for Michael J Fox LRRK2 Summit (Mar. 25-26, 2019).
International Search Report for PCT/US17/12374 dated Mar. 23, 2017.
International Search Report for PCT/US19/39558 dated Nov. 14, 2019.
Lin et al., "Leucine-rich repeat kinase 2 regulates the progression of neuropathology induced by Parkinson's-disease-related mutant alpha-synuclein" Neuron (2009) 64: 807-827.
Lloret et al., "Validation of LRRK2 as a Drug Target for Treatment of Parkinson's Disease Using Antisense Technology" Michael J. Fox Foundation Funded Grant Interim Progress Report, (2009) retreived from the internet on Sep. 11, 2018 (https://www.michaeljfox.org/foundation/grant-detail.php?grant id=542).
Luk et al., "Pathological α-synuclein transmission initiates Parkinson-like neurodegeneration in nontiansgenic mice" Science (2012) 338(6109): 949-953.
Maher et al., "Comparative hybrid arrest by tandem antisense oligodeoxy ribonucleotides or oligodeoxyribonucleoside methylpbosphonates in a cell-free system" Nucl. Acid. Res. (1998) 16(8):3341-3358.
New England Biolabs 1998/99 Catalog (cover page and pp. 121 and 284).
Nichols et al., "Substiate specificity and inhibitors of LRRK2, a protein kinase mutated in Parkinson's disease." Biochem J. (2009) 424(1):47-60.
O'Hara et al., "LRRK2 and α-Synuclein: Distinct or Synergistic Players in Parkinson's Disease?" Frontiers in Neuroscience (2020) 14: 1-18.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Sheng et al., "Deletion of the WD40 Domain of LRRK2 in Zebrafish Causes Parkinsonism-Like Loss of Neurons and Locomotive Defect" PloS Genetics (2010) 6(4):e1000914.
Sibley et al., "Identification of allele-specific RNAi effectors targeting genetic forms of Parkinson's disease" PLoS One (2011) 6(10): e26194.
Sibley et al., "Silencing of Parkinson's disease-associated genes with artificial million mimics of miR-1224" Nucleic Acids Res. (2012) 40(19): 9863-9875.
Swayze "This Is Your Brain on Antisense Oligonucleotides: Distribution, Activity and Application to the Treatment of Severe Neurodegenerative Disease" Abstract for 253rd Meeting of the American Chemical Society (Apr. 2-6, 2017).
Swayze "This Is Your Brain on Antisense Oligonucleotides: Distribution, Activity and Application to the Treatment of Severe Neurodegenerative Disease" Presentation for 253rd Meeting of the American Chemical Society (Apr. 2, 2017).
Tatarnikov et al., "Neurotransmission in LRRK2 and VPS35 mutant mice—rescued by acute LRRK2 knock-down" Presentation for Society for Neuroscience Annual Meeting (Sep. 15, 2016).
Tong et al., "Loss of leucine-rich repeat kinase 2 causes age-dependent bi-phasic alterations of the autophagy pathway" Mol Neurodegener (2012) 7: 1-16.

(56) References Cited

OTHER PUBLICATIONS

Tran et al., "Antisense oligonucleotides to LRRK2 ameliorate alpha-synuclein pathology and behavioral deficit induced by pre-formed alpha-synuclein fibrils." Abstract from Society for Neuroscience meeting Nov. 15, 2016, retreived from the internet Aug. 15, 2018 http://www.abstractsonline.com/pp8/index.html#!/4071/presentation/14652/.

Volpicelli-Daley et al., "LRRK2 Expression Augments α-Synuclein Sequestration into Inclusions in Neurons" J Neuroscience (2016) 36(28):7415-7427.

Volpicelli-Daley et al., "LRRK2 facilitates formation of alph-synuclein inclusions." abstract from Society for Neuroscience meeting, Nov. 15, 2016, retreived online Aug. 21, 2018 http://www.abstractsonline.com/pp8/index.html#!/4071/presentation/14651.

Volta et al., "Chronic and acute LRRK2 silencing has no long-term behavioral effects, whereas wild-type and mutant LRRK2 overexpression induce motor and cognitive deficits and altered regulation of dopamine release." Parkinsonism anRelat Disord (2015) 21(10):1156-63.

Woolf et al., "Specificity of antisense oligonucleotides in vivo" PNAS (1992) 89: 7305-7309.

Ynigo-Mojado et al., "Efficient allele-specific targeting of LRRK2 R1441 mutations mediated by RNAi" PLoS One (2011) 6: e21352.

Zhao et al., "Antisense oligonucleotides to LRRK2 ameliorate alpha-synuclein pathology and behavioral deficit induced by pre-formed alpha-sunuclein fibrils" Abstract from American Acadamy of Neurology meeting, Oct. 16, 2012, retreived from the internet Aug. 15, 2018: http://www.abstractsonline.com/pp8/#!/4046/presentation/8588.

Zhao et al., "Antisense oligonucleotides to LRRK2 ameliorate alpha-synuclein pathology and behavioral deficit induced by pre-formed alpha-synuclein fibrils" Presentation for Society for Neuroscience Annual Meeting (Sep. 15, 2016).

Zhao "Inhibitors of Leucine-rich Repeat Kinase 2 (LRRK2): Progress & Promise for the Treatment of Parkinson's Disease" Presentation for World CNS Summit (Feb. 20, 2017).

Zhao et al., "Antisense Oligonucleotides to LRRK2 Ameliorate alpha-Synuclein Pathology and Behavioral Deficit Induced by Pre-Formed alpha-Synuclein Fibrils." Annals of Neurology (2017) 82(21):S56-S57.

Zhao et al., "Antisense Oligonucleotides to LRRK2 Ameliorate alpha-Synuclein Pathology and Behavioral Deficit Induced by Pre-Formed alpha-Synuclein Fibrils." 13th International Conference on Alzheimer's and Parkinson's diseases, abstract presented Apr. 1, 2017.

Zhao et al., "LRRK2 Antisense Oligonucleotides Ameliorate α-Synuclein Inclusion Formation in a Parkinson's Disease Mouse Model" Mol Ther Nucleic Acids (2017) 8:508-519.

Zhao et al., "LRRK2 Antisense Oligonucleotides Ameliorate α-Synuclein Inclusion Formation in a Parkinson's Disease Mouse Model" Abstract for 142nd Annual Meeting of the American Neurological Association (Oct. 15-17, 2017).

Zhao et al., "LRRK2 Antisense Oligonucleotides Ameliorate α-Synuclein Inclusion Formation in a Parkinson's Disease Mouse Model" Poster for 142nd Annual Meeting of the American Neurological Association (Oct. 15-17, 2017).

SEQUENCE LISTING

```
<160> NUMBER OF SEQ ID NOS: 18

<210> SEQ ID NO 1
<211> LENGTH: 8231
<212> TYPE: DNA
<213> ORGANISM: Mus musculus

<400> SEQUENCE: 1
gagcagctct gagagcagga gccgtcccag ctcgccgcag tccccgccgg ctgcaccatg      60
gccagtggcg cctgtcaggg ctgcgaagag gaagaggagg aggaggctct gaagaagttg     120
atagtcaggc tgaataatgt ccaggaaggc aagcagatcg agacgttgct tcagctcctg     180
gaggacatgc tggtgttcac ctactcggac cgcgcctcca agttatttga agataaaaat     240
ttccacgtgc ctctgttgat tgtcctggac tcctacatga gagttgccag tgtacagcag     300
gcggggtggt cacttctgtg caaattaata gaagtctgtc cagggacatt gcaaagctta     360
ataggacccc aggatattgg aaatgattgg gaagtccttg gtattcaccg gctgattctt     420
aaaatgttaa ctgttcatca cgccaatgta aacctgtcaa tagttggact aaaagccttg     480
gatctcctcc tagattcagg taaactcacc ttgctgatac tggatgaaga atgtgatatt     540
ttcttgttaa tttttgatgc catgcacaga tattcagcca atgatgaagt ccaaaaactg     600
ggatgcaaag ctttacacgt gctttttgag agagtttccg aggaacagct gactgagttt     660
gtggagaaca aagattacac gatactgctg agtacgttcg gcagcttcag aagggacaag     720
gagattgtgt accacgtact ttgctgcttg cattccctgg cggttacatg cagcaatgta     780
gaggtcctca tgagtgggaa tgtccggtgc tacaatcttg tggtggaggc catgaaagcc     840
ttccccacca atgaaaacat ccaagaggtg agctgctcct tgttccagaa gcttacatta     900 ggtaacttt tcaacatcct ggtgttgaac gaagtgcatg tctttgtggt gaaagcggtc     960
cgacagtatc ctgagaacgc agccttacag atctctgcac tcagctgttt agcactcctc    1020
actgagacta ttttcttaaa ccaagacttg gaggaaagaa gtgagactca agagcagagc    1080
gaagaggaag acagtgagaa gcttttctgg ctggaacct gctataaagc cctggtgcgc    1140
catcgaaagg acaaacacgt gcaggaggct gcctgctggg cactaaataa cctccttatg    1200
taccagaaca gtttgcatga gaagatcgga gatgaagatg gccagttccc tgcgcacagg    1260
gaagtgatgc tgtctatgct gatgcactct tcttccaaag atgtcttcca agcagctgca    1320
```

```
catgctctgt ccactctctt ggaacaaaat gttaatttca ggaaaatcct gctggcaaaa      1380
ggagtatacc tgaatgtctt ggaattgatg cagaagcatg cccatgcgcc tgaggtggca      1440
gagagtggct gcaagatgct gagtcacctg tttgaaggaa gtaacccttc tctggataca      1500
atggcagcag tggtccctaa aatactaaca gtgatgaaag cccacggaac gtctctgtca      1560
gtccagctgg aggcgctgcg agctatcttg catttcgttg tgccaggact attggaagaa      1620
tccagggagg actctcaatg cagaccaaat gtgctcagaa acagtgtttt caggactgac      1680
atccacaagc tggttctagt cgctctgaac aggttcattg ggaatcctgg gattcagaaa      1740
tgtggattga agtaatctc ttctctcgcg caccttcctg atgccacaga gacattgtcc        1800
ctgcaaggag cagttgactc agtcctccac accttacaga tgtatccaga tgaccaagaa      1860
attcagtgtc tgggcttaca ccttatggga tgcttgatga caaagaagaa tttctgcata      1920
gggacagggc acctcctggc aaaaattctg gcttccactt tgcagcgctt taaagatgtt      1980
gctgaggtgc agactacagg attacagaca ccctgtcaa tacttgagct gtcagtatct       2040
ttctccaagc tgctagtgca ctattccttt gatgtggtga tatttcatca gatgtcttcc      2100
agtgttgtag aacaaaagga tgagcagttc ctcaatctat gttgcaaatg ctttgcaaaa      2160
gtggccgtga tgatgagct gaaaaacacc atgctagaga gagcctgcga tcagaataac        2220
agcatcatgg ttgaatgttt gctcctcttg ggagctgatg ccaaccaagt gaaggggca        2280 acttctttaa tctatcaggt atgtgagaaa gagagcagtc ctaaattggt ggaactgttg      2340
cttaatggtg ttgtcgtga acaagatgta cggaaggccc tgaccgtaag catccaaaag        2400
ggcgacagcc aggtcatcag cttgctcctc aggaaacttg ccctggacct ggccaacaac      2460
agcatttgcc ttggaggatt tggcatagga aaaattgatc cttcttggct tggtccttta      2520
tttccagata agtcatccaa tttaaggaag caaacaaaca caggatctgt cctagcgagg      2580
aaagtgctcc ggtatcagat gagaaacacc cttcaagaag gcgtggcctc aggcagtgac      2640
ggcaagtttt ctgaagacgc gctggcgaaa tttggagaat ggacctttat tcccgactct      2700
tctatggaca gtgtgtttgg ccagagcgat gatctggata gcgaaggcag cgagagctca      2760
tttctcgtga agaggaagtc caactcaatt agtgtagggg aagtttacag agatctagct      2820
ctgcagcgct gctcaccaaa tgctcagagg cattccaatt cgctgggtcc tgtttttgac      2880
catgaagact tactgagacg aaaaagaaaa atactgtctt cagatgagtc tctcaggtcc      2940
tcaaggctgc cgtcccatat gaggcaatca gatagctctt cttccctggc ttctgagaga      3000
gaacacatca cgtcgttaga cctatctgcc aacgaactca agatattga tgctctgagc        3060 cagaagtgtt gcctcagtag ccacctggaa catctcacca aactggaact tcaccagaat      3120
tcactcacga gcttcccaca gcagctgtgt gagactctga agtgtttgat acacttggat      3180
ttgcacagta acaaattcac ctcatttccc tctttcgtgt tgaaaatgcc acgtatcacc      3240
aacctagatg cctctcgaaa tgacatcggg ccaacagtag ttttagaccc tgcgatgaag      3300
tgtccaagcc tcaaacagtt gaatctgtcc tataaccagc tctcttcaat cccagagaat      3360
cttgcccaag tggtggagaa acttgagcag ctcctactgg aaggaaataa aatatccggg      3420
atttgctctc ccctgagcct gaaggaactg aagattttaa atcttagtaa aaatcacatt      3480
ccatccctac ctggagattt tcttgagct tgttcaaaag tcgagagttt cagtgctcgc       3540
atgaattttc ttgctgcaat gcctgcctta ccttcttcca taacgagctt aaaattgtct      3600
cagaactctt tcacgtgcat tccagaagcg attttcagtc ttccgcactt gcggtccttg      3660
gatatgagcc acaacaacat tgaatgtctg ccgggacctg cacattggaa gtctctgaac      3720
```

```
ttaagggaac tcattttttag caagaatcag atcagcacct tagactttag tgagaaccca    3780
cacgtgtggt caagagtaga gaaactgcat ctctctcata ataaactgaa agagattcct    3840
ccagaaattg gctgccttga aaatctgacg tctctcgacg tcagttacaa cttggaactg    3900
aggtccttcc caaatgaaat gggggaagttg agcaagatat gggatcttcc cttggacgga   3960
ctgcatctga attttgactt taagcacgta ggatgcaagg ccaaagacat cataaggttt    4020
ctacaacaac gtctgaaaaa ggctgtaccc tacaaccgaa tgaagctcat gattgtggga    4080
aatacgggga gcggtaagac cactttactg caacaactca tgaaaatgaa gaaaccagaa    4140
cttggcatgc agggtgccac agtcggcata gacgtgcgag actggtccat ccaaatacgg    4200
ggcaaaagga gaaaggacct ggttctaaac gtgtgggatt ttgcaggtcg tgaggaattc    4260
tacagcactc accccccactt catgacccag agagccctct acctggctgt ctatgatctc   4320
agcaagggggc aggcagaggt ggacgccatg aagccctggc tcttcaatat caaggctcgt   4380
gcctcttctt ccccgtggat tctggtgggc acacatttgg atgttctga tgagaagcag    4440
cggaaagcgt gcataagcaa aatcacgaag gaactcctaa ataagcgagg attccccacc    4500
atccgggact accactttgt gaatgccacc ggaggagtcag atgcgctggc aaagcttcgg   4560
aaaaccatca taaatgagag ccttaatttc aagatccgag atcagcctgt ggttgggcag   4620
ctaattccag attgctacgt agaactggag aaaatcattt tatcagagcg gaaagctgtg   4680
ccgactgagt ttcctgtgat taaccggaaa cacctgttac agctcgtgaa cgaacatcag   4740
ctgcagctgg atgagaacga gctcccacac gccgttcact tcctaaatga gtcgggagtt   4800
cttctgcatt ttcaagaccc tgccctgcag ctaagtgacc tgtactttgt ggaacccaag   4860
tggctttgta aagtcatggc acagatcttg acagtgaagg tagacggctg tctgaaacat   4920
cctaagggca tcattttcccg gagagatgtg gaaaaattcc tttcaaagaa gaagcgattc   4980
ccgaagaact atatgatgca atactttaaa ctattagaaa aatttcagat cgcattgcca   5040
ataggggaag aatatcttct ggttccaagc agcttgtctg accacaggcc agtgatagag   5100
ctcccccact gtgagaactc tgagatcatc atccggctgt acgaaatgcc gtactttccc   5160
atgggatttt ggtcaagatt gattaaccga ttacttgaaa tctcaccctt catgctttct   5220
ggcagagaga gagcactacg ccctaacagg atgtattggc ggcaaggcat ctacttgaat   5280
tggtctccag aagcatactg tctggtaggc tctgaagtct tagacaatcg acctgagagt   5340
ttcttgaaaa tcacagttcc gtcttgtaga aaaggttgta ttcttctggg ccgagttgtg   5400
gatcatattg actcactcat ggaagaatgg tttcccgggt tactggagat tgacatttgt   5460
ggggaaggag aaactctgtt gaagaaatgg gcattgtaca gttttaatga tggtgaagaa   5520
catcagaaga tcttgcttga tgagttgatg aagaaggctg aagaaggaga cctgttaata   5580
aatccagacc aaccaaggct cactattcca atatcccaga ttgctccgga cttgatcttg   5640
gctgacctgc ctagaaatat catgttgaac aatgatgagt tggaatttga ggaagcacca   5700
gagtttctct aggcgatgg aagttttgga tccgtttatc gagctgccta cgaaggagag    5760
gaagtggctg tgaagatttt taataagcac acatctctta ggctgttaag acaagagttg   5820
gtggtccttt gtcaccttca ccaccccagc ctgatatcct tgctgcggc tggtattcgt    5880
cctcggatgt tggtaatgga gttggcctcc aaaggttcct tggatcgcct gctgcagcag   5940
gacaaagcca gcctcaccag aaccctccag cacaggatcg cgttgcatgt ggccgacggc   6000
ctgaggtatc tccactcagc catgattatt taccgtgacc tgaagcccca caatgtgctg   6060
```

```
ctttttaccc tgtatcccaa tgctgccatc attgcgaaga ttgcggacta cgggatcgca    6120
cagtactgct gcaggatggg aataaagaca tcagagggca ccccaggytt ccgggcacct    6180
gaagttgcca gggggaatgt catttataac caacaggccg atgtttattc ttttggctta    6240
ctacttcacg atatttggac aactgggagt aggattatgg aggtttgag gttcccaaat     6300 gagtttgatg agttagccat acaagggaag ttgccagatc cagttaaaga atatggctgt    6360
gccccatggc ctatggttga gaagttaatt acaaagtgtt tgaaagaaaa tcctcaagaa    6420
agacccactt ctgcccaggt cttgacatt ttgaattcgg ctgaattaat ttgcctcatg     6480
cgacacattt taatacctaa gaacatcatt gttgaatgca tggttgccac gaatctcaat    6540
agcaagagtg cgactctctg gttgggatgt gggaacacag aaaaaggaca gctttcctta    6600
tttgacttaa acacggaaag atacagctat gaggaagttg ctgatagtag aatactgtgc    6660
ttggctttgg tgcatctcgc tgctgagaaa gagagctggg ttgtgtgcgg acacagtct    6720 ggggctctcc tggtcatcaa tgttgaagag gagacaaaga gacacaccct ggaaaagatg    6780
actgattctg tcacttgttt gcattgcaat tcccttgcca agcagagcaa gcaaagtaac    6840
tttcttttgg tgggaactgc tgatggtaac ttaatgatat ttgaagataa agccgttaag    6900
tgtaaaggag ctgcccccctt gaagacacta cacataggcg atgtcagtac gccccctgatg   6960 tgcctgagcg agtccctgaa ttcatctgaa agacacatca catggggagg gtgtggcaca    7020
aaggtcttct cctttttccaa tgatttcacc attcagaaac tcatcgagac aaaaaccaac    7080
cagctgtttt cttacgcagc tttcagcgat tctaacatca tagcgctggc agtagacaca    7140
gccctgtata ttgccaagaa aaacagccct gtcgtagagg tgtgggacaa gaaaacagaa    7200
aagctctgtg aattaataga ctgtgtgcac ttcttaaagg aggtgatggt aaaactaaac    7260
aaggaatcga aacatcagct gtcctactct gggaggtga aggccctctg cctgcagaag    7320
aacacggctc tctggatcgg aactggagga ggccacatct tactcctgga tctttctact    7380
cggcgagtta tccgcaccat tcacaatttc tgtgattctg tgagagccat ggccacagca    7440
caattaggaa gccttaagaa tgtcatgctg gtttggggt acaagcggaa gagtacagag     7500
ggtatccaag aacaaaaaga gatacaatct tgtttgtcta tttgggacct caatcttcca    7560
cacgaggtgc aaaatttaga aaaacacatt gaagtaagaa cagaattagc tgataaaatg    7620
aggaaaacat ctgttgaata gaaagacatc aggcagtctc gatgttatat tgaataagac    7680
atcagacatc ctcgtcacta tattgaaaag gacatcagac atcctcgcca atatgttaga    7740
aaatgtactc ttcttttttaa aatatatttt taaaatgttt acattgaaaa gagtatgcct    7800
attctttaca aagttcatat gtatatgaag gaatgtgtat gtcttatgtt taatttaata    7860
tatgtaaaaa tatttatcag taaatatgtt ttaaaaaact attaatttta gcattatatt    7920
ttctatactc cttaactaat ttgaagggat aaacaaaga aatctacaaa gcatttaatt     7980
tcagtattta tactaaaatt aataaaaata tcatgtttgt tttgctatgt attgtgatga    8040
taaagcctat tttaaattgt tgattaagac acagatgttg cttgattatc tatggactca    8100
gcggagtaga ataaaatatc tggtcaattt ccaagtaaga gactctttca tatcttgttt    8160
tcaagtgaat tatcatcatt aatgtaaact gtcatatttt cactaataaa gattttgttt    8220
agctcaggaa a                                                        8231
```

<210> SEQ ID NO 2
<211> LENGTH: 150001
<212> TYPE: DNA
<213> ORGANISM: Homo sapines

<400> SEQUENCE: 2

```
gtacttttc cttcttcaga aattgataga gaaaggctac tacatactct gaatggatgt    60
caattggaca tccaaaagga caagatggca attctcccat cttgtccttc ttcaaaagtg   120
tctagtctat actaggcctt ttgatcttgc tgaaatctat gtaaatcttg ttgagaattt   180
cactaatctt gcattgtttt ttattacttt gtagagaatt gacatatttt tgaatttagt   240
tttcccatta attaatgtga tattaatatt tattcatgcc tttttaatgc cttttaacag   300
agttcaataa tttattcata aaggttttgt aaatatttgt taatttattt tcaaggtttc   360
cctttcattg tcatcataca cacacacaca cacaattgca ctttatgctt gtgcatcact   420
catgtttagg aacacatttt ttttataatg atgacattaa aaaatactta ttggtcattc   480
aaaatgaatt tccttttcaa aaccttagtt tattattttt tttcctggtc tatctgtggc   540
gtaataccct cctcccagtg atttgtaaga acttttgaaa gttgaaggca aattgtattt   600
catcatatgt atttcaaatt ttttcttcct gtttgccgtt tgacttctag tttcattatt   660
gggtatttt tctttgactg cagaaaattt aaatttgatg gagtcacata tactacccctt   720
atgtgatttc ttttttgttt ttatgttcc ttttttcaaga ttatataact attaattttat   780
attttatttt tgaagttatt tttatttaac tttttaatct atttgatgtt tgctgtaatt   840
agtaatgtca gttttatttt tttttctttc aggaaattag ccaaatgttc tagcaccatt   900
ttattctcca ctgaaccctg cttccatcat aaattcatgc cttaatcttc attttcagtc   960
ttgttaacta cttgaagagt tgataaatct tggaatttca gtcaatcaat taaacatttt  1020
tgaaaactaa gagaatactt taccttaaca ctgcagtagt tcatgggaga atgctcccaa  1080
caaataattc atatttttcac actgtctact cacagtctgg ccaatataga gtagataata  1140
aataggcaat agatggatga atgaattgtg gaaattagga gacatctttt aatttagatt  1200
tatttttctt tggaagggag gtaggtttta atttcttgca aggttgtaat tcagtagaac  1260
aggaagggag aaactaatgc agaggaacag aaggaatgca tgagatggag aatgcctaga  1320
aatgtttgag acattgatta agtcatcaga aatggaaaca agtttagaaa caacttagaa  1380
aataatacac tgtaggtctg ataaatattg taagattggg agttttttgt taaattatgg  1440
aaaatttttat atagatacaa tagtagaaca gaccacatga acccatctca tattatcttc  1500
aacaattatc aattcaaaag ttgttatcgt tatctctatc tccacacatt tcatcttttc  1560
ctccaccact ggatgacttt gaaagaaatc ctaaccattt caactataaa tattttagca  1620
tgtctctgta aaagttaaag actctataac aacaagacat agaccccaata tccaggttga  1680
gtaggagttt gctatcttac taatctaatg tattaacaaa gtctagagca ttcttattaa  1740
agtggtagag catgaagaac cttctacctg gagttaggag atttgctggg ttgaagtcct  1800
ggctctcaac ttcccaccctg tgtgactcca gcaaagctct tcacttctca attccaaatc  1860
tcaatttcct cactagtgaa agaaggatac atagtagtag ttgtatccat ttcagaattg  1920
tcatcaggat tgaagtaaca gatgtgaaaa caaaactaaa attgtgaagt agtaacttcc  1980
agtccaatcc tcttctttgt aagtgatctt gaggacagac acatcacctg aaggatagat  2040
catctttgcc tagccttgtc tacaatgttc ttgctaggtt tcttttccta aaaacacatt  2100
acttaggtac ttaacagaac aaacaaacaa acaatcaaaa gacaaaacca aaaaactttg  2160
gggttataga cacccatact cataagtatt tctgaatacc aagagaagag tatttaggtt  2220
tgcttctctc aacttttcac ctttcatttc atgtaccctg tcctttgtct cagctctaat  2280
```

```
agctctgaga gctgattact tttcgggtgt cccaagtatc aggatcctgc ctagtgcaac    2340
tcaaatttcc aaaagttaat ttagtggcct tttggtgacc agagcttcag ataactcaca    2400
gggaaacaat gtttatttcc tctcccacta acagtcacaa aaaatcataa aaagagtag    2460 cgggggcagt tttgatggct aacccctctt tccatccttt gggggaaaat tgctcatctc    2520
cctataggtg gaactctaaa gacaatgtat tcctaaaagg ggccatctgg gcggtgtcct    2580
cttttcccag cgccctgatt tctattctta gatctggaga taggcggctt tcattttttcc   2640 tgctcccagt tcccagacct tccgtggggc cgcaggatcc ccggctggcg ggtcgcggag    2700
ggtggccggc cgggctgcgc actgcgcgcc tccgctgcgg ggctccgggc ctgtggactc    2760
agcggagtcc gctgagtcag tttcttcccg cgcgactccc ggccgcgccg ccgctgcggt    2820
ggaatctggt cccaggaggc ggcgtccgcc cggggtccgg tctaggcgtg cgtgggggcc    2880
acggtcacgg tcatcccagc caggcccggc tccagcagcc ccacgccgc cgccagagtt     2940 ctgcgcggcc cgtcgcctcg gcggagcctc tggcaggccc ctgagctcgt ttttggggcc    3000
tgagtggggg aggaggaagc cgagcaggag ggctccggag agggagggca acgcggggcg    3060
gggagctgcc tccttcctca taaacaggcg ggcgtgggcg ccgatggggc ccgcggggag    3120
cgctggctgc gggcggtgag ctgagctcgc ccccggggag ctgtggccgg cgcccctgcc    3180
ggttccctga gcagcggacg ttcatgctgg gagggcggcg ggttggaagc aggtgccacc    3240
atggctagtg gcagctgtca gggggtgcgaa gaggacgagg aaaactctgaa gaagttgata   3300 gtcaggctga acaatgtcca ggaaggaaaa cagatagaaa cgctggtcca aatcctggag    3360
gatctgctgg tgttcacgta ctccgagcgc ggtaatcact tgaaaataaa ctgtgctttt    3420 attttttgcaa actttctccc cctccttaca tttgcaaatt ttgtcctcct cccccttgacc   3480 ctgctcaaac ccggactctt aaggagccgc aaactcccat atccttttcct tagggcagaa   3540 agcagctgag aatttcagga aggtcttcac ctttttgact tttctccccg tttcagacta    3600
aaaaggagag ggggtgctgt tggattgtgac tttgcttctt ttccccaccc acttgttttc    3660
cagcctccaa gttatttcaa ggcaaaaata tccatgtgcc tctgttgatc gtcttggact    3720
cctatatgag agtcgcgagt gtgcagcagg taaaggcatt gttttcactt caactcattc    3780
tcccttctgt ttggaaggag acgttttact ggcaatgtta atatagccga gagttcttgg    3840
ttattcccaa aatttggctt gaggaacctc tgactgtgat tttaagatgg gaatattgtt    3900
aaatcattac gcaatgtaaa cgggatgaag agccccagta tgtgttccct gagtgtcttt    3960
aagaagtaac tttataaaac caacagtatg gatggtggta gaaggaggat aaaaatgggt    4020
tcggttttag tctcgttatt ggcaagatga attcattagt gtttagactt gactattcca    4080
agtatcttcc caatacagag catgtcctag atgagaagat tatgaatagt ttggaaaagg    4140
ggaataatta atagtgataa aatgcaactt tgtcactagc aaactcttgt agagttcagc    4200 acttttttaaa attcaaagat ttctagcctt tagttgtagt taccttgta gtatctaaag   4260 aaagtgatgt cttatgagac cctcatagtt tgcaactgtt gtcatataaa atgcatgtag    4320
aagtgaaact tttacaatct gtaccatagg aaacccagaa atttgctatg tatcttggat    4380 tttttttaa aggggccttt aaaaatggta attaagaatg atttacagtc aaaacaaaat    4440
tataggccaa ggtgataact tccttcggag cacttagaga tttggggaac tgaaatcagt    4500
tttgtcatct gcatgttaac tcatgcagag aaagagaatt ggactttgaa ctccttggag    4560
gtgcagtcag aaagccaatg tttcttaatg gttgagaggc ttgacagaca tgaggcatct    4620
caatctttaa agtggtgtgg gtctatcttt atcttgatgt ttatctctgt atctagctgt    4680
```

```
atctagtctg ggtgaaccat ctagcttctt tgatatgagg acatttacat ctggaagaaa      4740
tattttaatt tgttttcaac tgtgaaatat tttccatctg actattatag attttcacgc      4800
tgctatcaaa ccaaaccaag aaaagatgga ggcataataa agatgctgtt cttttaagac      4860
tcaaagtcgg aattttgcct gtggaatatg agtcactttt tgggcactgg cctattgtgc      4920
ttcctgctct gcacccacgt catcccttct tacttgtctc tgctttggtg ttcagaagtg      4980
cctgattctg gccaccttca ttccctagac tctgtacttg atagagtcac tcctgcttga      5040
tactgctcag gacagtcaga tcctgggtag gcgttttggt ctgcagggtc tagataaggc      5100
agtgctatac ttgacaaccc aggggagcct ggaacatact tcctaattct taattttaga      5160
aattgcccaa gcctgagcat acttgtccgg agtagttatg agtgtcactt agtatttctg      5220
cctagagagt accagaggca aagtatgctg gaaaataagg aagagttttt ttaaaagtaa      5280
ttaattactt ttttggatat atcatagttg tatatatttt ggggatacat atgctatttg      5340
atacatgtat acaatgtgta atgttcaaat cagggtaact ggaatatccg tcacctcgaa      5400
cattttcctt tgtgttggca acgttgcaat ttctttcttc tagctatttt aaaatatgca      5460
atgaattatt aaccataatt tccctgctat actattaaat attaacttaa ttgcttgtat      5520
ctaattatat ttttgtacac attaaccacc ttctctttat ccctccccat cctttcattt      5580
ccagtctctg gtaaccacca ttctactctc ttcctccatg agatccacct tttccgctcc      5640
tacatatgag tgagattatg caatatttta tttctgtacc tggcttattt aatttaacct      5700
aatgacctcc agtcccaccc atgctgttgc aaatgacagg atttcatttt ttatgactga      5760
ataatattcc attgtgtatg tataccacat tttcttttat ttttagttaa gtaattaatt      5820
tagagacagg gtctcactct gttgcccaga ctggagagca gtggtgtgat caaagctcac      5880
tgcaggcctg caatcctggg ctgaagtagt cctcctgcct cagcctccca ggtagctagg      5940
actataagca tgtgccacca tgctcagcta attttttttt cttttttttac ttttgtaga      6000 gatggagtct tgctatgttg cccaggttag tttcaaactc ctgacctcaa gtaatcctcc      6060
tgcctcggcc tccatatttt ctttgttaat ctgttgatag acataaagg tgattctgta      6120 ttttaactat tgtgaacagg gctgcaataa acatgggagt tcagatatat ctttgatata      6180
ctgatgttct ttttttggat atatacccag cgatgagatt actggatcat atgaaaattc      6240 tcttttttagt ttttttaagat acctccatac tgtgtttcat catggctgtg ctactttata      6300
ttcccatcag cagtgtacca ccattccccct ttttctgcat ccttaccagc atttgttatt      6360
ttttgtcttt ttgataatag ccattctgcc tgtggtgaga taatatctca ttatggtttt      6420
gatttgcctc tccctaatga ttagtgaagt ttaggatttt tttttcatgt acctgttagc      6480
catttgtctg tcttcttttg agaaatgtct atttggatct tttgtccatt taaaaataag      6540 acttttttt tttttttttt ttttgctaat tgagttttt tagttcctta tgtattctgg       6600
ttgttaatct tttgttgaat ggatatttttg caaatattttt ctcccttttct ttatgttgtc     6660 tcttcacttt gttaattatt ttctttgttg tgcagaagct tttagcttg atataatccc      6720 atttgcctat ttttgttgta attgcctgtg cttttgaggt cctacccccaa aaatcattgc     6780 acagaccaat gtcctgtagc atttccccag tgttttcttc tagtagttgc atattttcag      6840
gtctgagatg taagtctttta atccatttttg aaatgatttg tgtatatggt gaaagctgtg      6900
gatctagttt ccttctttttg cacagccaat atttgattct cactgaaatc tcactgccct      6960
cctggaaata ttaccggatg ttttactgtc atagcgaagt gagagtaagc tgctcactga     7020
```

```
ggatcaaaga gcttgtgaca gacctaagac tcaagtcttc tcacaccttc aaaatctctt    7080
tccatcatac aatctactag ctgctgaatt cgcaagcttt ttgtgcaagc tagtaaaaag    7140
caaaatggtt tgatacaaat actgtggcca tgctaggtac aatgacatca atttaaatta    7200
tcattggtct taacaagggg atgtagaaag gggtctccta ctgacatttt aatactcact    7260
taaaagtagt attttttcctt cagatttctt tatattatta gtataattac tgtaagtatc    7320
ctttactgct ttatatgttg aattagctgg aagtgccaaa agaaaaactc ttaatgataa    7380
atttaaggta ttaaggtaaa tttctccttc atttaattta atagtaattc ttaattacta    7440
tttaaaataa agattaaggt ttgtttctag atgccattta acatgatatt ccagactgcc    7500
agttttattt tcaaagtttg tttcatattt tattaatgtt tcttcataaa tgacagtctt    7560
tagaaaattg acggttaagc taggtgcttt atattttttct tttcctgcct atcttttcac    7620
tgtgctccta aattttacat ctctttattc tcaagggttc aacctttgaa gaaggggagc    7680
aaaataaatg aaagtggcta aaattttttc tttaacccct agactctttc ctgttgtgca    7740
ttaattacat gcttgagttt ttagaataat tataataaag taaaactacc aatttaattg    7800
tattgtaact gtgcaagatg ggaaccttct ctcttagaga gataagcttt taattgaata    7860
gattaatgga tcaattgtta cctctgcttt gctgccagag attctattta atcacagaag    7920
ttccatgtag tgctggagag ctcagttgcc tgaatctttt tgcaaagcgt ttactgatac    7980
tgttgcttca ccaaccaaaa caaacaggtt ttttccttga gtcagctttg taggtacaga    8040
gatgagtttg gcatcctatg tgactttttt ttttttttttt tttttttttt ttaccaccag    8100
aagctgttca gaatgttatt tcttaaata gttcggaaaa aagtcttgat gtattctatg    8160
aaagcacaaa aatagtcagt ttctatgaca gctggattgt caacgtctgt tcagcttacg    8220
tggaggagga tgtcctactt gagtagtata ggtagaaata gctatcagaa attgccgcct    8280
ttgaaagcaa tttgaaatta tgtaaaagga agtaatgaca aaataaagca atttatgttt    8340
aatctggaaa agatccaaaa gtaatattgt aaagagatct tgagtaatca tttttatctt    8400
cctaaaatag ccgttgttta ctcccgtaag cgagtaagaa acttgtgcca ttattcctta    8460 tgggtgcat atagatttct caccttgtca ttcaactcct tgcaatattc aactttactt    8520
atgcatccag ccttatccca aaatagcctc ttccctgtag cagcttcctt atcatgtagc    8580
agcctactct cctcaccgct catccgttct tatacaatct ggcttaagct ctacctcttc    8640
atattatatt cttctctgag taatttcaac tcacactgag tcttactttc agtatttcta    8700
ttatattggt atttattaca catcacactt agatacttttt ccattagtct ctagagggta    8760
catatatgca cttttctcttt ttttttttttt ttttgaccat gtcaagtata gttctatagt    8820
ataatagaat gaattggaga tccttttacat ttagagaggg aggagtctac agtaggaaga    8880
ataggttaat tttcatctcc ggtttgaaat caggactttc aatttttttt tcagaggtaa    8940
agagcaactt agtcaagttg gcatcttgta aacagactga gtgaagatat acttaaaatg    9000
catctataat ttcatatttt atttcgaaat gtgaaagagc ctactagggg tgtctgtgat    9060
ctctagacct tatcaattca ttctagagaa atctggaggg agccattgag gagttctacc    9120
tcctgtctat tttatagagc tctttctctt tttctcctat cagatgtaga ttcaattgct    9180
aaaaatgcca cgtttcttgc ctctattatt ctagcttcat tacttgggga gcagccattc    9240
tgataactta cattttgcta ctaaaatctc caacttcacc taatccttca ttataagcca    9300
cttcattttt tcctataatt aaaattttaa atatgtggag gaaattctgt caggtagata    9360
tgacttaaaa cctactaagg gccaggtgca gaggctcacg cctgtaatcc cagcactttg    9420
```

```
agaggccaag tcaggaggat tgcttgagcc caggagcttg agaccagcct gggcaacaga    9480
gcgagacccc tgtcttcaca aaaaaaaaaa aaaaaaaatt agctgggtgt ggtggcacat    9540
acctgtagtc ccagctactt gggaggctga gtgggtgga tcacctaagg acaggagttc     9600
taggctgcag tgatctatga ttgcaccatt gcactccagc ctgggtgaca gagtgagacc    9660
ctatctcaaa aacaaaaaca aaccaaaaa aaaaaaaaa acaagaaaaa aaaagtacta      9720
aggatctggt atagccattc ttgcacttaa taatcttggt acaacctcta aaactatttt    9780
ttatagttta ttttattttg ccttatttag acaattggca tgtctatgtt cttcataatt    9840
tagaaattat atgtatttat atatataaat tatatatatt atatattatg tataaattaa    9900
attatatata tatataatat atatatattt gaaatggatt cttgctctgt catccaggct    9960
agagtgcagt ggcacaatct tggctcactg caccctctgc ctcctgggtt caagcgattc    10020
tccttcctca gcctcccgag tagctgagat tacaggcgcc catcaccatg cctggctaat    10080
ttttgtattt ttagtagaga ctgggtttca ccatcttggc cacattggtc tcaaactgcc    10140
ggctgaaatg ttgtatttt tgtatgtctt tctggtatga ttttggaga aaggtgtatc      10200 ctaagaatac ggcttgcttt tgtttctggg taagcatttt agggtatcat tttgttgtat    10260
aaccattgtt tacaagtgag ataagcatct attccactaa gattgaagag attcatgttt    10320
gactgagtat gctctattaa cattctttaa aacatgtgaa tatatgtctt tcttgttttc    10380
aggtgggttg gtcacttctg tgcaaattaa tagaagtctg tccaggtaca atgcaaagct    10440
taatgggacc ccaggatgtt ggaaatgatt gggaagtcct tggtgttcac cagtaagtat    10500
gatagatatg taaacaaat ggccttgagt atttatttgt acacatgaca accttccctt      10560
gatacactgt gtttgcaatc caaggctact cctgtggaat tctttaaaat acagatattt    10620
ttccttgagt caatgattta catttataga gagctttaaa ctcagaagtt tgatttagaa    10680
agcaaacatt taaggtaaca tgtcagaagt tattattta ataatataat catataatta     10740
taaaactggt taagttgtag attttgatg agtacttttg aattcaaacc atgaagagat     10800
tttggctttt aataatagaa tcgatacaaa ccactagttc ttaaaaaaat gggaactgag    10860
aaaagttagt tctgtaagta gtaatttgaa agttgatgtt ctactgtctt taaatagtac    10920
atttatatat atattcctat atatacagta agtttaaact atggctttca gaaagagtta    10980
agaaagagga aattaacttt cagcacatct gtagccaaat cttgatagta attttaccag    11040
ctatgttttt gcagtttgca gcataatggc ttcttagatg agactacttc cttagccatc    11100
attaattaag aaaatatttt ctcaagaaga atgtgtttcc aggaaaatac attttggata    11160
gctttgtttc ttgacagtta aaaaatatct tctaagctac tgaggaggct gaggaaggag    11220
aatcacttga acctgggagg cggaggttgc agtgagcgga ggttgcagtg agccgagatt    11280
gcaccactgc actccagcct gggtgacaga gcgacactct gtctcaaaaa caaacaaaca    11340
aacaaacctt ttgtcattaa ctttaaatct tttttatacc taatatgact tttcttatc     11400 acagaaaagg aaattgtgaa tatttttttgg cttccaatgg tatatggttt atgaaaattt   11460
aatttatgaa aaattttcag gtgtttgtat tgctgatcag tgtcaagtag tgctataaat    11520
ttagacaaat tagagctatg tgtttgtcca taagtgaaca tgtctgtgct tatacatttt    11580
cccctctttg acaaatgtgt tgctcttctt gttttcagta cataaagggt gtgttttgga    11640
aagagcatat ttacaattaa ttggagttct cgtcttcaat ctaatctctg taattctatg    11700
tatcagttct aaagtataca gcatttgatg aggaattact caaaatatac cagtaattag    11760
```

```
gaattgtaac tttaaatgtc ccttggtttg ggtgataatt tccaggaagt ccaaagatga    11820
gccagtctat aacctcaggg agtgtttggg aaactcatct agtcatattc ctgtacaaac    11880
caactgttca aattaaatta cataaaagtt tatgtaggaa atttcattca ctcactcact    11940
tactcattca ctcactttgt tcatccagtc attcatcttc tattcattga atgtttttga    12000
agcctgtcct ctgggtcaga aaccatgcag ttgtgaagaa gatagacaca ctgctgtctc    12060
cagtggagtg tattagatca ctcccagcaa aaattgattg taaaacagat ttctcttttt    12120
tcaaggcctt ttccctccaa agacttacca gtactgaaga aaaatttctt ccgtggtaat    12180
aaagtcagga attgtgggaa tggtataggg agaggtaggg gcagggtgat taggaggaag    12240
gctggcagag aatcgaagac tggcttcatt caggtcctcc aattgccaaa tggagattat    12300
gcaacgtttc ttgaatacat acaaaactct agatgtggcc agctcagtct tcttccaata    12360
atgtaaagcc aaacaatgct ttgcaggaat agactagaga ttatattttg ggattaataa    12420
catagggatt aaaatcttat cttgaactaa ctaaacatta ttgatatgct aaattcactt    12480
tttttttttt tttttttttt ttttttaga cagagtcttt ctctgttgcc aggctggcgt    12540
gcagtggcgt gatctcggct cactgtaacc tctgtgtccc gggttcaagt gattctcctg    12600
cctcagcctc tcgagtagct gggactgcag gagtacgcca ccacgcccag ctaattttg    12660 tatttttagt agagacaggg tttcatcatg ttggccagga tggtcttgat ctattgacct    12720
catgatcccc ccgcctcggc gtcccaaagt gctgagatta caggcgtgag caacggccac    12780
cggcccacta cttttaata tatcattaat ttctctttta aaaacagtag caatcaataa    12840
tttaaatatt caaatgaatt cttaatttat atacacaaac taacatcttt attatatctc    12900 tatatttaa tatatcaaca tgtctaagat aatttataaa tttacatcat atataaaaat    12960
gggtttgctc tcgatgtata taaggcttca tgatattttg aatatggagt tgggtgaaaa    13020
tagtgaatct gaatatttga atttgaatat ttattggaaa ataagtagtg cttttaactt    13080
tttaaatgag acacataata gtcccctgtt gattttttt tatttttta actttattaa    13140 agtatagttg acaattaaaa attgtttata tttaaggtat acaattgatg atttgacatg    13200
tgtacattgt gaattattca ccacaatcaa gctaattaac attccctgtt agttttata    13260 agcctggttc aggtttgtag aaagaaacaa acacacatgg ccaggcacgg tggctcacac    13320
ctataatccc agactttggg aggccaaggc aggaggatca cttgaaccca gaagtttaga    13380
ccagcctagg caaaatagca aaccctgtct ctccaaaaaa gaatgaaaaa attagcctgg    13440
tgtggtggca tgtacctgta tccctagcaa ctcaggaggc tgaggcagga ggattgctca    13500
cttgagccca ggagtttgag gtttcagtga gctatgattg caccattgca ttccagcctg    13560
ggtgacacag caagaccctg tctctaaaag caggcaacaa aaacacatga gcttcactac    13620
agggaattaa atacaatgag agtaataaaa aataggtgag caaaaaaaat gcaaataagc    13680
aaacttttga gtatgatatt tcattcttat cttgatttct gttttaact ccagattgat    13740 tcttaaaatg ctaacagttc ataatgccag tgtaaacttg tcagtgattg gactgaagac    13800
cttagatctc ctcctaactt caggtaatat gtgtatatgt tttttgtgtt gattcaaatt    13860
aaaaaaaaag ttgataccat taagtaaatg tgtgtgtgtg tgttttttt tttttttt    13920 tgaagatcag gattagggta gcttgattta aatgtcctaa aattgcatct gttttagac    13980 ctagtgatgg gacagccata atataatcta aatatcagtt atttccaaaa ttctttctgt    14040
ttccatctct tctccttatc tcttttctct atactttgcc tctcaaaaat ctcattcaat    14100
acattggttt taaacattac cttatatatt atccccaaat ctctgttggt agtccgatgt    14160
```

```
ttgctcccaa aatctggacc tacatctcat attcccccag gttagtggtc attcctgccc   14220
ttgccattat tacttctttc tccctatata tctttaataa attttctata atatatgttc   14280
tggagtatgc cataatcgtt acattttgaa aacacatagt attacttctt gagtatttgc   14340
tagatgccag gcttcacaag taaaatgctt cacgtgcttt taaacacctg aatctgaaaa   14400
cacccCttga gataggGatt ttatctcagt tttctaagtg acaaacactg aagtgcagag   14460
aagttgcttt ggccactaag aggtagaaac agggtctgat tctccatgtc aggttccttc   14520
cctgagaaaa ctttggcctg gtagataatg gacctgaaaa caaaaaatct tgaaatgatg   14580
caacagttgt gggcattgct gtgctggaca ctggctatta tataaggttc cgagaagaaa   14640
ggccgctcac agggagctaa tcttgaaggg ctgggaggag tttccttcca tgtaggggag   14700 ggcttttttag gttgagagaa gtatgggtgc agaggcctgg gaggatagca tgagagaggc   14760
tggacgtgtg attgggaagg tttgaattgt cctcatcagt cctgctaaga gatgtaaaga   14820
ccatgctgga gaaagaggaa gatgagagta tgagggaaaa acaagaaggt actcaacatt   14880
tcactacagc ttttatgac catgttgtat ggcatgcact aagagtcttt aaccatgatt   14940
taatttaacc tcaccCttgg gaggtatttt tttttttgacg gagattcatt ctccatttgg   15000
cgatggacag gaagatgagg gttattaat atgaaaaatc taccaacact ggaatatatt   15060
gaagttagcc tcatacagta ctactactcc tattccagta ttattatttt tattgacaga   15120
atagatgctg tttgtgttaa gtttttggatt atgataggaa atgtttggta tagtaaaagg   15180
caagagtgtg acatgcagtt agtccaagta cgaagagata ccaaaaaaaa aatgtttagt   15240
gaggagcaga gtttagcata tttggagtga agacaatgtg cggaaggaaa ggagctgatg   15300
agatacatgt actatagtcg gttgtgtgaa aggtcttgtt tttcatacta aggatcatga   15360
gaagatctta gtagattcca gcaagggatt tgcaagacca catttgtgtt ttagaaatat   15420
aatgcaggca ataaccagt tggatagaaa ttggggactg tagagcaatt aagcaactgt   15480
ttttgcattc tagatgagaa tgcaaaacac aataggaatg aaggtgcctt gttcaaaagg   15540 agtttttgttc aaaaggaatc ttcaagatgt gtaggagata ttcttaaagg acttggtaat   15600
gaattgattt gttgcttgga tagagaatga aagagaaag gagggtggaa gaaggaagat   15660
gacttaggag tttctcttgg gtagctagtg gattatggta tcattgatga agacagggaa   15720
caggagtagg ccaggtttgg ggtaactgtg gaatattcag atgttgtcta agaggcataa   15780 gaatgtatttt cagatgtttg gggcaagttg tctaggctag aagtactgat tgagactcat   15840
gaaattatag taaagtgaac tgggagttta tctcatttat aaagatctag agcttgataa   15900
gtctaacatc tagggcagtt aagtagttta tcaacaaaca aacaaacaaa caaacaagaa   15960
aaccatgggt ctacaaacca ttcacagtct tcatgtaaaa attaattcat gtaaaaatta   16020
acacattaaa tgttaaagca gctctttact cagagcatat tattctcttt aaaataggta   16080
aaatcacctt gctgatattg gatgaagaaa gtgatatttt catgttaatt tttgatgcca   16140
tgcactcatt tccagccaat gatgaagtcc agaaacttgg atgcaaagct ttacatgtgc   16200
tgtttgagag aggtattttta aaatgtcaaa ttccttaaag tatatataag aaaaaaaggc   16260
ttatactggg aaaagtagaa cacagttata ataagaagaa ggtttctaaa atcctactat   16320
ttattaagaa gtgggagttg tctgtcaagg gtgaggaatg gggttaattc agaagtattg   16380
cttgttttgg tggggtgaat ttcattcgtg ggttataaat catgcccctg gagtagactt   16440
tcttcaattg cttaacaagg cataaggttt actttgaaaa ctggatgtgt gggtgctatg   16500
```

```
aaagaaaaaa taaaactgtg aagccaagca taggttacac tgggattatg atgttgagtc    16560
atcaccagaa atcatagaaa ttgcataaag agcctgaagg tttacaaagt gtccttcagg    16620
aaaaagacta atatgcattt catagcctgg ccctgagatt gataactgag attattatgt    16680
aattttagag ttggttggag tccttgttta gtctttccat tgaccttagg aggaagtggg    16740
tcacagcagt gaagtgagca tcctgcctga ggacacagag cttgtgacag tacagttcaa    16800
ttagcaatta ttttaagagc ccctttttgta tcattatgag agccaactgt gctaggggtt   16860
tagataagaa tgatttatgt gggccctgtg tcagttatca gtttaccagt ctaatttctt    16920
gcagttccca gaatgggata gatcacctga taactgttga attccctgtc tcctcccaga    16980
aggattttaa acagcttata gataattata atacacaaga gtaaacaaaa tggatgagaa    17040
aataggtgaa gggacaataa tataaagcta gattaagttt actgtgtttc taaggtcctg    17100
catatttaca aaggggtggg ccagaaattt gtctgtttgc ttcctatctg acaaagaaaa    17160
gaggtaaata tcagtggtta caaagttcct taagataaaa gtaaacctat tattcaggag    17220
aagcaattgg tctcatggga gatctgagaa acatcttccc atgggttttc ctggatgaga    17280
caataaagga catacatttt gcaaggaata caaagtgtat tgcagcgaga gtgactctgt    17340
caaaagtcag aatagcatgg gcctggtacc cagctctttg ataatcatac accgtgaagt    17400
agaagatagt ttacagcgag tacggaattc cttcaggctg tcatgtataa atgttctatc    17460
ttgcaactaa gctttcgatg acaattagga taaagtttga ggttctattg tcttgcaggg    17520
tctgtaatct tctgtgtgga aggttagggg cacattcttc ttcctggaag gagggctagc    17580
atcactttat caccatcgtt gtttagtcca tctaagacac tggaggtaga ccatagaatg    17640
ttacaaagaa gaatgttgct caatagaaaa accatcagtg ctgagagggt tatgactata    17700
aatgtagagt agaaaaattt ctgatttttc caggagtatc aggttctcca ggactcaggg    17760
gtgactataa agttaatttt caaaatttga aagtgtactg tggaaactag accataaagt    17820
gagaaagttc catgatattc ttcacttgtt aggaaaactt aactgatttc acattatatt    17880
atagggacac tctggcataa aattaaaaaa aatgaatgtt gatcacttag agtgctgtgt    17940 tttctaaacat atttctggcg ccattctcaa gctagataaa ctataatttt atacatgttt    18000
ttcaggttgt tgcccaataa caatgactcc aaatggaact tactggcttg atcaaatgac    18060
tttaattgtg aaaattaatg atttatattt ttgctgtctg atggaaaacc actaagacag    18120
agtatttcaa agtctgatta cttgccattt gctcaagttg acaactcttg aactgaaaca    18180
tttagccgag ctgcccttca gcagcctacc attaatgcct ccctttttaaa tattgcaata   18240 tgtccagttc cagttggcca tctttattag tcactgtcag ttttctctag aatttcccaa    18300
atgaaattgt aaataatttt gttttttctga gaactgcttg ctgactagca cttttacatt   18360
tcaaaacatg gagtacctaa cataggccga aacaaaatta tttgaatctc cgtagcttgt    18420
tttctcatta taacattctt aggaagggct gcttcacaga aatatatttt ttatttaagg    18480
agattacact tgatgtatct cacacaacta taatgaatat tgtaatttttt gaataattaa    18540 actttcatat catctttaag cttattcagt attttgtctt tcatttttaa gtctcagagg    18600
agcaactgac tgaatttgtt gagaacaaag attatatgat attgttaagt gcgttaacaa    18660
attttaaaga tgaagaggaa attgtgcttc atgtgctgca ttgtttacat tccctagcga    18720
ttccttgtaa gtagcattta aatgttattt attttttgta tctgaaaaat tacaatatat    18780
ctcattctga gtatatttta acaatatttt tattatttag aaacttgtgg atgctcaacc    18840
cattcattca tttattcatt taattaattt acattcactg acattatact gaagttggct    18900
```

```
gtgggcttgg tgctggagaa acaatcgtgg aaaatacaga tgtgttcctt acctttttcag   18960 agcttgtagt acaatggggg acacagataa gtacagaggt gattacagtg gcagaagtga   19020
tggcagatgg cagaagtacc tagagttagg agatcaaata ggaagtgagg cagtgtctct   19080
tagcaaagat ttaataagtg gagcttcctg tgcatgaagg tgtgacctga agtgagaatg   19140
caggcaaagt ggcccaggca gtgggcatgg ttaatgtaaa gatgctggag caagagagag   19200
cagactgcct tcaagaagac aaaagtagct cagtaaaggt gtggggttat gagtgtgcgt   19260
gcatgcatgc gtgtgtgccg ctgtgcatgc acatccccaa atatcctatc cgtttgtgtt   19320
tcattgacag aggcaaggga gagcttgata agaggcagta atgaggcca gagacatgga   19380 gtggagagca tgaagggcct aaaaagccac atgaaggagt ttgaatttta ttgtgactct   19440
tgattagcat tttaatgagg ctttgaaatt tagccacatt tttcaccaaa aatattaatc   19500
agaagaaatt aatttgatgt gtatgctacc aatgattgct attaggctaa aataatggtt   19560
catattctgt tttgttttgt attaatggtt catattctgt tttgttttgt aagtgaccat   19620
taacactttg tattttatgt attacttgtg tgggtttcta caggatatac atatgcattt   19680
atctagtgat attttcatcc tcacacatgt gaagttttga ggattagagt taaacaatgt   19740
acctggtatg taataagtgt tctaaaatca ctgacaggat tattagacaa tatgtatttt   19800
atatgtgtgt tgtatactat atgtaattgc atttatggtt tcagatatgg aaatcactgt   19860
gtcaatctga aggtgtgagc cttcggtgta ggcagagtaa aacccaatgc ccttgtgaaa   19920
gaatgctttt ttttggtgat gtttataaaa tcacaatgtt ttcttatcca caggaaatta   19980
aacactggaa agtgggtggg gctgaacaat aatagagaaa ggccatggtt ttacatttct   20040
ctgagacatc actgccaaca aactgaatat gttttttcatt atactttttc cttggctata   20100
tttattcatt tatttatttta ttttgggctg gaggttttttg gaatccattg ttttccaccc   20160
acattggaca taactccagt aaaaatgtgt tgattcataa tgcaaaagtc aagaaagtag   20220
cagctaaaaa ttaagaaatc aaaagttttt aaaacactga ttctaactga aaacatttg   20280 cttttcagtc tttaagtcta ttgttctgag tcaaagcagt tcatttcctt acgttgttaa   20340 tttttttct atgtttaagc attgtaatat acttttttgtg aaaacagttg attagttttg   20400
gttgtgccaa aacaaatact aaaatgtttt gcaaacagcc tttttttaaa caaaaaaaga   20460
acagttaaca tttgatgcag agatatacat gttttctcca tgtaggttca cacctcactt   20520
cctttattga ttaattgctt tttctggtag agtctttctt tcctttctgt tttacctgtg   20580
tttgtcccta agacttatat tttaatatta tgcctcctct ctttcgttct cccatctttt   20640
cttccaccta ttttggagcc ttcaggaagc ttgattttgc tgccttgtac attggttgcc   20700
cttctggaat ggaggaaaca ggtcatagct gattttaact gttccatctg gtgacatatt   20760
cttgattttc tttcttttgg ttggggaaaa aaaaacaatg caaaagtcat tctccaatgg   20820
ggttgagcct cgttaagaaa tagaccctcc acaatggttg aactagttta cagtcccacc   20880
aacagtgtaa aagtgttcct atttctccac atcaaaaaaa aaaaaaggta agcaatataa   20940
catgagccat atctaatagg acttcagaaa ttatctatcc tatagttcca ggatgacgat   21000
gatgatggtt gtgataatga tgaagattgt gatgatagtt atatgggaga taaaacttta   21060
agcactttac atattaaatt ctataatatt caccacatct attaaaatat gttacattat   21120
tgtccctatt ttaccaacaa gaaaactgac caacaagatt aaacaacgtg actaagttca   21180
cacaacctgt aacagcagaa tctatgtcaa tcacaacaca attagcagct atttctgtgg   21240
```

```
caattttcaa taaagatgtg tctggaaaaa aaaaaaagaa atagaccctc caatttattt    21300
atctgaaaac ttatgaccaa tacattacat ttccagactt tcattttcag tacttttcct    21360
ttcattttca gtactaaaag tactctgaat ttttccttttt tttgatctta aggctttaag   21420
ccaagaaaca ggaataaagt aaattttcct taatgccaaa gattagtcct acaccccatt    21480
atgttattaa tgaacagcat agtattttttt acagctactt aaagaacatg atgtttaaat   21540
ttggaaatgc agtcattatg ctgccatcta tttacagtct atataagacg tctttgtatg    21600
catatttgaa aggagaacat ggttacctta ttgataatta tgatctcttt aaattcaggc    21660
aataatgtgg aagtcctcat gagtggcaat gtcaggtgtt ataatattgt ggtggaagct    21720
atgaaagcat tccctatgag tgaaagaatt caagaagtga gttgctgttt gctccatagg    21780
cttacattag gtgagtttct tagttaatat gtcatcacac actgtatgat atacatatac    21840
atataaaaca tatatatgtt gcataataat ggataagtag catattgaca tactttgaat    21900
gaaaatattg taaatcccca gaaaaaataa attaaaacaa aaagaaaata ctgtaaatta    21960
ccaaactgtt ctgctgtgct tagatggact tttaaaagga gtgtcaaaaa tagatgtgta    22020
gaatgtaaaa gaagtattat cttaatctta ttttttataga tgtagttcta tagatgagtt   22080
tttttattgt tgaggctata tttaaaatat aattatgtaa gaattgatac atacaaaaat    22140
atgcataaca tatacaatat aaagcataat gcaaataact cactatccaa cttaaatgtt    22200
gtatattccc agtgggggaa gctaccctgg gcttcttcct gcccttgctt tctctataga    22260
ggttaacact atccagaatt ttgtgtttac aaatcttttg tttataaata tgatttacta    22320
cattttcatg tttctctaag caaaattgtt aatgtttgcc tgcttttgct tcatcaaaat    22380
gtaatcatac tgtatgttgt cttctgcaat tttcaaatat cagtgctatg attataagaa    22440
tcagaaatat ttttgcatgt ggttgcatgt agtattctat tatttggaaa taccacaatt    22500 tattttttcca tttttctatc catggacatt tggattcttt cttatttat gctactacta    22560 tctgtgttaa aacagataac tgaaaaagaa cagttaacat ttggtgcaga gatatacata    22620
ttttctccat atataaataa gggttaatat tttaaaaaat atttatttgc cattggtatg    22680
tccttctttg tgaaatatgc aatctgtcat ttatcaaat tgttcacagg atagtctgtc     22740 ttttaaaac cgattcatag attctggata ataatgtttt ggtggtaggt tatacgtatt     22800
gaaaatacct tcccttgaac atcacactct ggggactgtt gtgggtggg gggagggggg    22860 agggatagca ttgggagata tacctaatgc tagatgacga gttagtgggt gcagcgcacc    22920
aacatggcac atgtatacat atgtaactaa cctgaacatt gtacacatgt acccataaaaac  22980 ttaaagtata ataataattt taaaaaaaag gagatgaaga ggtagctgca ggttgactga    23040
gcaagggtca ttgtctattt gaagtttcaa aggtatctct gaaataaaac acagttttt     23100 gcaagagtga aaaaaaaaaa aaaagaaaa taccttccct tgacttgtag catgtctttt    23160
caccgtcttt atggtggctt ttgtgatata gttaaattta ataatcagtt cctttgtgat    23220
ttactctttt ttatgtatct tgtttaagaa atcttaatct gtcctttccc taagataata    23280
aatatattgt atattttatt ccaaatctta ctcgtttgtt aaactgttgc agtttgtttt    23340
tgtaaagaac ccaattcccc ctctttttttt cagtgtggag agctagttac catcacagca    23400
caatttatta gaggttcacc tgtttcccag tcatgtggta tataaatatg taaacatata    23460
tgcttatgtt tctgtccttg gcgttctgtt gcattaatct gatttgtctg aatcagattt    23520
aaatctgatg ttaaatataa cactatttaa attaatagtt ctgtaagtcc tgatatctga    23580
aaagctaata ggtcaagtca ccatacattc ttttttaggc acagcttgcc ttttttcttg    23640
```

```
ggcctttact attccatgca aattacagga ttaacttgtc cagttccttg gaaaacactg   23700
ttgagatttt gactggaatt gcacaaaata tgtggatcat tttaagaaga actgacatct   23760
ttacattata atttcttcta tacatgtctt gcacatctta gttttttgcta cgtatcttat   23820 tttttattat tattgtaaat ggtatttctt tttaaatcat atttttgaac tgtgttttca   23880
taaagaaatg caaatgattt tttgtatatt gaactaacct acctttctaa actcttcgtt   23940
aattctgaca atttgtttct aaatgcactt aagttctcta cctagcaatt atataatttg   24000
taaataatga cagtctgagt tcttcctttc tgcttcttat attctttatt tcatttcctt   24060
gtcttcttac atgagtcaga attattaata tagtgttaaa tagagccatt gatactagac   24120
atccttgtct tgctcttttt cctgattta aacagaatat ttttaatatt ctcccatcca   24180
aaataatgca tcttacaagg gtttaaactt ttaaaaaaaa ttttgttaag aaattttatt   24240
ttatttcttc tttgcttttg ttttttcaat gtgggctttt aaatgtttgc ttttattttt   24300
acaatgtggg cttaaaaata ttaaaatatt taattttatc aaatatactt aaaatgtagt   24360 aagtctttt tttcctttc attatgttaa tatgaagaaa tacatctaca ggttttctaa   24420
tactaagcta ctgtgcactt cctgataaat ttaacttggt catttattag attttaaaa   24480 acacttctaa aaaatcttct ctgtttattt tcacatatac caggtgagtt ttggcagcct   24540 cttgttttt cttttttacc ctttcttttt tgttaaaaac atcctttat ttatttaatg   24600 attaatacat ggctattttg tgttttgtat ctgataacta tatataaagt tctggggagt   24660
ctaaaccaac tgcttctagg ctgactgcct gtcagttgcg gagccttgtt ttcttgtatg   24720
gttgtgagtt tctctttat tgagcatcct gaggacttaa attaaagatg ctctttcaga   24780
ggtgtttgcc aggagtcaga gcacaggact gacctgggag cagtttagga tatgatccag   24840
gcttaatatg ggagactctg gttgagacct taccttgcag agagtctgaa actggtttgt   24900
tgaatgcagc gccaggattc atgctttccc acaagactac tctggcgttc aactcacagc   24960
tcttgtttca gcttcttttt gaactccctc tgcccctcaa cacacacctt ggaaatttcc   25020
ttgatatttt tgtgaggaca acaatgcatt taaaagtgag agtggttgct gaataataag   25080
gaatgatcgt taactgttgg acattgattc tgatgacatt ttctcaaaag gataaccagg   25140 aatatttgt acaaaattag gattattata ataggcattt agttttcat tgttacaaat   25200 tttgaggaaa atcattaatc atttgaaaaa actaattgac atgtctccat tgtagcaact   25260 tgtatttca cttctagtat catgattata tcccctgtgt aatttggaaa ttgattttag   25320
cattaggaaa tttcctagtt tcagttaaaa tgaatttttt gtaagctgaa ttctatttta   25380
catgcacaac tttagtttgt tatttctttc cttgacaagc atttattgaa tgttgttata   25440
tgactaaaac tgtaagatga taatgtttta atattttcac atttctttca tagcttccaa   25500
agtgtatata tatactcaca tacttcatat atatgaatct acttatatac tgtatataaa   25560
aatatgtata taaatatata cacattgtat ataaatgtgt atatatattt acacatgtat   25620
ataaatatac atacaaatgt atataaatat acatatttat acacagatgt atataaatat   25680
acatatttat acacagatgt atataaatat acatatttat acacagatgt atataaatat   25740
acatatttat acacagatgt atataaatat acaaatataa atatatacat ttatatataa   25800
atatacatat ttatacacag atgtatataa atatacaaat ataaatatat acatttatat   25860
ataaatatac atatttatac acagatgtat aaaatatac aaatataaat atacactttt   25920
atatataaat atatatattt tttgatacgt acaactatct tgggagatgg gatattgtta   25980
```

```
ttatttccac atttacagat gaggtcctgt ggttcatcaa tctttgtgtt ttattcaaga    26040
ttatgtaagc agtaagggat gaaatcaggc tgagaaccca aatttcttca tccctaaaca    26100
aagtatttct tctaaacatg gtatccattt actagtttat ctctatcagg tgacccttta    26160
ttcattattt ttcatgagaa ggttgtagtt gtacaaagtg gctgatatct gataatgttt    26220
taatctaatt caaagtcgat ttcttaaatc caggtgtcag agtagcacac tactgtacaa    26280
ttctctgttt catgttttac aatttaccac agtcaagtta caacttgcac atgttacatt    26340
aaaatgtgaa ttcaccttaa tttcttgaaa tgagccagaa gaagaagtgg ttttgttttg    26400
tgatcaggga aatgctactt gactgccaaa ttgtctagaa cagcacatta aagttgcttg    26460
attttatact gttaaaatta ataaaacat ggcaactgtc atgtcatatg taacttttgt    26520
attattctgt aacttttttt gaaaataaaa agtgatcaaa ttgatcttca ggtaaagaat    26580
cttttttctc ttgattatct cttagtggat gatgatttgt tccatttaat gggtagagaa    26640
tttattgttg ctgttattgt ttcaaaagta gctgaatgaa actcttaact ttttcttcat    26700
agttaaaatt aaaacctcaa gtaaataat atttaacgtt ttgccaaact atgtaatcta    26760
attatgggct taatgcattt aaaggctttg tataatttgc tacgtatttt cacacaagtt    26820
acctgaacat aagtccagtc ttcctgctgt tttctgagtc acacagtgat tcagtgaccg    26880
aacagctgtt ggcagtggtg tgggtataat agggaaaaga gactgatggg gacaacccaa    26940
gtttagacaa gctggtaaaa gtagaagaaa atcttcttga aaacactagt gatcactaag    27000
ggctgtggag aattttttgct tggtgggtga atgtggaaga ggcaacagca tgggaaggtg    27060
ttggtaaagg agctccatac ttgcttaaac tgccttttga ttgtgaggcc gttgatgaat    27120
atttagtttg ggcttaggt ttttatgat acaggatatt ttccatttct ggctttgtat    27180
ctcagagatc acttagttac acttatagat gaataggagt ttcaattcct tgttttagaa    27240
agaagcttgg taactgttag tgagttacaa ataagccaaa tagaagaagg tacatatttc    27300
tgcagtatca ggtaaagttt ttcctcataa ggatttagac tcttggatat catattaatt    27360
ctcagaagag tgggtataaa aaggtatggg acttcttcct ggggtgggtt ggaggtggtg    27420
aaataccttt ttttttttt ttctgagatc atcatagaca agatcaaata atggtaaaca    27480
tgccaatgaa ttttctaagc actattcctt taagtgaaag aagagtgttt cagtaaaatg    27540
atttaatatt gggtcttcca aaagatggat ttaagagtttt caactttaaa agacagaaaa    27600
attaagttat tttacacaat gaatattgtc gtgccgtgtg tcacagacat gacatgagag    27660
ggaatcagag aacatacagt taatacaacg caaactagta tcattacttt tgctcaatca    27720
cttccattgt ctaagtaaga taattaaagg acagcataaa ataaaatttc aaaactttac    27780
tcaatcatat taagctattt taattaaagt aaatgtttta atgccattga atattcatca    27840
ccattcaaaa ttattgatgt aaatagtgtt atatgttaaa ggtaatttaa cttccatgga    27900
tgagaattca gctaatgttt cacttaactt ttaggtaatt ttttcaatat cctggtatta    27960
aacgaagtcc atgagtttgt ggtgaaagct gtgcagcagt acccagagaa tgcagcattg    28020
cagatctcag cgctcagctg tttggccctc ctcagtaagt aacttcacta aaaagggat    28080 tcttacagag gcatttgaca tcaaatatga acattgtaac aagagaatca tatgtacaga    28140
tggaagcatt caatgccttt tctgtcctgt gtagctcatt ttccagtaga ggatactttc    28200
aaggaaacta acagttgtga caaatataca catctcaatg tagagttttg ctttacatca    28260
ttcttgattt agctttgtca ttaagcagct aatctgtttt aaaaaatttt ttatttgtgc    28320
ctgggcatgg tggctcacgc ctgtaatctc agaactttgg gaggccgagg cgggtggatc    28380
```

```
acaaggtcag gagttcgaga ccagcctggc aacatggtg aaacccatc tctactaaaa    28440
atataaaaat tagtctggca tggtggcggg cacctataat cccagctgct cgggaggccg    28500
aggcaggagt atcgcttgga actggagggt aggagttgaa gtgagctgag attgtgccac    28560
tgcactccag cctgggcaac aagaatgaaa ctccatctca aaaaaaataa tttatttgtg    28620
ttttaagttc tggtgtacac gtgcaggatg tgcaggtttt tcacataggt agacgtgtgc    28680
catggtggtt tgctatacct attaacccat cacctaggta ttaagcccag catgcattag    28740
ctattttcc taatgctctc ccttctccag tcccatcccc taacaggccc cagtgtgtat    28800
tgtccctctc cctgtgttca tgtgttctca ttgttcagct cccatttata agtgagaaca    28860
cgcagtgtgt ggttttctct tcatgtgtta gttatctgag gataatggtt ccagctcca    28920
tccgtgtccc tgcaaaggac atgagataat tccttttat ggctgcatag tattccatgg    28980
tatatatgta ccacattttc tttatctagt ctatcattga tgggcatttg ggttgattcc    29040
atgtctttgc tcttgtgaat agtgctgtga tgaactaatc ttttcaaata atcctcctct    29100
cgtctattag gtttttttt tttttggtac cttcttcctc attttattat ttatctggat    29160
aggatggtag cattatgaga cgtataatat attaaaaatt atctttataa ttgaccaagg    29220
cttctcctaa agcacacctc attctgttgg taatatttca aaatatggac ttagagttgg    29280
tcaaactgtt aagtagataa tatatataat gttttatat attttcaat tttttcaag    29340
ctgagactat tttcttaaat caagatttag aggaaaagaa tgagaatcaa gagaatgatg    29400
atgaggggga agaagataaa ttgttttggc tggaagcctg ttacaaagca ttaacgtggc    29460
atagaaagaa caagcacgtg caggtaggac tctcataaat attagagtta ttcaaaatta    29520
tgttttccag tcatttatat tttgacagat ttcttttttc tcccctaatc caggaggccg    29580
catgctgggc actaaataat ctccttatgt accaaaacag tttacatgag aagattggag    29640
atgaagatgg ccagttagta gttttgattt tatatgatag aaaatttcag ttatatttta    29700
aatcaatacc tataaaatac cttaaccgta acttttattg ttagaaatat ttttgatata    29760
ggcatttagt tttagatgtt gctgcaaaat agtagtaggt atgtagtatt ttgatctcat    29820
caccttcagg agttagaaaa ggtagaatga gagttattat tgagagattt ggaatcaagg    29880
gtcatttggt aattcatgaa tcatggagaa agaatctttc tattttctgg ctgatcgttt    29940
taaaatgcca tattaattca tcttgggtga tagaaattgc agagccatct gtgatctttt    30000
cttctatggt gactagccag caggttgtca atatcagaaa ttagatttgg ttagagagct    30060
tcctatgatg agttcccaac tgatgtgaca gagttgacct gtcttctttc gagagggtta    30120
tttgaagctg tcatctctgg ataactcttt caataggagt gccattcaaa catcataaga    30180
ccggcactct ctcccaaaga tacaagctgt agcaaggagt tttgtgcata tcaggttgt    30240
ttcatatccg tgagcctttg tgttttatgg caactgattg attatacttg tgctatttgc    30300
aatgggtatc ctctgggttt taaatagtga atgacttatt ttggaaacaa atagtagtat    30360
tctatgtctg aaatcttgac cgtctatttg tttaattatc tattgctgat aagaagggaa    30420
ttaataacac agatgctact taattaaata ttttcatttt gacaagaaac agtaattctt    30480
ttgaaaacta tgctaaattg gcatcttaat aatctcatgt tgagcaaggc ttttggagat    30540
tagggtaagg gagattcatg tcgcagttta taaatttcag ttcataggat acctattttt    30600
caatatccat aagataactt taaaataaat atattattaa aacaaagaaa atatatttac    30660
gttatacatc tttaaaacct accttgcttc tttacaattt tcagttttc ctctcttgtt    30720
```

```
tccattctct tctcctcact ttaccttttt cctcagcatc tctttacata tctgctgagc    30780
ttttttattt ctctctgctg catatgcttt tgaaaaagca taaaaatact aatttgttag    30840
gatttaatta attcgagtct taaaaaatga actataattc actcttgtaa gtggaggtgg    30900
catgaaatat tgtttatatg ctcttaattg ttgttagaga tatttgataa tggcaagtga    30960
gaatttgaga tagttattta aaagattact actaacattt tgtttgaatt tttgaaagtt    31020
tcccagctca tagggaagtg atgctctcca tgctgatgca ttcttcatca aaggaagttt    31080
tccaggcatc tgcgaatgca ttgtcaactc tcttagaaca aaatggtaag cagtgggcca    31140
tgttttcaaa taagggaaa cacattttg tggtattttt aattatagaa gctatatact    31200
gtgaaaaatt tacataattt ataaagctat atattgtgaa agatatctct atgtgtagag    31260
atgtattgac atatggatta tgaatatata ggtaaaagga tgaagaataa aataaacatt    31320
tgttgtatat ttttccggac ttctatgtgt aaactcacac atgacatata caaaatttta    31380
tgtattttgt agaaatggga tcatattata ctcttttata accaaatttt atttattctc    31440 tttttatgt tgatacatgt gtattctcac attatcattt tatttttaat ttttaaatt    31500 aattttgtt tttagatatg gtctcactct gtcacctagg ctggagtgca gtaccatgat    31560
catggctcac tacaacctca aacttttgga ctcaggtgat gctcccacct cagcttcctg    31620
agtatctggg actacaggca tgcactgcca tacctggcta attttttgca gagatggtgt    31680
tttgccatat tgcccaggct ggtctcgaat tcctgggctc aagcaatcca tctgccttgg    31740
cctcccaagt gctgggatta caggcatgaa ccactgtgcc cggcccaaat tataattttt    31800
aatagctttg tagtttttca gtgcttgcct gtattctgtt ttatgaacca atttcttact    31860
gatgaagttt tagtttgtgt ccagtgggat gtttctggaa cccatagtaa acaccagtga    31920
tcactttcct cctctgtttt cctttataca tggttcctat tattttcttg ggaaaatttc    31980
atagaaatgc aactgggtag agagctattc accatttaa aatctggtaa aattgtctat    32040
tataaatttc cacactatac tttttaaaa aatcgttctt taatgtaatt cttataaatc    32100
ttatagcttt gtataattat gaagagaaaa atggcttgta tccctttaga aagacatgag    32160
ttttaagatt atggttcagg ctgctcaaat ttcttccccc ataaacagga atactgccag    32220
aaatccttag gtgaaaactc atcataaagg cattgggact tggcagcttt tgcaggacat    32280
ttttagaggg caaaaaatag agaaaaacac tgaaagtcag agacagagac cagtgtaagc    32340
atcagctttt aatagagaaa ctgggtaggg tggaaaaaaa ataaagcaac cacctcatgc    32400
atgtttcttt atattattat tgaagtcaaa taaagaggaa aatcatttct tcttcctctt    32460
cctccttttt catctcacct ctccaatggc actttaataa aacgcttgga gtggccaggg    32520
cactgacaga cagacagggg ctgctctcaa ggataatgag tcaaagggga aggagaggga    32580
atcgctgttc tcgaatctct cttattctac tgtgcagtta aagaggtctg gacagggatt    32640
tcactcctga aaatgaggac tggacttgt ggcttctgtt ggggcacctt tagagtggag    32700
gtagactttt actatgtaca gacaacattg tgttggtgac atcattcata accacctgga    32760
aatctccttt gatatgcaaa tcaaacaacc ataactttgt gaaatttcga ctgcttccta    32820
ttgtggtgtc tgaggactgg ttacattcag agtccaccct gatgtctttg ttcagttttc    32880
tgctctttct agttccttac ttctttgttc ctgatcacct gtcaagtaaa atgtcctcag    32940
atccttttgt attgtctttg gagttctgcc ttaataaagc atgaagaact tgagtagctc    33000
gttcatcaac tttcttgggc aatttctcat tgaaagacac ttgggtgtct ttgggtgtgc    33060
agagctgagc atggctttat gttttagaa aaaatggcta cattggcagg cagaagaact    33120
```

```
gcgtccttgg aatcatggag gtcccaaggt tgcatacatt ttgtgtgaca ttttttcctat   33180 tcaattaatt aactaatatt tattgagctc ccaagtgtgt agtgtctgta ggcacttggg   33240
atgcattcat taagtaaaaa tcccaggctc atggagttta aactgtagta gggaagataa   33300
taagattaac taaaatatgt aatatttgag gcagttaaga ataaaaaatg aagcaaggaa   33360
ggagaatatg atatgttaga catcagagga gatgaagttg tgaataggca gccaggaaag   33420
aaggtgacta ttgagtaaga cctgcagggc gtcgcatatt gttttttgcc tctgaaagca   33480
gttaatttcc tgttaaaatg gagtggatga gatcaagagt attacgtaga tagctggtaa   33540
atgcgatagt gtgtaaaatg ttctataaag tctaacgtga ctttatgatg aaatttcttc   33600
ttctaggttt attgcttgca attttcaaac cacacattgg gttactgtct aggatagtga   33660
ttcttaaagt gtggttcctg gaccagcagc atttgctggg ggaacttgat aaacagtgta   33720
aattcaagga ccccatacag accttctcaa tcacaaaccc tggagttgag acccagcaat   33780
ccatgtttta acaagctctc caggtgattc tgatgcacac taaagtttga gaaccactaa   33840
cccagtgtca tttttgtctt ttaaagtgtc ttcttggcta gaagctagcc actttgggaa   33900
aggttattac aacttctgat gtgatcaagc aaagtaacca actctttatt gtatcttaat   33960
atgtgatatt ctgaatgtgt ttaaaaggta tgagtttttc aggctctggc agtatttttag  34020 aatgtgtatg tgatttctat ttatttccat gttttgtcct atcttcttaa gatagactac   34080
ttattttaaa agcagtactt aagttaaaac ttttttatgtt tcttttttctg ccactttcaa   34140 agtgttgaat cacagtgtgt aatgttgaaa ctgatatttt tatagcggct tcaagacaat   34200
tgatatttat gtggaaactt gaagacagta ggtttatgtt tagtgaagga agtttattac   34260
aaagaggaaa attggccagt tgtggtggct cacgcctgta atcccagcac tttgggaggc   34320
caaggcagga ggattgcttg agctcaggag ttcaagacca ggctgggcaa catagtgaga   34380
tcccctctct acaaaatatt aacaaaaatt agccaggcat ggtggcacac ttgtagtccc   34440
tggtacttgg aggctgagac aggaggatca cttgaggcca ggaggttaag actgcagtga   34500
gctatgatca tgctactgca ctccagcctt ggcaacagag agagatgctg tcacaaaaag   34560
aaacaccaac aaaaaagag gaaaattatt ccttaatcat tattgctgga atatagttac   34620
tttccacaaa tagtgaagtg ccagttgtaa agcatatcta tatgtttcct agactttggc   34680
attactttgt gaaaataact gtaattactt atgttctatg taaatgcttt ccattcattt   34740
gtatatgatg gcatatatag aaattataat gtttgtaaag tccactggga taaatggaca   34800
aagcagctga aggctgaaag caaccaagcc ttttacagcc ccttcattcc ccacactccc   34860
aaaaagctga gtgaatggtc gatacctcca catgcttata actcattccc agcccaccag   34920
tgtctagcat atctggttag tcttagcttt atataagtgc agttatttgt gaacttgttt   34980
taagtattgg aatacaattt aactttcatt cttatttggg agaccattat ttaaacagat   35040
ttcttttttc ctgcaaaaac actcttttca caatggacag agacacggtg attacattaa   35100
aaccatctac tctatgaata aaaatgttaa aaccaaaatc ccaacaaagg gttaataaag   35160
gcaaaaaaaa ttggaaatga catgtgtttt aagaaataa acatgaatta tctttaagct   35220
gtcaatgaac tataaattat gtgtgctctt gtatatgctt tcctgtaaat ttggactata   35280
ttaatattct aaagcttatg gtaaaattat gaaaatatgc tttcatatct ataagtaaca   35340
ttttaaaaaa tctcagttaa tttcagaaaa atactgttat caaaaggaat acacctgaat   35400
gttttggagt taatgcagaa gcatatacat tctcctgaag tggctgaaag tggctgtaaa   35460
```

```
atgctaaatc atcttttga aggaaggtaa tatagattca ttaacttgta cagaatatat    35520
catattgggc caggtagaat atcaatattt caagcatatt tctaacaatg aaaagaaaaa    35580
gaaaaacata agacacttga aaactgaagc attttgcaat gtaatctcgt gtcactagta    35640
ccatagactt actttatctg aacactgaaa ggaatggcaa gattgtggaa acatgttgaa    35700
ggtttgcttt tgaacctgat gcttgatgtt gactatattt tgaaaagtgg taattgtata    35760
gcacatagca tacagcagtt tttctaatta ttgtgtgtgt gaaagttata aaagataaaa    35820
tcagtttatg gctaaatttt gctctttcac aacgaatata ttattccttc atctgaatga    35880
actttgtctt ctcttcctgc tctcaatcct tagttaggga aaattttaac tacatctagt    35940
ccaagtgcag agatgctaag attatatagc tggcggttag tggcacaaca gagaccatat    36000
cctttgatct atgtgtggat ggtggtgggg cagggtggga tgaggtgggg gtgaggggtg    36060
gtaggtgtgg gcagaactct catgtgtaaa aaaataatt ggcacagaag ttgcagtgaa    36120
aactaatttt gttcctggtt ttgccactaa tttgagccaa ctgtttcatc tctaaaactt    36180
cacgttcctc attgataaag aggaatgata ataacaactt tgaaagttgt aagcttagaa    36240
tgtaaggatt aaataaatta attttttacaa agggattagg ataatgcctg ctgcattta    36300 agcactcaac aaattgtgtc tattgttgtt atactgttac taagtgtgaa taatgaagt    36360 gcatatagca tgaaatgtag cgtaactgca gacttgtaag aagtagggtt acactgtttt    36420
taacatcagt ctaactaatc tatgtttata tatctttcta agctgtattt ctcttattta    36480
agtgttgttt ttgaacactg agatgaaaag tttatcttaa atgttgattt taatggggcc    36540
ggaagtgtgc aaacctttac aaatgaggca aaaacacagc ggaataaact ccagtctagg    36600
attctgtaga ttctgggcaa ggcatttaat gtttctcgct gcatgctctt acgtaaaatg    36660
tgtacagttg cagccctgga gattccgcat tggctctgac agtgtgtctg cccctacaga    36720
actcatgtga gtcgagagac tgataagtaa acagattatt ataatacagt ctcagaatgc    36780
agtggcagta gtgtgtaaaa gacgcaatgg taagagtaga gtggactcag ctggggttac    36840
ccaaggaggg gaggctccaa tggagggatg tgtttaaact gggactttaa gttggaaaag    36900
aaggaatgta tctcagtgtc cacagaacca tgcaaagtga gaacatggtt ctgatatgca    36960
caagtttcag ttaacaagca aagcaaggat tgactgtatt aaagttcata gtacctactg    37020
cattctagtc aagtgacatt tgctcatatg taaaagaaag aatagcttaa atacctgaga    37080
gaaaccaaga ctgtaaaaca aattaaaaat aattaaaaat accttataag aagtccagtg    37140
atgttaatct ggaagaggaa ggttcgtgtg atgtaaagag gccttgtctt ggggtcagac    37200
aagtttgggt accagccttg tctctgtcac tttctagtga taagacctga atatttaacc    37260
tctatctgtc taagttcttc atgtagaaaa tggggataaa acacctacc tgctgggatt    37320 gttgttattg acccatcgta ggtcagaagg atgttgttag ttttatgaag tgaaataatt    37380
cccggattac tatgaattct atcttatgag ttcaaagttt agacaattaa aattatgtat    37440
gctcatacta ctgatttcaa atgcattttc atatagtctt tcctgataaa atatattggt    37500
tctgccctcc tgtacttatt tcaatttggt gtttatacca ttgaatcaga tcagtctttc    37560
aataagcatg ccaattttat atccccagca acacttccct ggatataatg gcagcagtgg    37620
tccccaaaat actaacagtt atgaaacgtc atgagacatc attaccagtg cagctggagg    37680
cgcttcgagc tattttacat tttatagtgc ctggtaagtt acatagttga ttgtgggaag    37740
agataacaat ttaaatggat ttttgatttt tcatgaaata gcaatattct aggcaaatat    37800
taaaagacta gtttctgtcg actaaatgta aatctttctg ttaaaccaaa aagaggttaa    37860
```

```
atatgatgca gaagagtcac ttagattaat ttttataaga aagcaatatg aattcagtaa   37920
tttatttata caaagtaact acaatgtaaa atgtggagct tttatttta aggagggtgt     37980 tcatctctga taattctttt ctattttgt tgccatgacc tgagttcaag ctttttttct     38040
cttgtttgaa ttgtactatt agctaatttt catacctgtt ctcttccttc atttctatcc    38100
ttttcttact ctatgattga attaatcttt ctccaatgtg gcttgtactc atttacctca    38160
atggcttcca ccctccaccc acctttaatt gttactgaca tctgttatca ccttatttgt    38220
tctccaaagc ccctttaaaa cacctatgtc tgtattcatc caacacattt attaagtgct    38280
tcttatgttc taagcactgt gatgctgtta aactttaaaa gatgaattgg aaaaaaagca    38340
caactgtact attataggag cttagaggta gatggaagtg taaatagata attaacaggc    38400
agcgtgagag aggcgatgat agatgcatat ataaaaggct ttgagaatat cgatggaggc    38460
acaaataatt tcttcaaagg agtaggacag agattgtaat atttgaggtg aagggtaga    38520 tagagctggc ctggtagaaa ggccaaggaa gacatttcaa gcagaagaaa gtgcacatgg    38580 tcggggtga gtgaggcatg gaggataagg agaggagtgc ttggggatga gtgtggaagg     38640
aaaggctgag gcccaaagaa aagggccttg aatgcagtgc taaaaatttt ttgccttta     38700 aaaatggaag ccaacccaag tttattaaaa ttgtttgcag attgtagtgt cacaccgaaa    38760
tttgcaacta aagacaatag cattgtggtg cagaggatga tagacaggga gagagactag    38820
atacaaggag attgggttgg aggtccatgg tagtcaagtg agacccagtg aagggaccca    38880
gcaatggaaa cacagatgag agggcagatt ggacagatgg ttgggagatc tgtttgatgt    38940
gacatcgtga tccctaagta tgagggatga tactttgttc tgtgaagttc ccaatctttt    39000
gaagtcattt ttgctttgtt cttttaaaat gaaatcttcc taaatctatc attttctcta    39060
gttatatagg tattttgttt ctctgtataa gagtattact caatataaaa gttttttcaa    39120
ggacagagct ttcttcagtc attttttct gggcccccca gtcctctggt ggctattcaa     39180
tcagtatttt aaaaattgaa tcatggtgtc ctattcatag tttcagctta gttttgagac    39240
gtaatgtaac agatgtaatt ttacttgaaa atattattgc atgttttatt gaattttatt    39300
tttagattgt aattaaaaac aataaaaatg ccttttgatt atccttaaag ttgacagcct    39360
tattcttttg agggaggttt tgggttttaa agataaccaa aggacactca aaaccgttt     39420 ctgttagtta ataaaataat actcttttag tccaaaagca agtttgaat acagtatttc     39480 ttttctttta ttgttcttaa actgatcctg aaggaaaatt gttagttaac aatcaatcag    39540
atgtattatg ggtgcccttg aaaataatca cttgaggact gtacttaatg taaaaaaata    39600
cattttataa gcatatcagt atgtaagtac attcttctag taggtaaagg cttaatcatt    39660
tactgtatgc taacatatta tactaccaca gtacaccata ctgtactgta cccaacgtaa    39720
tgtaccatgc cgtgcagtac cgtatcattc taggtatcaa caagtaacta tggtagcaat    39780
actccagtag ttttgaggtt gaatatgatt ctggtttgaa catgttaagt tgaggttctt    39840
atgagatacc taggtgtaca tgtattcatt tattagctag attatattca ggttttttag    39900
tggcaaagat gtacattatg gcaaatgtgt ataatttagg gtccaattaa ggatagcata    39960
ttgcatctag tgcatatatc ttaagttct ttcaatctat tactgtactt tttctcttct     40020
actttataat aacttgttat atagacattg agctggttgc tttaagaaaa taataatgaa    40080
gacccagtta cttttaataaa atatcatttg acttgttct tgagttactg ctagttttag    40140
aggaaataat gtgaaattct ttaagaaggg atataggcaa attgggaagt atatagagga   40200
```

```
gagtgattag ggagataaaa gcacatcaaa aagagcaata agaggaactg agattgtttt    40260
atttgaagaa gagatgactc aaagggatat gaaactctat tcaaatctac ttacttataa    40320
ccagtaacag taataatacc aaacaatatg gaggacttaa aaagtattag gcattgtttg    40380
aagtatttta agtatattat ctcttctgat tctaacagca ctccatgagg cagatattat    40440
tattattatt attttggtat tgtatggact acaaaactga ggcatagaat tgtagagatt    40500
tttaaggtca ggcctgatat aacagcacca gattttcagc ttatgcaggc tgactccaga    40560
gtaggcattt taaaataaat atttgtgcaa caatcttgtc ctgaacaact gttgtattta    40620
aagcactatg tctagaatcc ttaaggtatc gggagatgat gagattatgg atactgctct    40680 caaaaaatt tacagtccac acgacctaaa ggactgttat gtagaaagga aattatatcc    40740
atttgaatag taggacctca agtgatagaa caaagactgg agaagaaatt tacaggaatg    40800
ttcatttggt cttaatttaa ggaagatgtt aaataagacc cattacatgt agcatgatgt    40860
ttttactact caggccagtt ttagtggtca catcttctta aggtgtaata ggcagcctca    40920
gaagttactg tggtcttgct cactggaaat gatacacaga cagtttaagg gacttgcccc    40980
agaccacacg gcaagaggtg aatgtcagaa cctctttgag tacattttaa aataaggact    41040
gaaagttgga ggagggtggt tatcaaggct gccttcctta ccatagtatt cccagcatta    41100
acaaaatcct tggcatgtaa ttggaattca gatgcttctt aaataaatga aaagcctgtt    41160
gtagccagct tacagtttgc attaatgcag attattaaag tggaagatca taatgatttt    41220
tttattaata tttatgtcta taatcttagg tttggaaaac attattcatt cataataatt    41280
ttaattatat gttacattac cacattttg acttgtagtg tttttagcat agttcagcta    41340
cagtgtagct taataaagaa tatgattttt taaaatagca atgctattat atagccttta    41400
cagaacttct aaaaaatgac atgttctcta ccaccttaat actgaaactc aaatcttatt    41460
ttttgctacg attattccag ctactctttt ttgtctatat ttcatttctg ccttttatg     41520 ttgtggtcca agtaactctg agcttttctc atgttgtcca ttgttgcata aaaatcttcc    41580
agcatcttaa agcacagcct actcacacaa aaaagtgatt gtttgctaca gaaaatttct    41640
tcaccatcgt aattttttgc tacttcaaat tcagtaagca ttcttacaca ttatatttat    41700
tttatattca gtgatgaact atttttatag attccttaaa atttctggtt attatttga    41760 taaggaaaca tgtactagaa aaagtacaa cacatatatt gtgagattaa ttatgacaat    41820
ttctagaaag taacagtctg ttcaactcaa atgtttataa gaaaattctt tctttattta    41880
tttatctgtg catttaggca tgccagaaga atccagggag gatacagaat ttcatcataa    41940
gctaaatatg gttaaaaaac agtgtttcaa gaatgatatt cacaaactgg tcctagcagc    42000
tttgaacagg gtatgttgaa tataagtttt ctgtatttat actattaact aaaatattaa    42060
atttggagaa ctagggcgc ttttcagtc taagttttct gttctccgtt tgctatgata     42120
ggaggaagtc atgtggttag agacataaga tgacagtggg gatgtgggaa gtgaaaagat    42180
atgtactaag ctaagtccag ctaagtgtat tatcaattat agatgtaggc aagattcttt    42240
tgattgccag taacataaat ccactctagt ttgctcaacc agaaagagaa ccaaagagcc    42300
atatatgcag ctagaccttg tgagtcatgc tgggtactat ggctgctgtt ttctcttct     42360 gtcctctggc tacttgtctt tcttttctgg tctcatagta tatggtttag cccatgaaga    42420
cataccagtg ttaacagtaa agtcttcggc tgggcacagt ggcccacacc tgtaatccca    42480
gcactttggg aggctgaggt gggtggatca cgaggtcagg agttcgagag caacctggcc    42540
aacatggtga aaccctgtct ctactaaaaa tacaaaaatt aactgggcat ggtggcacgt    42600
```

```
gcctgtaatc ccagctactc aggaggctga ggcaggagaa tcgcttgaac ccaggaggca   42660
gaggttgcag tgagctgaga tcacaccact gcactccagc ttgggcgaca agagtgagac   42720
ttcgtctcaa aacaaaaaca aaaacagaca aacaaaaaca gtaaagtctt ctttgattcc   42780
ctacgctcct tttcattgtt ctccggagaa ataacctctg aaatgatttg gtatacattg   42840
tttccatttt ttagcattta catatccatg ttcctacatt ataattaaag tatccataaa   42900
tcatactgag tatgaaaaag agaagaaggg aattacattt aaattgtgta atgcaaaaag   42960
tattggtgga attaagaagt tttggaaatt ttgcataaga tgaattggtt ctttattaaa   43020
gatgttaaga ataaagacat aattagtgtg aacatttta taaaggagg agcctattta   43080 aaataattaa tggaaatgat tccatgtgat ttgatatact ttgatgaatg tcataaatta   43140
attaaagtgg cttccagaga gatctcccctt aaaaattcat tttaaattga acttatact   43200 gtcactcact gcctataata tgtttgagtc atttatactc aaactttaat acaatccttg   43260
agtatggcaa gaatttatgt tgtaatgggt taaatttatc ttgagaaata tttgttgaaa   43320
ataagtatat ggaaggaagg ggttaggcat ttagaagata aataaatatg ctttgtactc   43380
ttctctcctg aatctcataa gccggttgtt gatggctgtt gtgaaacctt ggttcttttc   43440
tttaaacaag agacacacag cagaggagat gcagcatcga gtaatttatt gcaaaagaaa   43500
aagaatattt tgcaagttaa gtgaggaata gacacttata ccctgacaga attcagggtg   43560
ggcttactag taaggatgag acagcgtaaa ttggcactag gaagactccc tttgtgggag   43620
ttgtacatga tttttcataa gtgggtggga agaagtgtta ctagtaagca tattctaggt   43680
tgtcctctga gtgaacatgt gcagtagctg tacatgcttg ttcatatatc gcatgtctca   43740
taagtatctg aaatctccac ccaggggtgt gtgttttact attataatga gcaaagggtc   43800
agtctgagga caaggaaaat caaaatgtgc atgctcccca cgctacctga cttcaaacta   43860
tactacaaag ctacagtaac caaaacagca tggtactggt accaaaaaag agatataggc   43920
caatggaaca gaacagagcc ctcagaaata atgccgcata tctacaacca tctgatctttt  43980 gacaaacctg acaaaaacaa gaaatgggga aacgattccc tatttaataa atggtgctgg   44040
gaaaactggc tagccatatg tagaaagctg aaactggatc ccttccttac acctttataca  44100 aaaataaatt caagatggtt taaagactta aatgttagac ctaaaaccat aaaaaccccta  44160 gaagaaaacc taagcaatac tattcaggac ataggcatag gcaaggcctt catgtctaaa   44220
acaccaaaag cagtggcaac aaaagccaaa attgacaaat gggatctaat taaactaaag   44280
agcttctgca cagcaaaaga aactaccatc agagtgaaca ggcaacctac agaatgggag   44340 aaaattttg caatctactc atctgacaaa gggctaatat ctagaatcta caatgaactc   44400
caacaaattt acaagaaaga aaaacaacc ccatcaaaaa gtgggcaaag gatatgagca   44460
gacacttctc aaaagaagac atttatgcag ccaacaggca catgaaaaaa tcctcatcat   44520
cattggccat cagagaaatg caaatcaaaa ccacaatgat ataccatctc acaccagtta   44580
gaatggcgat cattaaaaag tcaggaaaca acagatgctg gagaggatgt ggagaaatag   44640
gaacactttt acactgttgg tgggactgta aactagttca accattgtgg aagacagtgt   44700
ggcgattcct cagggatcta gaactagaaa taccatttga cccagccatc ctgttagtgg   44760
gtatataccc aaaggattat aaatcatgct gctataaaga cacttgcaca cctatgttta   44820
ttgtggcact attcacaata gcaaagactt ggaaccaacc caaatgtcca acaatgatag   44880
actggattaa gaaaatgtgg cacatataca ccatggaata ctaagcagcc ataaaaaatg   44940
```

```
atgagttcat gtcctttgta gggacatgga tggtactcag caaagtatgc caaggacaaa   45000
aaaccaaaca ccatatgttc tcactcataa gtgggaattg aacaatgaga acacatggac   45060
acaggaaggg gaacatcaca ctctggggcc tgttgtgggg tgggggggagg ggggatagca   45120 tttggagata tacctaatgt taaatgacaa gttactgggt gtagcacacc aacatggcac   45180
atgtatacat atgtaactaa cctgcacgtt gtgcacatct accctaaaac ttaaagtata   45240
attaaaaaaa aatgtgcatg ctccatacag gggcaattcc ctactggaga tagctttgct   45300
taaatgagct ggactacaat gcaaatgctg aaacttacta tattgacagt aagattgcca   45360
cagttgccgc gtcctgagga catggttact tccttttaat acctatcctg tctcattgtg   45420
agaggattaa caactgtgca taaaaccagt tgttctacat gagcacttag gagggatacc   45480
agcattgtga acatagttta agtacgtaga ggagggaaca gttaagttta ttcatggtga   45540
gtgttggtga aaagtggaag aggtaccaaa acagccgtat agataactgg ttccagttag   45600
ccaacattct ctaaagttat tagagaagcc taagtgaggt gtaacctcag cagtcgggag   45660
ccaagagagc aagtaagtgc tgtgatgtgg agaaaatcac tttgttccaa ctgagaagaa   45720
atggttgagc actgcttttc ccccatgcca gtactgacgc acagcctttc acttagcact   45780
gattatcgat aggggtgggg agttaaggta tggggaaaca caagtaacaa tattttattt   45840
caaaaacctc tccactgtaa ttcccctaat ccttcatcat ggttgaggaa aatggctcta   45900
aaaaatgaga gcaattactg tagctccaaa attctgtgat tgcatgtctt actctgaata   45960
gcaattacaa agcatcagag gatttaggtc caaatattgc agacacaaga aaatgaatta   46020
cattttaata catctaaact tggagagcag agttccaaat aaggtagaac ttgagattca   46080
actctgattt ataaagcaga gactaagaag agtatttata aagcgaatcc atgtttggat   46140
acataaaagt gcaataaaat tcaagctgaa gttaaaatct ctgtctagaa cagcgatgtt   46200
ccatttatgc ctgatccttt tagcttttcc acagatgaag actttgtcac ctgttccaga   46260
gagatatatt tgttcattat tgtttccaga gagcaaaatg gaaaataaac tctgcacatt   46320
ttggccgcat ctgtgtttta tatgcggtga cactcctgtt ctcttcagtg aggaaatcca   46380
gtaaagtaaa accagtcttc tgatgaaatg ggcacaaatc aaagaacttg tgagcttcac   46440
aaaaaccttg aagcaaaata taccaagctt aaatattgaa tgtattgatt tcagtagtca   46500
aaaacagagc tcatctgcaa aagcaacaac aacaatgaca acaacaaatt acatataagt   46560
aaaatttaaa aaaggtttac aggatgaata tacagaaaac tatgaagctt aggggtagag   46620
aggagtagtt gaatatatga aaagatacat cttttttgat gaaggactaa attttttaaaa   46680 atgaaaattg atctatgttt atgaaccatt agtaaaaata acaatagtat ttctggaac   46740 taagtaagct agtgtaaaat ttgtatgaaa aaattaatac atatgagtaa tcaggagaat   46800
tttaaaaaag agtgttgatt catatggcct aactccaaaa gataatcaaa tgtattatac   46860
aattttagta attataatgg tgtgatactg gcactagggg agagagatca gtgccacaga   46920
agggtggctc aggaaataga ctcaaataaa aatttgtaat gttatgatat tcctcgactg   46980
cgggaggaaa atagattact cagttacttg tgttggaaca actaactctt cagccatttg   47040
ggaaaagcaa agaagctgaa atatttatct tactcctttt gccaaaacaa attacagatg   47100
gatgagattt aaagtctata atgaaattgg tatatgtaca tattaaaagt ttcaactata   47160
attgttatta acgtaaatga caacggaaca ccttgttgga gggaaatttg gtaatatcta   47220
tcaaaattaa aatgccatgt tttctgatca gcaatttcat tctaagaatt tttaatgtag   47280
atatacttgc tcatgtacat aaagattatt agacatgaat gttcactgtg gcatgattcg   47340
```

```
taattaaaaa tgtggcaaca aactaaatgc ttacatggta atcattcatg ctgtttgcca   47400 gatatttta tttctccacc ttgtggtgat tctggcatag tatttagtag ttaggttgaa    47460
gcatgtgact aattttggtc agggagttgt aaatggaggg aatagctggt gagacatctt   47520
gcggaatact gtctcaggta ccatcgtacc tgcagtgttt gagatagtag ttgctccatc   47580
agtagaggtc cctgagggac tacaacaagc agagtcccct cctgacctgc aacacatatg   47640
tagcatgagc aataatggaa cttattattt ttgcaccccta taaaattttg agaattgtta  47700
ctgcagctta atttaatctt tcctgacaat acaataccta tcaatagaga ctaatcagat   47760
aaattatacc atttccaaat tgtatcatcc tgcataaata ttaaaaaaca atgaggtgag   47820
attcctaatg tgctgctatg gaaaaatctt caattttcta tgtgtacgaa tgtatttccc   47880
aggtattcgt ttttccttc ctgtatgttg acacattatg cacacttttg gatgaaatta    47940
atatatttcc accgctttat gtcctctccc tcacttttat cacccaattg tagcaaagta   48000
tatgtttgct tttatagctt tagctatata aaattttcta atagctaagt ttgtggttcc   48060
tggaattaag atatctgaat ttaaatctaa cactactacc tacagactat gcaccctgga   48120
caagtactta atgtcttggt tttgttatgt ataaaatgga gataataact gattttttcac 48180 ttagagttgt tgaatatttt ataagataat tcatgaaaaa gtgtcagtat aatgcttggc   48240
acatagtatg cgctcaataa atgttaatgt tattactatt agatttaaaa gtatcttttg   48300
acccctggct atagaagatg aggaaatcag agtatttgca cttctaatat ctcctgtttt   48360
cccacctact tttgttcaat aaattaactc cacattggca gggtagataa tatttatatt   48420
cagctttcta attatgcttt ctaagtttgt gtttatctta ctcctaccgt tatttggaag   48480
cagtcttcat ctcaagtcct tttgttactg tttttttcact catcttttag ttgtctgaat  48540
ttctttagaa agtttaatt ccctgaatat ttaatgttta tattttgttg ttgttttttgc   48600 ctttatattt ggactcctaa aaaagttttt gttggttgta aaatattgtt ttttttttcct 48660 tgaagtgttt gtaggcattt cactgtgttc tagtactgaa tgttttagtg gagaagtctg   48720
aggccagctt catttgtttc ttggatattt ttgcccagtg ctgaaaggat ttttctctt    48780 gaaatccatc cactttatta gggtatatct caatgttagt cctgggatat ggtatcctca   48840
ttctagctat acattcaact ttttttcctgg aaagttttct tgagttgcat ctttatatac  48900
atatacatac acgaatacat atacatggta aagatattaa ggataaagat aggtgcttta   48960
taaataccaa tttgatataa ttttggcatg aaaaaaagcc tgtggtgcat tctgagtttg   49020
gaagtagaac tggatatact tacttattac tattgttttt aatacaaaaa tggagacagg   49080
gtctcactat gttgcccagg ctggtctcaa actccttgac tcaagcaatc ctgcctcgac   49140
ctcccaaagt gctgagatta caaatgtgag ccaccgtgac cagcctaaat atctaaattt   49200
ttctctttca ttattttagc tctcttcttt ggggctatca gtcatatgat gttggatctc   49260
ttttgcctta atcttctaat ttttcaaaga ctaatccaga gaccactatc tatcaccatg   49320
ccattactca tagacaaggg acatcattcc acacatttag cttatttgtc aaaatcagag   49380
atgggattta taaagaaaaa agaataaagg gagaaaacaa aacacaaatt atctgggaat   49440
gcgagtctgt tttcctttct ttggctaatc tacttaccta gtagctagga aagaggccag   49500
catgagtatt tttccattga gctggctagc tcagtcattg gagaaaccat ttcaatattt   49560
atggattctc tgaaaaaaac ttggagagta aaaaagcata ggtggtagga tgctgccatc   49620
cttctgttgg catctccaga gtttcacttg aaaaacacct cctaagtaga cactgataaa   49680
```

```
ttgatttta  tccctatttg  agcaccaatg  caatacatta  ctatttcaag  atggagcatt   49740
agataactaa  aggaaattct  attgtgggct  tgtaaatatc  atgatagtca  tacctatgta   49800
atacatatat  gtatatataa  atattaattt  ttaaacattt  acttagctat  taaaaatcaa   49860
atgctcatat  ttaaaattat  tggtttatta  atgcaccatc  acatgttatc  atgtgatact   49920
ctgaattctc  ttttttgcata  gacaaatcag  agattacctg  ctgcaagtca  ttagtcatca   49980
ttaacctgta  ctgaaatggt  tagagcctag  gggagttcca  ggtaaaagga  ccagtaatga   50040
gtagaagctt  gttagatgta  gagatattga  ggacagagat  aggtgcttta  taaatatcaa   50100
tttgatataa  ttttagcata  aaaataagcc  tatgatgctc  tttgagcttg  ggagtagaag   50160
tggatatgta  attttcaggg  cgtagtataa  aatggaaatg  cacactcctt  gtttgaaaat   50220
tattaacgat  tttacaaggg  tgacaacaga  gcattgaagc  aagtgctctg  tgagcatgaa   50280
gccctgtgtg  aaatacacac  ctgtgaagct  ggccttgcct  gccaaacagg  aatgctggta   50340
ctgttaatca  aacagaaagt  tcagaatgac  aatctgactt  ttttttgtag  aagatactaa   50400
acttttggcc  ttgaatatct  gaatttaaga  tactggtatc  aagccaaaag  aaatttgggc   50460
ttagaacttg  aaagatttaa  acttgtgctt  tgacttgtgt  gctcacagct  ctctgtgtca   50520
caattttttt  catctgtact  tcgggacaac  aatagtgtgt  cgacatcaca  aaggttttgg   50580
gaggattaag  taggtgaata  catatgaagt  tcttaaaaga  atgtctggca  ctgagtgagt   50640
gctacctcgg  ttttggcatc  gttattgtgg  tcattgctat  tgttattatg  acttgaagtc   50700
atattagtgt  atgaaatccc  atccatgaat  agaagacaga  agaactttg  gcagggttt   50760 ggaggtaaaa  gaagacattg  taaaggagat  gggtaaagga  atgattttaa  agactgagaa   50820
taattagggg  agtacgatgt  catggaaatt  aagggatgat  aagcaccaat  taagttgtta   50880
ttggactttt  ttcttttgaat  ggttcaaatt  cagaataata  aggaaagaag  tctgattata   50940
cgaaattaaa  gggtagggtg  actgtggagg  tagtgggagt  tgacttttct  gctaataagt   51000
ttagaaataa  aggaaaaatg  gtagcttgag  gaaagagagg  agcgattaag  ggaaagtctc   51060
tcgttaactc  ttgttttca  tctctgagga  cagcgcttag  cccaaggcct  gacctgtgat   51120
cattactctc  tcaaggttta  ttccatggac  agagctatct  catttcatgc  ttataacaac   51180
cctacattat  tagaattgtt  ttagagatga  ggaagctgag  acacacacca  aaccagcctt   51240
ccaatttcac  tttgcacaac  tttgaatttc  tttatattc  ttgaataaaa  gttccacttt   51300
ttaacttacc  acttcttagc  agtcattgtc  taactgagta  attgttactt  cattcattta   51360
atggttctca  gattcgcata  atttgaacct  aaatttaatt  ggcctccaag  ctgatgtgct   51420
tacagaaaca  gtgacaggaa  acaaaaatgt  caagggagac  tatgtattat  taagatgata   51480
aatgaaatga  tgtccaagct  gagcaattaa  agtgtgaagt  agaaggacac  agggtgagaa   51540
actgatgctt  ctcctcagcc  tctataaaaa  agatactgaa  taaagataat  tgagaggcat   51600 tagggggacta  gactgagaaa  ggattggaaa  tctgttcact  gagagtacag  aaatgaggaa   51660
gcttggaagg  cagaagattt  tggtcaaaga  cgtctggctt  gaagctattt  cagctctttg   51720
gattatctgt  ggtggaggcc  atcacgtctt  tggagtggag  gtaccatgaa  actagtgtct   51780 gcaaacatc  atctaaatga  aagcaaaatt  cctgagaagg  atggcactat  aattttaaa   51840 agaaaagcta  tgagttaagc  attcatatca  aggtagatgt  ttggagtgta  ttgcttgtgt   51900
gtgaaaaggc  agagatgacc  agaataagag  ttagaggtat  gctgcgtttt  cttcttggtt   51960
gatgagtagg  atggcctgga  caagaagtg  acctctagta  aaataccttc  atagtgtcaa   52020
atcatctgga  ggaaattcag  attaaagagg  ttggatgatg  tcgtaattaa  gatcctgggc   52080
```

```
ttttaaggtg acacatttta tattcaagtc ccaggcccaa tgcatattag ctctgttact   52140
tgagctttta tttctgcatc tttaaagttt ggcaaaccta ttacatgaag ctgttgaggg   52200
gataaatgaa ataacgcatg caaagcactt gcagtaaaga ctaattatca atattttatt   52260
tgttaagagg cagcattgcg ttttactggt caagtatgta gactctgggg tgaaacatat   52320
ttggtttggt ttcatctctg caatttatag tttgtgtaga ctttgagaat agttctcaat   52380
cattctaacc ctcagtgaat tcatcttcta atgggagtga tatcagtatg gatttcatga   52440
gattatgaaa agaaaatgcc tacaaagtat ttattacaat gcctggcaca gaacaagctc   52500
tccttaattg taaaaatgct aactcttatt cttcataata aataaaagta attaatgtta   52560
tagaaaacaa aatcaaggat actgatttat atttggatta cttgatttat attttgtcag   52620
tctataactg gtcttaacta aggtaagtat taagatctca ttttttaacag cgagtattct   52680 tttgatttta gttcattgga aatcctggga ttcagaaatg tggattaaaa gtaatttctt   52740
ctattgtaca ttttcctgat gcattagaga tgttatccct ggaaggtgct atggattcag   52800
tgcttcacac actgcagatg tatccagatg accaaggtca gtacaatttg aattcaggat   52860
ttagaataga tttttgtagg gcattagctg gtgactggat gtctttaaat attttttcttc   52920 agttttgaga tttaaaacaa ttctttttttt ttattttcct agaaattcag tgtctgggtt   52980
taagtcttat aggatacttg attacaaaga agaatgtgtt cataggaact ggacatctgc   53040
tggcaaaaat tctggtttcc agcttatacc gatttaagga tgttgctgaa atacagacta   53100
aagtatgtgc attatcttgg aaagaatttg ggaacttgtg cgaatttcac ttttggagca   53160
gtttgtgtaa ttcccacttt gcatgaatgg ggtattctag ttaatggaaa accatttatc   53220
cttttgtagt attttaatta tacaagcaaa gaaaattgga ttgaatctct aaagatccag   53280
tgtttcatta tgaaatctct aaagtcagca tggttattca ccatttatct tgcccataaa   53340
agttcagaga atgtgctaag aaatcccagc tagctgagtt tattcgctta gattttagat   53400
aaatagaatt tataaatatt ccaaagtttg tcactctctg ggtttttattg caggttgctt   53460 acctttagta attttgcttg ttgatttttt tccttgcagt gaaaaaatgt ttttaacatt   53520
tttcatcaag caaaatttaa aacatgatat ataataactg tctttgtaag gaattcaaga   53580
tactggccta gagttagttc acgggagatt aagaataaat ttgttttgtt ttgttttttta   53640 attgtagcaa aacaaatagt ttttcttcaa gagtttctgc cttggttgtg gagtttgcaa   53700
ctttcataaa ctacaaagga attttttttt tttttttgga gacagggtct cactctgtca   53760
cccaggctgg agtgtagtgg cagatttcag ctcactacaa cagctgcttc ccgagctcaa   53820
gtgattctct tgcctcagcc tcctgagtag ctcagactac aggcatgcac tcccatgcct   53880
ggctaatttt tgtatttttt gtagagatga ggtttcacca tatttcccag ctggtctca   53940 aactccctgg tctcaagcaa tctgtcctgc tcagcctccc aaagtgctgg gattacaggt   54000
gtgagccaag gtgcccagct gactcaggaa atatttttg taactggcag cattgaccag   54060
gaataaaaat acctggtctc taatctttgc acagacatta tcagtaaatg agagaatatg   54120
tgtaaagttt tttaaaaaat tataaagtta tgaacataca aaattcttag attaataaca   54180
acaatgtgtt ttataactgc ttttcataat gtgcctcagg ctaggctgat taaaccaaga   54240
taggattgat taaaagtaat cttagggaaa gggaaggatt ttgtgccggt atggaactct   54300
cagttactct ggattaattc atctaggcat aaatttttaga atctctatag tagagttat   54360 gaactaaatc tggcctgcca acatatttta tttgtccagt tcagggtttt gctttgtttt   54420
```

```
ttgagacaga gtctcactct gttgcccagg ctgtagtgca gtggcgcagt ctcagctcac   54480
atcaccctcc gcctcctggg ttcaagcaat tctcctgcct cagcctccct agtagctagg   54540
actacaagta tgcaccacca tgctcagcta atgtttgtat ttttagctga gatggggttt   54600
cgccgtgttg gccaggctgg tctcaaactc ctgacctcaa gtgattcact cacctcggac   54660
tcccaaagtg ttgggattac aggcatgagc cactgcaccc ggccttcagt tcagtgttta   54720
aaagttttta attcgaatga cgtactttct gcacatttgc atggcctgct ctgctgtagc   54780
attcacttgt tttcagagac tctgctctca gaggcaggtg gatcacctgt ccctcagaca   54840
tacataaatt aaggctactt tgcttatcaa atattagtat tcgtagatac tcagcatcat   54900
aagagttcga agtaataatt ttaatattta gatgacgtaa gttaatttaa aattttttg    54960 agatggggtc tcactctatg gcccaggcta gagtgcagtg gcacaatctc ggttcactgc   55020
aacctctgcc tcctgggccc atcctcctgg gtgggctcaa gtgatccacc tcagcctcct   55080
gagtagctgg gactacaggt gcatgcacgg gtaattttaa aatattttt ataggcacaa    55140 gattttgcca tattgtgcag gctggtcttg aattcctggg ctcaagcaat cccacagtgc   55200
tgagattaca ggtgtgagcc atggtgtcta gccaattta ttaatatgta atattagagg    55260
taataaaaca ttaaaaagtt aagatgatcc ttggtggctt tacccaaccct aaataatact  55320 aaagtcaaaa gcccaatctt tcattaaaac atcacatgag tgaagaggac agactctggg   55380
gatgtgctta aggtggttct aaaaaagtaa cggtgttctt tataaataac ttattattag   55440
aatgtaatcc tcagagtgcc ctcagcgctt ctcaactaca ctcaacataa atgaaatcta   55500
ggagtccaca ctagccttc tgagataaac atttcggaag acagcgcaaa aagctggggg    55560
atatgctagg ctctctagag aacctactgt tcaatattat aatacaaatt tttactctat   55620
tgacctgttt ggatgtgtag ttctgctgat ccaaccgctt taatcctgtt taatatctgg   55680
gtttcatcct ataactatgg ctttagacaa gcatctttga aaccaaatt tgagggtatt    55740 agttctttt cctgctttgc tactgaatgg tttgttaact agcatttat tctctgtgcc     55800 tgctatattt cttagtcatg agagagagag ggagtattta tttacaggat aaatacttta   55860
aagcaccaac ccaatatatc tatagttaaa tgaacatcct aggtattgtt tcatatacaa   55920
actctctctg ctttatactg tttattcatt ttgcctgtaa ttgcttattt tattattttt   55980
tttcttatac ttttagggat ttcagacaat cttagcaatc ctcaaattgt cagcatcttt   56040
ttctaagctg ctggtgcatc attcatttga cttagtaata ttccatcaaa tgtcttccaa   56100
tatcatggaa caaaggatc aacaggtaca gtgttttca cttgcatcct aaatgttatg     56160
tatttatctg actctaattc tcatttccac tcttttagt ttctaaacct ctgttgcaag    56220
tgttttgcaa aagtagctat ggatgattac ttaaaaaatg tgatgctaga gagagcgtgt   56280
gatcagaata acagcatcat ggttgaatgc ttgcttctat tgggagcaga tgccaatcaa   56340
gcaaaggagg gatcttcttt aatttgtcag gtaaatattc aaggcctcac ttttgtcttt   56400
gctcagtatt cttatagaat gtaagagccc tgccattgtg tatctcttac ttatatcata   56460
ttattcttca ctacagaaat ttaccagttt attgcaattg tttgtgtctt gtagtagatt   56520
tatagaattc cagaagtaat agggtccttt aggtgttatc cagtctaatc tttcatttca   56580
tctgtttact tatcttgtta agttgataaa taacttttca aatgtgtccc ttagtaggca   56640
tctctacaac ttagtctcca gatacactcc acataacaca tagttctaat gttttgataa   56700
ttttttaacc atttttttcc atggttttag tttcttgcc tagaaagttc tcccctgagg    56760
gctaccacac atggctatgc aggctgtgga tggcacactt ttgtcggtgc cattcacagt   56820
```

```
gacatgagtt gctgttggcc aaagttgtgt aacactggtc tttctttcct tctctcttcc   56880
ctcctgaacc atgtaaacat atatctatct gattgttctg ctctcccttc aaaatataat   56940
tcaaattatc tttctttaaa gccctcccca tacctccaaa cctccaaaca aaattaagat   57000
ttacttcttt tgtcagtcta tgaaaatata tacatatctc ttgtatactt ggtgagttgt   57060
gtgaaaataa cagtgtacag tgttcatctt tgtatcattc agaatatcga gctcattgct   57120
ttacatatgg tgtgtattca ataaatacta ggttcattgc ttatatttca gatttgtatt   57180
atttgtataa gtgttagagt ttatactagc attcaggtag cactatgtct attttctaga   57240
aatttaatat ttctaacaaa gcaattatgt agtgatttaa tacacattat taaataatca   57300
ataaagtact atgtttgcca atagtttact ttttaaacct tactgtattt aatatcccta   57360
ctgtatttaa tatcccactt gcctatggat tgaaatcaat ttgttgactg ttaagattaa   57420
gttaatacta attagtaatc aacataaaaa gaaaagaat  ttgtaaccca ttttcatgca   57480
ttacgtttat gaattaaaat cacataaaca atcaattat  ttaaatttag tcaaatttct   57540
tttaagcaag caacaattaa aatagttgct ccgctttact aaagataatt aaattttcc   57600 atcaataatt taatacattt ttactgtgca tcttttgcat gcagattatt gcattaattt   57660
taattgaaaa taccgaagaa ctaaaagaa  acttcccctt ctaagtccac attaaggaaa   57720
caacatacct aaaagcacct gatacaactg tactacattc cccacaggaa atcatttcta   57780
ctattctttc aatttatcca aatctttcta cccaacagga ttttactttt attcctcttt   57840
ccatattctt ttggacttca tatgcttagt tttatctttt cttttttaaaa cgaaatctta   57900 aatccaagga ttatgtatta ggtttaaaga atttatccca gttgtcagag gttatttata   57960
tctagcaaac aataactgct gattaaatct tgtggatgag tttgtcgtat gtaccttatt   58020
tgtgccagag caaaataagg taatcaggac tatttattca tttaccaaga ggttacatat   58080
tgaaggacta tctagagcaa gggtggagtt gtgttagact ttctgcagag aatttgataa   58140
tggaatgtac atgattggta gagaagaata tggaagttta atactgggta tgcaaatgca   58200
tggataaaaa cctcaaggta aaactcatca aatcacagtg gaaaagtat  agtgaagtct   58260 gaataaaaat aataagaggc tgggcatggt ggctcacatc tgtaatccca cactttggg   58320 atgttgaggt gggaggatca cttgagccag gagttcgaga ccaacttgag aaacatagtg   58380
agactccatt tctacaaaac aaaccaacaa gcaaaaaacc atgtatgatg cacacacat   58440 gtagtcctag cttcatgcag ggtggctcat gcctgtaatc ccagggcttt gggaagtcaa   58500
ggcgggagga tcatttgagc ccaggagttc aagaccagcc tgggcaacat agttagaccc   58560
ccatgtctac aaaaagtcaa aaaattagct gggtatggtg gtacctgctt atagtcccag   58620
ctacttggga gtctgaggtg ggaggatgac ttgagcctgg gaggttgagg ctgcagttag   58680
ctgagattgc accattgcac tccagcctag gcaacagagc cagaccctgt taaaataaaa   58740
taaaataaaa taaaataaaa taaaataaaa taatataata aggctgaggt gggaggatca   58800
cttgagccta ggaggtcaag gctgcaggag ctaagattgt gccactgtac agcagccttg   58860
gtgacagagg gagactctgt ctcaaaacca accggtcggg tgcggtggct cacgcctgta   58920
atcccagcac tttgggaggc cgaggtgggt ggatcatgag gtcaggagat cgagaccatc   58980
ctggctaacc cggtgaaacc ttgtttctac taaaaaaata caaaaaatta gccaggcgtg   59040
gtggcaggtg cctgtagtcc cagctacttg ggaggctgag gcaggagaat ggcgtgaacc   59100
tggaaggcgg agcttgcagt gagcctagat cgcgccactg cactgcagcc tgggcgacag   59160
```

```
agtgagactc cgtctcaaaa aaaaaaaaaa caaaaaacga accaaccaac caaccaacaa    59220
aacaaacaaa caaaaaacca acaaaaccaa acacttctat catgctcatt accacctggg    59280
cactgctcca aatactttac acaatttaat ccttacgaca acctacgaaa aggtccagta    59340
ggttctaatg ttattcccat tgtgcaagtg agaagctgag gcactgaggg tttaaataac    59400
ttgcctaaga acaagctcct ggtaacagtg tgaaatctgc ctccacagtg cctgctttaa    59460
tttcttggct acacagcaga ttcatggtag tggtggtagt ggtgttcatt ttctctaaaa    59520
taacagtttg aataatttgg ttttgataat gcactgcatt tattataaat tagatgatca    59580
gagaaagatt gcagggataa gaaattatgc ttttgataat ctttagttat attcttaatt    59640
ttcttcatta ttatttaaat gtaaaaataa atatctgtga gcagtagtat tttcctgtca    59700
tgaagctgaa attactttca taaatatgtg tgaatattct aaagagaatg actctgtagg    59760
atttaaagaa attaattctt atttttgctg gcatttattt attttatcag attcactttc    59820
tcatatatgt ctctcttcat ggcaccatat gcctaaagtc agcttggata gtttggatcc    59880
tccaaggaaa attccttcca caaacatgtg cagcacacag tgctagataa ttaatagaga    59940
atataaaatg ggtttcctgt ttcaagatgg tttgtaggtc tgtatgtgta gggcattgac    60000
aagagagtaa aacataaatc acctagtac aaagtaagga gtgaatggca tatcttagag    60060
aaaaaaaagt tactgggcta aagagaagg catttgtgag ttttcccte cctccccgct    60120 tcccttccct tcccttccct tccctccct tcccttccct tcccttccct tcccttccct    60180
tcccttccct tcccttctct tccctccccc cccttctct tccctcccct ccccctccccct    60240 ccctccccc cccttctcct ttctcttccc cttccccttc ctcttcccct tcccttctc    60300 cttccttcct tccttccttc ctcttccacc tgccttcctt ttaattttgc tatgagccct    60360
taaagaggat tttagtaatt tgctacttaa attaaatata tttgctagat gttgtgctag    60420
gcttcaggaa tacaagttgg attgcagtaa tgtaaagccc tttgcattct agcaagaaaa    60480
cagatgggta tgtatgtttg ctcagtgcta cattaaatga aatggatggg agccgggagg    60540
agaaatggtg tgtttggcct gagaggttag tagcaaggac ttctctgcaa gaaagtttga    60600
agccaattct tcaagaatga acacctttt gctgggtgaa aagtagagga aggcatttgg    60660
ggtaatagaa atagcataaa aggtaatgag gtttgaaaaa ttacatgctg tgtttggaag    60720
aatgtcctgg agcagcagcg ttttagaagg ttttttaaaga cgatggtgac ttgatcagag    60780
ctctgtagtg ctttgaggat gggttgaagg tgggcgtact tggagactgg tgggcattta    60840
attggtgcct tccaaccaca taatgaatg tcccctcaaa tcccttggaa acactttaat    60900
tctagaaaat tcaaaaattg tccccaacat ctttttcctc tgagttggta ccctggatct    60960
ttgggtcttc ttttctttcc ttttttgatg ttttattttg ggtaatgaaa gtcacacagg    61020
ttttgaagcc agcagatttg gcttcaaatc caagtctcag ttgcttgcta gctgtaaggg    61080
acaaattata tatcttttct aaatactcat ctataaatg ggagtaataa ttgctatggc    61140
ataggatttt tttaaaaaaa agattagaaa tcatgtgtgt acagaattta gcacagtaac    61200
tgatggatat tatttctatt acctgttatc ttggtcttct agttgatagc tccttgctag    61260
cgtctagctc ctttccatag ctcttcctga gtagggccag catgcagtgc cacagcttgc    61320
taaggcttct cctggattgc tgagttgttc tagttttgt ggcacctcac atgctaaccc    61380
accctgaaca catgctctga aaacataaca tttagaggaa ggttgaagac tgagagacaa    61440
ggtatatctt tgaggaaatt cagatgcttg tcttgaggag ctcaggaaag ctagacacga    61500
gtaatgactg tcgtttgtgt gtggcattaa taaattttac aatagctatg tccccattta    61560
```

```
gttattctat gtcacaaata aaggcaggac agtagtattt actgtgttaa ggtactggtt    61620
tcccaggtat cttacagtga gaagacagaa gctcagaaag tgtaagcaat gtgcatattt    61680
ggtggagtct ggatgtaaac agagatcttg atgccaagcc tgtggagctt tgtctccata    61740
taatgttgtc tctttcataa taactgactg tcatgtggca gattattcat gctattctga    61800
cattgatggc attaatatca tcttattttc ccaatctatt caaggatcag ttttgcctta    61860
ttttattttg tttcattcca aattggagat gtagagaaaa atcacatgaa gtttgatttg    61920
ccagtctcct aaaaggaaga aaaatgtaga tttttaatat acttaatttt ttttctttaa    61980
taggtatgtg agaaagagag cagtcccaaa ttggtggaac tcttactgaa tagtggatct    62040
cgtgaacaag atgtacgaaa agcgttgacg ataagcattg ggaaggtgaa cagccagatc    62100
atcagcttgc tcttaaggag gctggccctg gatgtggcca acaatagcat ttgccttgga    62160
ggattttgta taggaaaagt tgaaccttct tggcttggtc ctttatttcc agataagact    62220
tctaatttaa ggaaacaaac aagtaagtaa caaggagaat attttttaca attcttatt     62280 ttaatagtat tttttaagt cactagtctt ttagtggtta ttcatgccag tttgagggac    62340
cttaagccaa agatattgca aaggtttgga tttttttttt ttttggctat gaaatacttc    62400
aaaatgacat ttaagttctt tatgagatag caaatagtta tttataaaaa tagagcaaaa    62460
tagtggaagc tttttgaagg ggtactttt aatatatatt ttttattatt aaagtaagat    62520
atccctgttt ttaaaggaaa tataaaatta taaaaaagaa aataaaaata acttatttta    62580
tctcttataa gtaattaata tggatatttt tcctaacttt ttatatgctt acatgtacct    62640
atgcattcaa atgtatgtaa aagcatacac acatatttat ttggcatttt taacttagaa    62700
tatactttat atttcaattg ataatgcatt ttctttatac tttcaagctc atgtgtattt    62760
tgtacatatt atgtgtattg atggtaagtt accatcttct gacactattt ttatcttttg    62820
agctctctca tttgttcaca ctaaatgtgt ttttagcgtg aaagctccca gctttccctg    62880
tgttaactta gtcccatgcc catctccttc cccatggtca tcaaactcca tgaatcaaca    62940
ccttaaggac catcttgcaa gtaacatgtt tgcttctctc attttatga tgcactcact     63000 agcaaaacac cagttttggt cagtctacca gtctactttt tccctcagtt tcaccaagaa    63060
aactgagtgc tgctagagaa aagtacccat ccatgcaatt tggtgccttt atacatcaag    63120
gtttccaacc gctcagtagg ctccaaaagt tccaatcagg ctgaattttc ctcggtttct    63180
caaacacttc gtgtacccct acttccagtc ttttccagt gttactctct ctctacctag     63240
ctctaaattc tctcttcacc tggctgtctc ttcattcttc ctgtctcagt gctatcacca    63300
gtctggaagg ttctcttaca tgaccctata gcactttatt tctcacatat actaccattc    63360
accacattat ataatttaat ttttcatttt tataatctac ttttggtaa attgttagta     63420 ccatgaagtc aatgtcaatt ttgttcatgg ttgtaacctt accattgata ctagtgtttt    63480
gcacatagta gattatcatt tagaattaag tattcaatat tggcaaaaaa taaaaattgt    63540
gtaatacatt atgttgataa gcatgtgtgg aaacatgctt catatattga tatgaattta    63600
aattgtcctc ttttgaggac aatttggcaa tatctactaa tattttaat atatgtacat    63660 acttttttga cctcacaatg tactgttagg aatctatgat acagacattc tcaatgtgca    63720
caaaaattat gtacaaaaat gcacattaaa acattgttta taatagcaaa agagtaggaa    63780
aaaaacctaa gtattcccca aaaggaacta ttcaaataaa taatggtaca tacatgttgt    63840
ggaatgcttt gcaatcattg aggaaaaaaa aacgtggagc aaatttaatg tcctgataaa    63900
```

```
gattacatta ctccgtggca aaaaaaaggg cacagacagt gttttttacta tgctaatgtt    63960 gatgaaaatg caactggaat atgatagtta taaaagtttg aatatgaaat aaaaccctcc    64020
agaaatgggt tccctggttg tctctgggtc tttggaaatt actgagacat ggttagatcc    64080
catgtttcat tacttaaact agtcttatgc caaaaacctg cttactttaa tcttcaatat    64140
ccgatggaga ggaattgtgg gcccattgga gagggacaga gggagattta tcattcacta    64200
tattctcttt gttctgtctg gagttttttac cattgacaca tcttacccag ttaaaaaaac    64260
atagaattgt catttgatta attggagggt ataaccatga tttcactggc agctggtctg    64320
agtaaagaac actttgggtc atagctttca aacattttttc aggtagtatt tgcctaagtg    64380
acatatttgt gtgtgagctc atcctaccgg gcttcgggat aatttcccat atcataacat    64440
attactctgg aaaaaggaac catttgggta tatgggtata gtgtaagcca tagtatcagt    64500
tgccttcttg gggtttatca tatgggtcca ccacatattt acagtaggaa tagatgtaga    64560
tacatgagca tacttcactc tgctactata attattgcta ttcctactgt tgtcaaagtc    64620
ttttagctga ttatctacac ttcacagggg taatatcaaa tgatccccca ccatgctctg    64680
agccccaggg tttattttcc tttttacagt aggaggccta accagcattg tattagccaa    64740
ctcatcactg gatattgtac tacatgatac agcagtatca tgtagtaata tttgaagtca    64800
ttacagtagt aatatttgaa gaaatcttcc tggctgtatg tagaacaatg aggactcagc    64860
caacttattc ttcatagtag agctaataca taatgtaatg aagttgtgag aagaatgtta    64920
actttgaaat tccatcaggt ttcccaatag tcataatgaa tcactcagca aactttataa    64980
aaataacaag atcctttatt tagcagttta tgtgttctat gcattgtgct aaacatttta    65040
tatgcatcat ttcaattact cttttttcatc accatatact gtatttatta tcatcttcat    65100
tttccaggtg aggacactga tacccaggga gctcatataa ctcacaaatg gcatttctat    65160
gacttgaaca caggcctgtc tggcttcaaa gcctaggcct tttcctgaat aaagttagtt    65220
ccatagagat tcagttttgc tgtctacatg aaagcattgt gtacatggtt atgttttttt    65280
aaaaaatata tgatctgcca cctgttaatt attcaggatc actagtgtaa ggtgactttg    65340
aaaggaaaaa tagaaatatt ctccagaagc atagcaatac gtaagaactt tggtcctatg    65400
tatgtttatt tttgcataat tgttgatttc taagttgctg gtgtatctct tattttcaga    65460
tatagcatct acactagcaa gaatggtgat cagatatcag atgaaaagtg ctgtggaaga    65520
aggaacagcc tcaggcagcg atggaaattt ttctgaagat gtgctgtcta aatttgatga    65580
atggaccttt attcctgact cttctatgga cagtgtgttt gctcaaagtg atgacctgga    65640
tagtgaaggt atttattata aaaaaaaacc ctttatgctt tatatttaca cactgacatt    65700
gaacaatagg acccaagaca aaaacctgac ctaaatcatc tggaaaaact tgagtagaaa    65760
tgtgtttatt atcgcaaaca gttaagtttta ctaattttgg ttaaagtgat gggtcaagga    65820
agtgtgtctc tgtgcttcta aatgttatac taattggtta atggttaata ttccaggaaa    65880
caaactctga ctagactgga acgagattcc acgctctgtc attgactaga tcctttcgtg    65940
gcttgtgtaa gccccttaac cttgttaaag gtagtaatgt cgactttgca gggttataca    66000
taataattag aaaaaatgta tgtaaaatgt ctgcaacaat gcttggcaaa caggaagcgc    66060
ttaataaaaa aggtttttat ctttactata gcttaaaaca atattaatat tttaatagct    66120
cacttgagat aactttttaa aaaattaata tggtgaaata tataatgaca atgattaggg    66180
ctgatgtatt tagcattagc agtttggtaa aaatggagtg aggggctttc ttattaatat    66240
agtatgattg aaaacactgg gtgatagaat aaggatattt gagagggcaa aaaatgagag    66300
```

```
ttgttccaaa atattgtgtc tcaagtcaaa ccatttttaa aaatcaagtg tagtgattta    66360
tatacatata taatttatat aaaataaaat gcattcactt taagtatata ttttcatgcg    66420
ctttgaaaat taacatattc atgtggtcat tgtcgctatt aagttatgca atattttcat    66480
tatccaaaaa agtttcttca tgcctcttca ctgaaaacat ccccttcccc tggcccccct    66540
gacccttagc aatcatttgc ttcctgacaa tgtagattaa tgttttctct agttttatat    66600
acataggatc atacagtgag tactcttttg tgtctgtttt ccaaaatgat tgtactatgt    66660
tctaccccca ccagcagtac atgagcattc tggttgctct acatccttgt cagtacttgg    66720
tattttcaag ttacttttag ctgttctagt ggaggtttaa ttcatttaga tgtaattttc    66780
atttccctga tgactaatta tgtagaggat gttttcatgt tcttattggc cattcttatt    66840
tttgtgtgaa gtgttgaagt attttgcttt taattgggtt gtcttattat ataagagttc    66900
tttgtatatt ctagatagaa gttgtgacag gtatatgtat tgcatatttt tttcccagtc    66960
atagcttgtc ttttcatttt actaattcta tttttaacaa aacagaggtt ttaaatcttg    67020
gtgaaatgca gttttccagt tttttttcttt tatggtttgt gcttttttgta tcccacttaa    67080 gaaaccttt cttagcctaa atttgtgaat attttctccc atattttctc ttagaagtgt    67140
taaaatctca gctttggcat ttaggtctaa aacatttaa gttgattttt gtgtgtggtg    67200
tgtcaatgaa gagttgacat ttatttcttt ctgtatggat atccagttgt tccaacatta    67260
cttgttgaaa atattatata attcctcatt gaattaatgg aagctttgtt ctctttaatt    67320
gactatttag gtatggttct attttagcat tatttattct gtgccactga tttatacctt    67380
attcttatgc caataccaca ctgtcttgat tactctagct taatagcagt tcttgaaatc    67440
agatagtgta agtcctctgg tgttcttta aaaaaaattg ttcttattat tctaggttct    67500
ttgcatttcc atataaattt ttaatcaact aactttatgc tgggattttt attgtaatta    67560
agtccatatt tagattttat atagaattta tttataaatt aaatcatatt acctatgatt    67620
ttaatgtaat ctataatata taattaatac ataaataata atttatatag attatatcta    67680
taaattaatt tgagggaact aatatatatat aatgagtct tttgacatat taatgtgata    67740
tatagttcaa ttagtctttt aaaatttcta acagtgtgtt gtattggatg ttttctgata    67800
ctattataga tggtattgta tttgaattct aatttccagt agttcactgt tgatatatag    67860
aaacataatt catttatttg tacatgaatt ttgtatcctg taaacttact aagctcactt    67920
acgtgttcca gtaccttatt atagattcta caggattttc tttgttcaca attataccat    67980
ttggtaataa agacagattt gcttttctt ttctaatatt tatgtcttct tttttttct    68040 tgtcctattg cactggctag gacctccagt actatgttga atagaattgg tcagactggg    68100
catcattccc tggtttccaa acttagagga aaaacataca gtctctaatc actaattatg    68160
acattatctg tagttttca tagatgccct tcatcaaatt gaagaagctt cttcctagtc    68220 attttggag agccttttt tatcattaat aggtgttgaa aaatgctctt cagcatctgc    68280
tgaggtattc atatttttca cctttatttt gttaatatgg tcaaatacac tgactgattt    68340
tctaatgtta aaccaacttg cattcctgga gtaaatctca cttggttatg gtacattatc    68400 cttttatat agtattaaat tttgtttct aaattttgtt aagaattttg catctgtgag    68460
agatattagt ctgtagtttt atacttcctt gtaattatgg gagtaatgct ggcctcttga    68520
aatgaattgg gaagtgtttc ccattccaca attttctgga agaatttgtg taaaggtatt    68580
ttcttcttaa atgtctgata gacttcacca gcaaaggcca tctaggtttt aaattttgt    68640
```

```
gaggaggaga tttagaatta tgaatttaat aactttgata gatgtatgat tattttaatt    68700 ttctttact tcttaagtca gttttagtaa tgtgtaactt tcaaggaata tgcccatttc     68760
atataagttg ccaaatttat ttgtttaatg ttacttatag caattattta attatcctgt    68820
tagtgattta attatcctgt taatctcttc aaagaatcag attttttgtta tattgatttt   68880 ctctattgtt tgtgttactt tctcacggac ttttgttctt atctttattg ttccctttc     68940 cttacttatt tttatttaa ttgactcttt ttatagattc ttaatttgga agcttagaac     69000
actggttttt agaaccttct tatttttgtaa cagaaacatt tatttaaggc tgtatatgtc   69060
cttataaata tcactttcac tgcatcccaa tattttgatg tgtcctcttt ctattcattt    69120
aaaaaaattt aatttcccaa atgtccaaca atgatagact ggattaagaa aatgtggcac    69180
atgtacacca tggaatacta tgcagccata aaaaatgatg agttcatgtc ctttgtaggg   69240
acatggatga agctggaaac catcgttctc agcaaactat tgcaaggaca aaaaaccaaa    69300
caccgcatgt tctcactcat aggtgggaat tgaacaatga gaacacttgg acacaggaag   69360
gggaacatca cacaccaggg cctgttgtgg ggtggggggga aggggagggg atagcattag   69420
gagatacacc taatgtaaat gaggagttaa tgggtgcagc acaccagcat ggcacatgta    69480
tacatatgta acaaacctgc atgttgtgca tgtgtacccct agaacttaaa gtataataaa    69540
atatatatat atatatataa atttaatttc ctttgtgact tctttgattc acgagttatt    69600
tagaaggctg tcatttattt tccaaatatt tggagatttt ctggataact ttctggttat    69660
tggtttcagt ttgactttt tgtgctcaga taacctactc tgatgatttc tatccttta     69720 tatttattga aacatgcttt atggattatc atatggtctg tcttggtgat gtgccatgtg    69780
caactgaaaa gaaagtatat tcagctgtta ttgggtcaaa tcataggcc aaattgtttg    69840 gtaggatttc tcaagttttc tgtgacttca ctgacttttc tttctattta ttgtatttga   69900
tagagaaata ttgaagttgt aattgaggat ttgttggttg cctttcagt tttatctgtt    69960 tatgctttgt atattttgaa gctctgttgt ttgttgtgca aacattaagg actatataac    70020
aaaggactat atataaaaat aatttttaa ataaagtaac cactttatat taatctaagt    70080
ttgcagttag tatcatttc ttcctctgga agaattccct tttacatttc tagcgcagat    70140
cttccagaaa cccatatgca gattactgga gcacttttc cataactgcc ccagaactcc    70200
cagctatctc agtctccata aatgttgatc tctatctcct catctcagga aagccatgag   70260
actgtttaaa tttcttctta tgtatatggc ccttaatttg tctctaagca gaaggccaga   70320
gtgatcatag ggctcacata atttgttcc cttctttcgg gtattacata gtcctatgct    70380
gtctgttgcc cagtgtctgt atccagtcat ttaatatatt tatccagttt tcttgttgtt   70440
tatgtgagta ggttaagttc acatttgtta ctctatcatg cctgaaagaa ctctcttcaa   70500 gtattttca agaaacatt agaaatttta acataaaata attataaaat gcactatgct     70560
gcttgtacaa ataatgtgct aatagacatt tcacacacat ataaagtggg ataattatga   70620
taatttaata atctttataa ttatgtaatt gttactaaat tataaattat attttattaa   70680
aattcttaag cattaaaata atttaaacta tagaattaat taaactttag caatgaacca   70740
ggcaggaact gttatatca ggatttatac tgaatattat aagggtggta tttggatata    70800
cagattttat aatttggttt tgacataaaa tgaattcttt ctttttctaa gataaagagt   70860 agggaattt aaaatcataa ttaattttc acaaatgcat tcacattatt tatctttaat     70920 atgattttt tattgatctt tgtttctttg taaatttatt atttttgaaag tactgccttt    70980 tccttatttt ataaaacaat tattgccagc caaatttatt gtgtttattt taataccatt    71040
```

```
ccataaaaga aaccatgaaa catgaaattc aaatagaaat ttattaaaaa ttgctgactg   71100
ttaaataatt tgtgtgatta caacatttaa agcaagattt gaaaaattta taagaaaaat   71160
tcagggagtt aatccactct ctttcctatg ctgctagacc ctattccagc ggtctccata   71220
aaaaaaattc agagaaacag aaagcagtaa cagtgatcag attgcataca aactttctgc   71280
acacacatat atttgttata acttatgtaa ccgttgattg atttggcttt ttcctgctgg   71340
actatgagct cctctgagga atagatttat tttttttctg catatcagta tcccgtgctt   71400
acccagtgtc tagtctgtaa cagccattct ataaatattt atgggtgaag aaaaatgttg   71460
ttgaattttt aaagtgaaaa accaacatgg cttatcatct ctattttaaa gattttacaa   71520
agggaatgga ctgtgaaatt tccattaata aaaataggtc taatcttcca tgattgaact   71580
atgatagaag gatcttatga ttgagtaagc ttttttgtatt caccttcatg ttattttatc   71640
attttcaaaa taggaagtga aggctcattt cttgtgaaaa agaaatctaa ttcaattagt   71700
gtaggagaat tttaccgaga tgccgtatta cagcgttgct caccaaaattt gcaaagacat   71760 tccaattcct tggtaagtta aattgtgcaa ttgtgattat gttgtgtttt gctgctgaca   71820
ttctcttgat aactaaaatt tatgccaaag ctaggaacaa ttggtaggga tttccctgat   71880
gtatgaaaac tataattttg agatttttat atatgtaata gatatgaaaa catattagat   71940
gtaaattatg ctcaattcac atttgtagtc ttttgagtat gcagggtatg aattttttgg   72000
ggcacatata tatatatata tatacttaca gtacacttca agatggtttt cttctttctt   72060
ttcagaactc catgtctgaa aagagcccag gctagacctc tacctaatgg tgtgggttgg   72120
tcccatgaac actttagcta gaaatctgat agtgatttct aagaaaccag acagaagtct   72180
gaaggacact gaacaagatg gagtagcata atataattca ttgttcatct atctatctat   72240
catctatcta tctatctatc tatctatcta tctatctatc tatctatcat ctatctatca   72300
atcatctatc tattttggtg tattgaaagt catttaattt tttagatacc tttattatta   72360
tttcaacctc ttgtctgttt tggaactatg gaaggactat ggcatatttg catgaggagt   72420
ctgataattc tagttgagga aattgggagc caccttattc tcaggttcac tttgaaagac   72480
ctgttctaac ctattctcca attttgatta tagctgagta ctaaaaatat gagggttgtt   72540
ttgtgttaat tctagatctt aagatggggtg aaatgaatga ctgtagttga atcggttaaa   72600
ttagctgtca gtctttatat gctctttcga atttatatat aaatttagtt ataaaaagta   72660
gtttggttaa tgagaaatta tatggatata gcttttcac tcaaccttc tgttttcag   72720 tttccttata tttaaaacaa aggagaaaga gtagatgctt tctaaggtca tttgagcact   72780
gaactggagt tttcttttat cctcataatt gggttcttag ttttttacttg cctattttt   72840 cccataatta taaataccat taaccctatt aaaatttcat ggttccttcc ttataaaaat   72900
gtcctcttct ccaataaatg acagcaattt tattataaat tatttttaa taggggccca   72960 tttttgatca tgaagattta ctgaagcgaa aagaaaaat attatcttca gatgattcac   73020
tcagtaagta tttggatgta atcataagta aatagatatt ttgggcagaa tgcagtgttt   73080
ggttgaattt cctccaatta ttcaaatatt cttggtgcca gtttcatctt acataatctt   73140
catatatatt tacctaatga ttccttccat aagctataga aaaatgaaac atacatttaa   73200
aaatttacct ttcttgaata ttatagaaca cattagtctt tttttttaca agttttctga   73260
aatgtaaata acacctccac caaggccact cttcatcctc tcctccagtt ttctttcttt   73320
cttttttttt tcacaccact tacaccacct gattaaatgc tttttattta ctgttcatct   73380
```

```
ctgccactgg aatgtaaact ccatagtttg gttttctact gaatcttcag tgccttgaag   73440
aaagcctgat tgctaggagg tgctcactaa acttttacta catgaattta aattatttgc   73500
ttatatttcc attgtttgtt tgttttgac aaaagggtca tcaaaacttc aatcccatat    73560
gaggcattca gacagcattt cttctctggc ttctgagaga gaatatatta catcactaga   73620
cctttcagca aatgaactaa gagatattga tgccctaagc cagaaatgct gtataagtgt   73680
tcatttggag catcttgaaa agctggagct tcaccagaat gcactcacga gcttccaca   73740 acagctatgt gaagtaaatt taatttatcc ttgtaacttt caagacattt gaagagcttt   73800
tgtatttata tctaatttgc ataattaagt cgtttaaaag aacattctac ttttgtgtca   73860
ctgggtgata agtccccgt gcctctggtt tttgcacaca tatcttagtc tgtgtgatgt    73920
tcaggagcat ctttgagggc aggcaatgga aacagatctg attagaaagg aattccaggt   73980
tctgtacgga gtacatgtta aagtctgtca agtgtatatt gattatactt taatcattta   74040
attcaagtaa gacaacttca acaatttaaa ttagattagg taaactagaa ttagacctgg   74100
tttggtagta ctggctctga ctcagctacc aactgtgtga caatatgaac atgtcactcc   74160
gcctgctcta atccttcatt ttctcatctg tgaaatagag attcaactaa atgattactg   74220
aaagtttttt tttcagttta aaataatgtg taacttaaag attttttttct ttttggtcaa   74280 agttcctgtc ttgtaagaat taaagtataa catagtttgt tgataggata gctctctgaa   74340
aattgacttt gctcaccatt tgtatgtact acagatcaaa atagttttga aagccaaaga   74400
agatatcata aaagttaaaa ttattttaat gcaaatgttt aaattgttaa attctcaagg   74460
ctgggcatgg tgactcatgc ctataatccc agcactttgg gaggctgagg cgggtggatc   74520 ttttttgagtt caggagttca agaccagctt aagcatcagc aaaatcctgt ctctaccaaa    74580
aatatgaaaa attagccagg tgtggtgggg tgcacctgtg gtcccagcta cttgggatgc   74640
tgaggtggga ggattgcctg atcctgggag gcagaggttg cagtgagcca agatcgcacc   74700
actgtactct agcctgggca acagagtgag accctgtctc aaaaaaaaaa aagtcttgtt   74760
gcaaatgcat tccccctttt ttaagcctaa aaaattaatc ataattttga gatgttttaa   74820
aggcaacatt acataaattt taagtatatt taagggatgt ttttttctcta aagtttttat   74880 atctggagac agagagaaga aagaaaggtg acccactcct ccagccatgc cctaatgtct   74940
aaaatgtgtc tttctctctt ctccacttct ttgccttgct aaatacttca agccacccag   75000
ggctcaattt aactgtcact tcatcactct ctgcttctct tcctttttcc ttctaccctc   75060
cagccaacct accccaccctag cctccatgtc cataacacct gatgcttttcc acctaattct   75120 cattcggtca tccaatttga tttaaaatac ctttgccccc actagactgt gaactctttg   75180
aggacaggac ttgtttcagg cttgtttctg tctattccca gtgcctagtg agatctgaca   75240
tatggtagaa gtttagtact tactgaattg atttgtggag gaataaatgt ctgaaacttg   75300
gtaatccttc aattaatatt tgttaaatga gcaagcaaaa taattttggg atttagtcta   75360
gttaaaacaa agagaattgg aagagactgt gacaaggtga gacatgccgg cattcaatga   75420
ctggacaagc tcagaaccct tctttaggga aatttcaaaa tgacaccatt agatggcact   75480
ttgtttgttt gtttgttatt gtcaaagggt ctcatctatg ttccttttat aggaacattt   75540
cctgattaaa ccttgggaat aatttttaaaa tctttacttc agaataagtt aatgagggtc   75600
tgaaacaaaa gcaggaattt tgaaacaact tctgggcta agagtggtta ataagcctct   75660
ataatgatat caaactctag agtttctcgt gtggataaat atattgataa ataaagaaga   75720
ccatagagaa gtgattgatt ttggtatttt agctctttga gagtattacg tacctaagtt   75780
```

```
ttaaaaaatt gacataatgt gtaagtaggg gtttgctatt atcattataa aattagaaat    75840
tgcttaaaaa tagaaagtag aaatttgaaa caaaaagttt cgtaaaaaac aggaggttct    75900
aaaatgaaac acattataag taactatttt tatagttaaa tcttaaatat atcaaaatat    75960
gtaaaatttc tgacagcatt taaaacatat tcccaggatt atattgtact ttttgttaaa    76020
tcattaattc aaatatttgt tgaggcgtat tctgcttcca ttttgctctt tctggaaata    76080
atttacaaaa aagctgaagg aagctttcaa ctctatttt gtgaacctgc ttttacaat     76140 ctacctgttg taattttcct ggttttaccc atgctacaag cagagacgat tgggccaatt    76200
agtatactga aattctgttg tggattgtgt tttcaacttt ttgaaaattc ttgatggttc    76260
tagttaccag aggtgtgtaa ggcagaaata ttagctagac ttaagttcct cagatggttc    76320
actttagaat tttaaactat tgtcttttca gactctgaag agtttgacac atttggactt    76380
gcacagtaat aaatttacat catttccttc ttatttgttg aaaatgagtt gtattgctaa    76440
tcttgatgtc tctcgaaatg acattggacc ctcagtggtt ttagatccta cagtgaaatg    76500
tccaactctg aaacagttta acctgtcata taaccagctg tcttttgtac ctgagaacct    76560
cactgatgtg gtagagaaac tggagcagct cattttagaa gggtaagaaa gagctcatta    76620
aaaataaaag ggttgcctaa atatgctgat gttaacaaaa tatgctgaca ttttttatagc   76680 aatgagtttt aacaacatgg tgaaactcca tctctactaa aaatacaaaa attagcccag    76740
cgtggtggtg cgcaccttat aatcccagct actcagaggc tgaggcatga gaatcgcttg    76800
aacccaggag gcggaggtcg cagtgagccg agatcgtgcc attgcactcc agcctgggtg    76860
acagaggcga gactctgtct caaagaaata tatatatata tatatataat atatgtatta    76920
taatatataa tacatatatt atatatattt attatatata ataccctatat attatatata    76980 tactatatat aatacttatt atatatatac tatatataat acttattata tatataataa    77040
aagaccgagg caatgaatat tacaactttt atcaactgac ttacattttt acaactaatt    77100
tttaaattaa tgagtcctct ttgatgctgt tctttgaaag caaattgttt ttgatattt     77160 ttctttaaag catatgaatt tatgcaattt aatcattatc ttgtctcttg tgactagaaa    77220
taaaatatca gggatatgct cccccttgag actgaaggaa ctgaagattt taaaccttag    77280
taagaaccac atttcatccc tatcagagaa cttcttgag gcttgtccta aagtggagag     77340
tttcagtgcc agaatgaatt ttcttggtaa gtgttctgtg tgggtctcct ccttaccagg    77400
ccctctaagt tgtacaagat gagtcatata tggaccctt agttgtggat ttaaaagtgg     77460
catttcagtt taaatattat gctggattta aaaaataaaa ttagcaggtt ggcaataaaa    77520
caaaatgcta taaaactatg aaaagacatg aaagaaacat aaatgcatat tggtaagtga    77580
aagaagccaa tctgaaaagg ctacatacta ttcgttccca actataagac attctggaag    77640
agacaaaatt atgaggacat taaaagatc aatggttgtc aggggttagg ggagggagag    77700
atgaatagat aaaggacaga ggattttag ggcagtgaaa ctgttttgta tactatagag     77760
ggggatatgt gccatggtac acttgtcaaa acccatagaa tgtgcagtat aaagaatgaa    77820
ccctgatgta aactatggac tttgagtgat aatggtgtgt caaatattgg ctcattgatt    77880
ggaacaactg tgccaaacta atgcaaattg ttaataatag gggaaaatgt gtgtgggtg     77940 gtggtggtgg tgagggaaga agggatttat tgaaagtctc tggactgtgt gctcaatttt    78000
cctgtgtatc taaagctgcc ctaaaaatag tctataattt aaaaaaatta tcacattttt    78060
attgtcagag gttaaaatga tagttacttg gcctactgtg tagtaccctg tggttccctt    78120
```

```
tagtcttaaa ctaaacatgc acatggctgc ctgagctggg taaggcatcc tgatactgag    78180
atattgtttt tcatactgaa gtttcttcag caacttttg tatgataaat atgattactc    78240
tttgctgttg ttagaaataa aattaatcat ttaatggttt tcaaattagt gaagttaatg    78300
tatattcatt cagctcttgt gctttgcaag acattataat aatgcaaatt attatcatca    78360
cttttattaa aagttgtaga atcccctgcc ttctcttagc atatgaaata atagaggaaa    78420
ttatgttcat ttgtatccta aatgaacatt ttaattttaa ggaacaaaat acttttatga    78480
caataaacag gaattcccca tattttatct tccttcatag agaatactca catcttgcca    78540
cccatgtgtt tattctatac ctgactcagt aaaataattt ttaattctat ttaatagcag    78600
aatatggctt aactacttat taatagtatt ttaatttgtc agagctttca gaaactaata    78660
atgatcaaag ccatcttaat ttggatagta ttttcctcct tttccgcgcc ctcccttcct    78720
cctaccctcc tgaatattgg ccactttcca accatgatct tgaaactggg gatagagttg    78780
ttgactcact cactagtaag caaagcaaac tcggtctctg tccttaagga acttgtgatt    78840
aagttcagag cacagacaaa cattaagtaa tgatggcata aataaatgta attttatatt    78900
gtggtgcctt ctgtggaaaa gtttcaggat gctctgtggt acctcagggg aatctgattc    78960
agactgtgga gtcaggaaag catttctgtg cctgtgacat ttaagttggg tctggaagga    79020
ggagcatcca aaaggacctt gaagcttgtg tatggtcagt gtgtcatctc agctgaatct    79080
cacaatgatc ctaatggtca tacctaggac aggtatgacc tctgcccaat tgaggaaatt    79140
gaagccgtga gattttttgt gtgatgctta caggtgcata caattaatta tcttgttgtg    79200
aaagtttgaa tggaccccag ttcaaaatct gtttgctttg cactcacaa tcttaatagt    79260 ttgagaagtg gtcttacatt tgagaagatg ccccatggag gtgacatctg agcaggacca    79320
ctaaccatta aaaaataatc ccatgtaaat ggtgaaaccc tgtctctact aaaaatacaa    79380
aaattagctg ggtgtggtgg cgtgtgacta taatcccagc tactcgggag gctgaggcag    79440
aagaatcgct tgaaccaggg agtcagaggt tgcagtgagt ggagatcagg ccacagcact    79500
ccagcctggc gacagagcaa gactccgtca atcaatcaat caaacaatca ataaatccca    79560
tgtaaaataa agtttagtt ctgtggcctt atgagtgttt tccatacagc atatgaaact    79620
caagactctg aagtcttaag tggagaatca tttcgattca tttattttgc gaataggtga    79680
ggtataatag ctatctttct gcttctcagg aagacagctt ctaggagtgt cctgaacat    79740 tttgacccctt gaagattgtc tagataaaga ataaccata tttttaacct tgaaaatgct    79800
aataactaat tcctcaatcc gttttcctag aaacggtaga tttgtagatc tctcaagtgt    79860
cttagtgttc atctgatcta gctacactct tttacagata agaaaagaga ctgtgtgatt    79920 ttctgttttcc caaattgtgt tcacagaat tttatttctt ggaggtacct catactgcat    79980
ttccttctta acaattcata aagtaggcca ggcacggtgg ctcatgcctg taatcccagc    80040
actttgggag gccggggcgg gcagatcaca aggtcaggag atggagacca tcctggctaa    80100
catggtgaaa ccccatctct actaaaaata cagaaaatta gctggacatg atggcacctg    80160
cctgtaatcc cagctactca ggaggctgag gcaggagaat ctcttgaacc tgggaggcgg    80220
agattgcatt gagctgagat cacgctactg cactccagcc tgggcaacag agcgagactc    80280
tgtctcaaat aacaataata ataataaaat aataaaaat aaaaaaatca taaaatatac    80340
cagagtattg agaactcaga tattttactt tatttactg aatgtttccc aatctcttaa    80400
gattatatga tcgaagaata cttttattaa ataacaccca ttattattcc atagaacact    80460
ctttatgagc tagtaccata aagaattttt gtccttataa tatactgtat tttagtaaag    80520
```

```
tgttcatagt tgttttgcta tagttattta agagtaattc tagttaatct atatggtata    80580
taataacatc acacataatt tgaaatgaat attctaggaa ttttactttt gtacaaatgt    80640
tgggtagaca aatttatatt taaatagctg tttagcttcc aggttaaaag gttctggtaa    80700
gtatagcata ttattttatt gtttagtgga agtattaagg ctattacctt atttttaaaa    80760
gtggattttt aaaaattgtc agtgtgagaa tggaaatcaa attaagtgac acactattgg    80820
tagctgttct tattttgaa tttaatgaa atctggttaa aatgattaaa atgtttatct    80880
catttttttt cttttagctg ctatgccttt cttgcctcct tctatgacaa tcctaaaatt    80940
atctcagaac aaattttcct gtattccaga agcaatttta aatcttccac agtaagttta    81000
ttgttatttt aattttaaaa gcacattagc tggaacagaa cctttagaaa catgatttcg    81060
atttagtcat atagaggtaa ttgatttcta aacctactca acttgatgtt tttgtatgta    81120
tgaatgattt tcactagata aaagacccaa ctcattactt aaaatggaaa cttttatatt    81180
tatttagtgg atcattgtgt aaaaacaact taagattgtt taattaattg ctgtattagt    81240
ataatgaaat gagattatac tggctatcac tttaactttt aaaatttaa ttgtttgtgg    81300 aacttgatat gttgccaaaa tacccttaac tttcacatta tgcttaagtt atgtttgagt    81360
gaaattttgg gggaagatta ggcaagttta tgtagttcca ggtttttgag atattttggt    81420
taattcatga aaccgaaagc ttcctgttaa ctttaaattc aggcattaat tggatcttga    81480
gtgtgttgta atcttaaatg ctattctaat tatatcatac atgataaacc aaattcataa    81540
aaatatatgt gtaaatttat cttttccttt gttttcttgc tgtcagctat tccttcaaac    81600
actatggctt tttagaattg acactaaaat gctgcttgca tgatgctgca atgagctctt    81660
ctgtgagctt atatttaggc aaataataat tagaatttag ccatagagag tgttacacaa    81720
acctataata gctaaattac gtctagcttt agaatgtgtt taactgttct aactactcta    81780
cagcggttca tctctttaat cttcctaata atgccctacg atagccactg ttattatctc    81840
cacttcataa gagatgaagt aacttgccca gagtcatagt tcttaaacac tggtggttca    81900
acttcaggct ctcaaatcac atgcatactc atatgtcaat aatgctagtt ttgacgttac    81960
actttattct caccctgggg aaaattattt gtgatgttat ttcatgtatt ttggaaatac    82020
tcatttggtt tatgtctttt ctgtgtattg ttttagcttg cggtctttag atatgagcag    82080
caatgatatt cagtacctac caggtcccgc acactggaaa tctttgaact taagggaact    82140
cttatttagc cataatcaga tcagcatctt ggacttgagt gaaaaagcat atttatggtc    82200
tagagtagag aaactgcatc tttctcacaa taaactgaaa gaggtaagac gattattgcc    82260
acttaaaaaa tatactttat gatttgcatc attacaaatt atcattttaa gtgatattta    82320
gcttctaaat accaatttca tgaaactaga agcttcctgt taactataaa ttcctgtcaa    82380
ctataaatcc agatttccat taaatttaaa aataagaaca gctactaatg atgtgtcact    82440
taatttaatt tccattctca caccgacaat ttaaaaaaat ctactttaa aaataaggta    82500 gtagccttaa tacttccact aaacaataaa acaatatgct atacttatca gaacctttta    82560
atctgaaagc taaacagcta gatataaatt tgtctaccca acatttgtac aaagtaaaaa    82620
ttattagaat attcatttca aattatgtgt gatgttatca tataacatat tatagattaa    82680
ctcaaattat tcttaactgt tacttaacta tgacaaaaca acttagaacg ctttgctaat    82740
acacaagata gtaaaggat aaaaattctt tatagtacta gctcataaag agtgttctat    82800
ggaatagtag tggatgtcat ttaataacta taaattcaaa ataagcattg taaatatcaa    82860
```

```
taccattcaa ttttttttg ttttttaaac aagttgtaag cctaccctat ggtaaatgga   82920
tatggtaaca cagcataatt tcctcaaaaa attacttttg tgatatactt ttaaaggatt   82980
atatgaatat atacataatt atagatgaat gtgatgctgt gtgtcattgt atcaccaaat   83040
ctctgtccaa tctgttaaca gactcttaaa taaaccattt ttctcaagtt gttactggcc   83100
tgtatactgt attacttgtt tttcagcttt ccttggtaca ttcttaaatt tctgcattcc   83160
gccaccatgc tatcacccta atggatcaac ctttttgtt ttgctccatt ctctctgttg   83220
taaatctgaa attgataatt tgtttgtctc agaaaatatt attttcaag ttctagcgta   83280 ttgcctacaa aaaccaaaag aattaagtgt ctgacactgt gaggttcagc aaaactgtgc   83340
atatattttg ctacctgatt ttttgccagc aaatgagtgt tttctattat aaatatagta   83400
tatattgctt aaaaatttgg aacagaaaag aaattactcc aattaggatg ccacctaaag   83460
tataagcatg tagctgtact ttgagaacac taaattgcat gcaggtttgt agtgactagg   83520
tcttcttgcc tttactgaag gagcagaatg aagtcacaga taatggataa ccaaatccat   83580
tttgtggtaa gaacttcctt actttcaatg tcttgaagag atgaagtatg ttaccaaagg   83640
agattgggtt tttaatatt acagatgagt gacatagatt gtttgggagt aagttttat   83700 atgtaagttt ttatgttttt aaacacatac tgacaactta tgacaaacct ttggaaagtt   83760
ttaaaactct gttgaaaggt tgtgcaagct gctgatggaa tctgtgagcc tttcttgttt   83820
cttatcacgt tttttggcag agcacatttc ttccttccca ccaacaggtt ttgcccttt   83880 ttttcccatt aagattcctc ctgagattgg ctgtcttgaa atctgacat ctctggatgt   83940 cagttacaac ttgaactaa gatcctttcc caatgaaatg gggaaattaa gcaaaatatg   84000
ggatcttcct ttggatgaac tgcatcttaa ctttgatttt aaacatatag gatgtaaagc   84060
caaagacatc ataaggttag ataattttt tctatttggt tttactaaat ttatttcaga   84120
ttttctactc tctgtgactt tgatggacat atattgttac tatttaggga aaaataaata   84180
gtaatatttg gcattaatat gctgtgtgtc atttgccttt catttaatga atgtgtttct   84240
gtggtgccac tgtagagatt tctcattctt cttagccaga ctaatgttga gagcggcttc   84300
tcctccttct gtttctttc agtggagtag actctaaaag aaaataagta ttgctatttg   84360
gtctctggtt accaattaca caatctaaag aaatacagca cagtataata acttctcaca   84420
ctgtatttca tatagcaact agttaacata tgcctcttac atcttaaagc attatagcta   84480
ctgacatcat gtgaaattac taacttctat tttgcccatt aggatgagta atctactcac   84540
cttgatcagt tttgaaagca ccaaaacttc tcaagtatca ctgtttctgg tctttacact   84600
ttaagcactt taaatatctt tggtaatgga ttttatcctc cttttgttc cctttcagca   84660 catcggtctt attactttct cataaaatcc tttgctccct tttccacagt tactgtatta   84720
acgttgcaga cctcagctct gtcatcacct ctcaacttga ctgtaatatc caccaaggca   84780
gagaccatgg ctgtgttcac tcactattca aatcttggca cccaacacag tgcctggcat   84840
acaattaata gttgtttaat taccagtgat ttatacttac tcattctctt ctgcctaaaa   84900
tctcttaaat ttatatttaa cttcatctgt ttttatgagg aaggattttg ttttctgaac   84960
tcctgagctt gatttcattt taaggagtt tgttatcttt tgtgctaatt gtggctaccc   85020
ttcatcctac ccaattattt ttctctcttg aaactggaaa agatggtcat ataaaaattg   85080
gttcagttct tactaaacat ttagtagaac tagctttcag tgtattatac tgtattatct   85140
aactaaatat ttttaatatt taatatttaa tttaatatat aactaaatat ttttaaacat   85200
gtttaacatt ttcagaaaag acagaaagac ctagagcaga ttagaaattg taggcatcat   85260
```

```
ttgcttttg  aagaaagaca  ttttttcaaa  tagtggtgca  ttcttaagaa  ataaatcaag   85320
aaaggtaatg  ttgcttttg  gtcatatcat  caggaatgtt  ggtcagattc  ttattagtta   85380
caggaatgaa  ttgatcacta  ctctgatgta  aaattcactt  atgatttagt  cttttctct    85440
aatttgaaac  tgtggcaaca  ttttaacata  tttcaaaata  tatctttctc  tatccattat   85500
attttgata   acactttgac  tctactatta  gtttaaaggt  ggttttttag  ctacctaaac   85560
acttctattt  cattcaggtt  ttacattaag  atcattagga  atgaaagcta  acatctgctg   85620
atagtataat  agtttatatt  tatttatgat  gttatgtgat  ctcactatcc  atatatacta   85680
ttatatgcat  atgtgatata  catgaatata  tagctataca  tcatatatac  catatatgaa   85740
tatatacaca  cacatatata  atgtaactaa  tatgacccta  ttatcaagct  ttaacagtat   85800
acatatatct  ctaccttgtt  tctatgtcat  atggactttg  tgaaattttg  aactttataa   85860
tttatagggt  ttttcttttc  ttttcttttc  tttttttttt  ttttttgag   actgagtttc   85920
actcttgtca  cccaggctgg  agtgcagtgg  cctgatcttg  gctcactgca  acctctgcct   85980
cttggcttca  ggcgattctc  ctgcctcaac  ctcccaagta  gctggaatta  caggcacctg   86040
ccactgttcc  cggctacttt  ttggattttt  aatagagacg  gggtttcact  atattggcca   86100
ggctggtctc  aaactcctga  cctcatgatc  cgcccacctc  ggcctcccaa  aatgcaggga   86160
ttacaggtgc  gagccaccgc  acctggcgta  taatttgtag  ggttttttcat actatttaaa   86220
gacattagaa  tatgtataca  tgtatgtata  tgtgtgtata  tatagaggta  tatatatatt   86280
gcatatcgta  ttctaattag  tattgcaaac  atattttggc  cttttgatta  tttctggtga   86340
tagtgtaaca  tgttttcttt  ggtgatttta  ccaaacatta  tcaactaccc  taaaatctct   86400
agcaaaatat  atgcattaac  agtactctga  aagacatgta  cattattagt  tatatgagat   86460
atgcactctt  ctggatacta  tattttagaa  tagtgtgaca  tgtaaaagaa  ctcacctaaa   86520
tctcaagtat  acttttaagc  agtttattat  tttattttta  tctttcaaat  actaggtttc   86580
ttcaacagcg  attaaaaaag  gctgtgcctt  ataaccgaat  gaaacttatg  attgtgggaa   86640
atactgggag  tggtaaaacc  accttattgc  agcaattaat  gaaaaccaag  aaatcagatc   86700
ttggaatgca  aagtgccaca  gttggcatag  atgtgaaaga  ctggcctatc  caaataagag   86760
acaaaagaaa  gagagatctc  gtcctaaatg  tgtgggattt  tgcaggtatt  tctttctata   86820
gaattttaaa  attcactttt  accatttgtt  tggaacaggg  attcaaaaac  tgagcttct    86880
gttctaatat  ccagaaacct  ggtagactgt  atggaattat  tccaaagccc  ttcatttctc   86940
ctaattttac  ccttgcctcc  agaatggaga  agaaacatgga gggatatgtt  aggaacaatt   87000
tggtgctagg  tactttgatc  ggttgctgac  aaatatgcta  aaagtggtca  atcctagtaa   87060
aaacccagaa  tagttctcta  aacatggtct  gttgttttc   tcttattagt  atgctaaata   87120
ataaatagta  ttattctccc  agattttttt  ttaaaaagg   attcttgcct  gtcgtttgaa   87180
agattaaaaa  aatttgtctc  taatctttat  ttaggtcgtg  aggaattcta  tagtactcat   87240
ccccatttta  tgacgcagcg  agcattgtac  cttgctgtct  atgacctcag  caagggacag   87300
gctgaagttg  atgccatgaa  gccttggctc  ttcaatataa  aggtgatttg  ttctgatcat   87360
ttgaaaatag  aaaataattc  atgtgtctgt  gtgcgtgtgt  gtgtgtgtgt  gtaagttaat   87420
ttatttgg   caaacaattg  cttcagtctc  tttaaatact  ttcttaaaag  aagcactaaa   87480
attttgaatt  gggaaacttt  ccgagtaatg  aagtcataac  atgaaaattg  tatgttccat   87540
gttggtgaat  gttattggta  acctgaaact  cttttatgct  gtaaaacttg  aaaatatata   87600
```

```
tgttcaactg ttttttaatt atattatttc ttaaatgaaa tctaaatttt tctaatttaa    87660
aataagctat attaaagaaa agcaatctat atatatatat ctcatcaact ttgtactcag    87720
gggccattta gtgtgaaatt cttcagattg tatcctttaa gtggtcccag attattatgc    87780
tgttacatct ggaatctccc ttttgttgct tttctatctt ttcctttgtt gtcttgttgt    87840
cagctattcc ttcaaacact atggctttttt agaatggaga ctaaactgct gcttgcatga   87900
tgctgcaatg aactcttctg tgcataaagt ccttaaaaag cttgtgtcag gacatttaac    87960
catgtaattg gctgcataca tgcttgtttt gtaatttggg tatttttttaa tgtttctttt   88020
attaacttttt ttacagctag ccaacgtgag caaatagtac agtggcagtc atatttgctt   88080
gagtggcttt tattctttca ttgtagactc caaattggtt gactttaaaa cgaatttaga    88140
agattaaatt cacagataag gaagagaaaa tataaactat atgacgttaa tttgatataa    88200
tttgtgggtt tatgaaatgc ttatttttatt taggagtgaa taactcatct taaggcatga   88260
agatgggaaa ggaaaactat accactaccg ttatatatgc cacctaaaag ggtgaagaat    88320
tgggttaaga aaggccaaaa atgactttttt aaaatgtcgt aaggttacat ttttttctta   88380
ggtttaagga aaaaggaca gttgttcttt tcttcttctg aagtctgcta gtttctcttt     88440
tccattcaag tgaatgtcac ggaaagcaaa tatcaacagg aatgtgagca ggcccagttt    88500
gaaagcaaac acaagagggt tttgtgtctt tccctccagg ctcgcgcttc ttcttcccct    88560
gtgattctcg ttggcacaca tttggatgtt tctgatgaga agcaacgcaa agcctgcatg    88620
agtaaaatca ccaaggaact cctgaataag cgagggttcc ctgccatacg agattaccac    88680
tttgtgaatg ccaccgagga atctgatgct ttggcaaaac ttcggaaaac catcataaac    88740
gagagcctta atttcaaggt aacatggtag gctggtagag aaatgtaatt tattgattct    88800
caactgccta gaaatgtcag aaattttgag aagtgagcaa ctcacttaaa attgtgggtt    88860
ttctttcctt gttgctgtta gcattattaa agtccttttcc attttaaaat tatttatgcc   88920
agacttcatt tctaattcat agaaatggga acaaaaaata attagaggaa cctgagagaa    88980
actaagagac cgtttctggg atactgagaa aatgtttctg agagagaatc tgagaaaatg    89040
tttttgatgc cttttctgat tcaacttctt atagtggtga ttcaatcaca agggtaaagg    89100
tgaatactga ggtcttggga tcatctttct tctattattc tttaactgtt attttttccat  89160
ttcctctttt cttttggaat tcctgttttta tggacatctt gatcttttgt gccactcatt   89220
catgaatttt gtcactgtga ttcccattcc aattttttttc cctccgtatt gtgaggcagc   89280
tgtttttattt agtcatgaag accactaact tggttttcag cagtgtctca ctaattactt   89340
agttcataca aaatgggctt tttatttttag gaattatgtt ttaaatgttt aaagttatct   89400
tctcgtaagc caaattttta taaaatgtaa ataaatcagt tatcagagag aacacttttt    89460
ttttttaaata cttggcagaa aaaagaaatc ttcactgggt actacaggga gtgtggtgta   89520
aactgtactg aaaaatacccc ttgatagttc catatgacaa acataatgat gaatttcact   89580
tagtctgtct tggcttagct caatagcact aatgatcaag atactggctg ataaatagag    89640
tcctatttgg cctgggcagt cccagcataa ttatgtaata gtgtcccact atattctcaa    89700
aagcattcca atttggatga taaattatat agtcaccttg gttataactc catgctggcc    89760
agttagctta gttctgttcc atttatatag attatgtgtg cttcactcca aaacctaatg    89820
agccatttgt aaaagtgatg gcttttgcgg tgcccaggga gagaatttgt atgtttgtat    89880
ccttcaacac acatttatta cagttattaa aaggttttat tgatgataga tggtaatgtc    89940
atgtaaaaat gacatattat ttatttgtag acttttcctat tctcttgttg gacatgtaat   90000
```

```
tagaaactaa tatgacttaa agaaaaacaa atacacaaaa tttattcatc caattaatct   90060
cttaatccag gtgttttttt tttctgagac tatacccata cttcaataac tttgttgtta   90120
ctgagaatat tttgagtttc ccttttgtc attgttgtca gagaatgtat catatcttta    90180
aaaagacttg ttggaggatg agtttgtttt gaaaaggcct gaatttagtt gatgcaaagt   90240
cacagataag atggttcatt aagctgtatt aatactgctt ttgtctaata gatatcatta   90300
ccaataagtc agactagttt ttcttttggc acttataaat caccctttgaa gacaactttt  90360 tacaaggaaa taaaacaaat gctttgagaa ataccagtat tattgaaaga aaagtatata   90420
ttgctaatgg atgcagcatt ctggcataat ggtttgaaaa ctcatttgat tgctttgtag   90480
aagaatgact ctttcagatg acccagggcc tgtgagcctg ccagaacttg aaaattcttt   90540
cttccctgag gtgcttcaac ctgaattcaa agagcagctt ttaatctatt agagatcatt   90600
ttttgtcctc tcatttattt ttcatatttg cctttgatct tagctcttct ctaatctttt   90660
tctgtctcaa ccttattaac aggtgtctgt gcagacactt ttaagttttg ttttttggct  90720
cagcctgtca gttaactgat aatcatgctg aaaggagaag caggacaaaa cagagttcaa   90780
tgctgacaat actccttta atcttgtcca gcccattagc agagcaggca tctctgtggg    90840
ccttgagacg tagtcccgta aaactcatcc cgtttctact tgatttgctt tcttttgagaa 90900 ctcttgttta ttttttatatg gaggtttcct gccttggatt aaaacataaa cctcaatctg  90960
aagttcaatt tcatcttaat ttatgaacga ctaagagagg gaacatgaaa agtggaggtt   91020
agtgaaatta tctctaattc tctgggttaa gagatacatg aaaacagtct cttgagtaac   91080
catttgcagg taaatatgga agtaatggtt atggttgtct ctttaagttt ttagtcacaa   91140
gtagaaaaag accaagttaa ttttttttctg tgtgtgctga atttctattt gtagtaagtg  91200
taagaattta agcagaaatt ctgattcgta ttttcagata aaaagaatat gtaatttcca   91260
taggtccaga aatagggaga gtttgccatc tggtggttct taacggcact ctggatatta   91320
ttaagagttg catttctatt taaaattata ttttaaaaaa cgtttggaag atacttttat   91380
tgtagaaact atcctcttag ggccattctt taaaaaaatc ttattttata tatttctcat   91440
tttgttgata gtgattagat tctaagagca acagaacaat gatcatcctc tcctatcaga   91500
atcactgatg tttagatgat ttctcatttt cccaagttca aggttccatg aaaaacatag   91560
cttgagtggg attttatgtc tctgcgtttc actgttgata tatatgtcct cccaatataa   91620
cattttacaa ataaccaagc acaaaattta atattttacc ttgaatattt aaaatataat   91680
aatatccaaa agctcttgta atttgtactg atatcttata ctagcgtgtc tgtttcacat   91740
taagtttaat gtcttaggat ataaaaaatc ttttttatgg ttagtgattt atcttgtttt   91800
tttttccatg gaatttctgg atagcgagat aaatatttcc atactatttt atttgatatt   91860
tccaaatttg cctctgaatc aacaattttc ctattttaat ttcattgtac ttgttcctta   91920
caacctaaat agcttttttat tatattttga ttttatttaa aaatgtactt ctgaataata  91980
tatctgtttc tgtaaaaact gttagcactg aatttgccaa ccatttgaca aatacacaaa   92040
taaaatagat tttttacggct tgtcatttgt aatttcatag atccgagatc agcttgttgt  92100
tggacagctg attccagact gctatgtaga acttgaaaaa atcattttat cggagcgtaa   92160
aaatgtgcca attgaatttc ccgtaattga ccggaaacga ttattacaac tagtgagaga   92220
aaatcagctg cagttagatg aaaatgagct tcctcacgca gttcactttc taaatgaatc   92280
aggtttgtgt ttttcgttcc ttattttcaa agctcagctg tagtaactta taaaagtgtt   92340
```

```
tctgaatctt ttatagaatt tacattcaaa gttgagagaa tatccatacg gttctttaat    92400
aggccactga ttttttctt tttggaagat catcatgtgt gttcatgaca aatcatgtat    92460
catgtcataa gaaaacaaat ttagaaatca cctaggagta aagcagtgga aagagtccct    92520
gagtgggagt taaaatattt gggttctaga acttgtcttt actattcagg agctgtggaa    92580
ccctgaatag tcaaatgaca ttcataatgt caaatgagtt tagtgcatgt gaaagttatt    92640
tttatattgc aaaggggaat tattgttggc atggtctaac tgggacgctt ggagagtcaa    92700
tggctccctg agatgatgca gcttctgagt ggaagatcta gctctcttgc atcaaatatt    92760
gatctcaaag atgaaaattc tcaaagcaac ttcagtgcta attgtgtact tgatcatatt    92820
accttgctag aaatgtgtga gttgtttgat agtactagag taagtgactg ggaagctgct    92880
tttgatccct agattctgtt gtataaaaaa tagcttcccg tggtttatga tctgttcctt    92940
ttccccatcg ttcttaaggt atgctgagat atgctgtgtt tcttatctgt atttgaaaat    93000
aaaacatgtc tttgtagtgt gtattcagca agcgaaacag aaaattatga atttctactt    93060
atgtgtgaaa tatgctctgt aatgcatgtc agtgtctcaa atatgcttaa atatgatcat    93120
tttatgtagt ttaaaaatac tccattataa tattggaact ttagaccata ggatgcacag    93180
cttctagtcc cagctctgtc actagctatg ctgaaatttc ttcacctgca aaatgaggaa    93240
gttggactag attttttcta aagccccttg atatttgttc tagattccat gtttcactgt    93300
ttgatgactt tttactacag gagtccttct tcattttcaa gacccagcac tgcagttaag    93360
tgacttgtac tttgtggaac ccaagtggct ttgtaaaatc atggcacagg ttggtgtctt    93420
ttatttttgt ggcacggggg ttatggtcaa agcatagaac agatggcgcc cagagcattg    93480
agcattttag aatttgggtt tagttaaggc agaaacttt tgtgaatttgg aaaactgtgg     93540 aacatttcac atagaagact acttgaagag cttcatggaa gaaggaaaga tgtcttgagt    93600
tcacttccat gacttggttt tcaagccaca tacagatgtt tgtatcactc tgccccatgc    93660
tgctttacta gatcctgatg atgtcattgg tttggttact gaattagtca attgaatgat    93720
ggctttgtgg aaatccttgg ggtaaacaca tataagaaaa ttaggttgct gagcctgtga    93780
aacctctatc tagataacat ggaggtgagt tttgacttaa gtgaaatgat ctgagcttta    93840
aatgcttacg attttgaaaa cttttggatgg ccttggttat agctattttt ttcttatatt    93900
tcacatggaa aatgattttt ttctccaaat gataatccat taccaatgag tttaattagt    93960
tataataatc catctctgta gctttgacat aaaagaccat ttgagcaaaa catactacct    94020
cagggctttt caaccccagc atgatgacat tttgggccag ataattcttt gttgcacatt    94080
gtaggatgtt agcagcattt ttggcctta tattcgagac gtaagtagta tcctctagct    94140
gtgacaagca aaaatgtatc cagacattgc taaatattgc ttggagaatg tgaaaaatta    94200
ccctagttga gaaacattaa gctactgatt tgttgatgag taaaatttat agttttgcat    94260
gtggctgccc gagttcctaa aattattata tattttatg ttagaaatat ctcttccaat     94320
taaaccataa aggtaattaa attcactcag gcagccttga ataattgttc ctaaattcca    94380
tctaaggaaa aaaaggaagc tattgtgaag agagaactca gttgaggcta aatcctgtac    94440
catggaactc aagagcatat tgaaacattg caatcagcaa ttatttgcag tgtgtcagtt    94500
attactattt tggtaggtat ttttaaatta gattttcagc cttctgcaca tatgtcatgg    94560
ataatgtgat tttactcaat tattaaatga taatggagac agtagtgtga cccagagcac    94620
ttacttgagc atcagcttga cctacgtttc agtctcttta attacttatt agctctgtga    94680
aatttcttaa tgcattaagc ctttgtttac ttacttttta aataaggaaa ataacaatta    94740
```

```
tcttctatat tgcctccctg gttcagtgta agtgaggggt aaatgttagc taattttata   94800
ttggatctat ttggcaattt aaagaatgtt aatcaggaaa ttttaaaaaa ttcagaacta   94860
taaagaggta cttacgtagt tttggaaagt gtgtcatgta tggggacaaa taaaaaagat   94920
gtgtaggtag ctgcatcctg tacagcaaag gaagttttaa atatatccag caattttgtt   94980
gtcctagctg gcgcacaata gttatcagga ggtaactcaa ctccacatag tcaaggaaaa   95040
gctaaagttg ctctctaaag tggtgtgttt ccatgtcact atggaacact tgaagttgca   95100
cacatgtgaa cattaggatg ggtatatctt atacagtaga ataaggaaga ggtttgcatc   95160
agaactcccc ttttaaaaaa atgcagattt tcactatgac tgcaataaaa ttcctgaaga   95220
ttctgtggag taattaagtt gaaactccat gaaagttctt ctcattagca tagttataaa   95280
tatgataatt taagtaaaaa ttaagttaat ttgagccact caaagttact tttaaagaca   95340
gatttaaaat gtcaataaaa tgataattta aatttccgat taacctaaaa aagaagtgcc   95400
atcattttta tttatgccaa taaattgaaa tataatgtca ttttatcact aaggtttaaa   95460
ggaaatgaaa tctctaaata atcaagtgaa accaagagca acttgtctga cagctattag   95520
caaaaataaa taggagtatt caccttcatg aatcaaggca agggccggaa taatttcatg   95580
gtgcagaagc tctaatgagc ccacccactc tatgcgcccc gagctgttag gtcactaaac   95640
ttattaaaaa aaggtaccat taaggcaggg agaagtttac aagactcatt taactgtatg   95700
ataaaagaga tatgaaagag acctattcaa ttaatcaggt ggaacattaa aaagcttaca   95760
tggcaattta accttgataa aaatacatgg gagaaataca aaggaatttg gaaaattctc   95820
tttccttgaa taaggcatca gttagctatt caggttatga ggttgaagga atgttaggag   95880
ctcttttaaa ggtgataaag tcaagataat gttgcagatt ttattcttat gtaacaaacc   95940
ccctcgaaac ttggaggctt aaaatgtgaa caatttatca tttctcgttc ttctgtggct   96000
tgactgggct cagctgcgtg gttctgctcc acatggtatt ggcaagggtt attcacttgg   96060
cttcattcat taaactgagc tggaaagtgc aagaaggta catgcatgtt tttggagtat   96120
tggtgcttct ccatgtggcc tatcatatgg ctaagttggg cttcctcgtg gcacggtgat   96180
cacagaataa ttagacatct ttcatggtgg ctggttacca agagaaatga agcagatttt   96240
ttctgtcctc ttaaaggcta ggccaaggac tggcaaaaat attaattctg ctacattcta   96300
gtaaccagag caaccacaaa cctagctcag attaaagggg aaggaaaaga gactctatat   96360
gaatagcacc tatgtatagg gatggaaatg atgtgtccat ctttggaaac ttccactata   96420
aatagtggta gcacgctata gatccactag gaaaatcaag cacaaactct ttaaaaaata   96480
agtgtatctt agtaaaatag attagaataa ctagataata atggctaaca tacatgaggt   96540
taatatgtgc ttttcaaaga ttagctcatg taattctcac agcaaccttt ccaaatggta   96600
ctttattagc ccctatgata cagatgaaga aattgattga cagagaggtt gaataattta   96660
tccaacggta cacattcagg aagaggtaga gttagaattt caaccaagt agtttgactc   96720 cagggcctat gagtttatac attcataggg ctgatattca aatgagagaa gagaagtaat   96780
aaataaacat ataatatgtt gagtggtaca gagtgctaca aagaaaatat gaagtgcagt   96840
tggagatgaa ttgtcaaaaa aggtcttagc acttaaaaaa cactaaaaca gcaaacaatt   96900
ctctttacca cctaaactgt aagagcgatc tggaattgct ataaagtaca caacatggga   96960
gaagtcttaa acaacagttt ttattattta taggcccatt gcacactgtc attaaatacc   97020
aatatgttca atcaaccatg cattcattga ttcaataaat actgtacata caaaatagaa   97080
```

```
atacagaaat gggtaagaca agtccttggg cctaaggact ttataacctg gtatttcact    97140 caactcacatg atagcataaa taatgtttgc ttctgtttaa gtattcctta aacattatag   97200
atctcccaaa gaaaattaaa tacaaacctc ttttttaaagt gaatttgaca aagcaaaata   97260
aattggaata tatagataaa tatgctaaaa tttgtcatat gtactttgcg tactttacat    97320
gtgttatttc attctcaggg caatctaaga cagtcacttt tattatctca ttttatagag    97380
aagaaagctg tgcagtaaag aaatcaaata ccttttcccaa ggttacagag ctagtagtag   97440
agcctggatt tgaatctggg ttctgactga tttttaactg ccatgacaag gatcaaagct    97500
caaagtgtga tctctgtgtt agaaacatcg gggttgctct ttaaaaaagc cgattctcag    97560
gcctcaaccc agacctactg acccagacac tgcaagtaga atccatcaaa atgcagtagt    97620
tactttgaga atcatgaaac tctgctacac agtctgtctt cctattcatg gaagtcctct    97680
cctagtatat aaatgtgaag taatatttct atttcaaacc tgtattgata actgtctgga    97740
agataatttt cctgggaata tattattgat gagactgcaa aacagatgtg aggtattgga    97800
ttgatctttc cattgtagct agggaaatac tgatgttcat tgtttcagtg aagttcaatg    97860
atttcctatc cgaattaact cccttaattt aacaattttt tttttttttt tgagagtgaa    97920
tgcccctctg ggcttctagg ccacatggtt gctagagaaa ttaggtactg tgttgcactt    97980 gaaacacta aaatctttct gactactttc actgagcaaa gagacataaa atgctttaaa    98040
tttgcaacat ttcagaaaat aaattttagt gattatttat gactcgaatc tttcagattt    98100
tgacagtgaa agtggaaggt tgtccaaaac accctaaggg cattatttcg cgtagagatg    98160
tggaaaaatt tctttcaaaa aaaaggaaat ttccaaagaa ctacatgtca cagtattta    98220 agctcctaga aaaattccag attgctttgc caataggaga agaatatttg ctggttccaa    98280
gcaggtaaag aaaaccttaa aaaattaatt gctacatgga aattcactat ctattctttt    98340
aattgtcaaa ctaactgtag tctataatag atgtattaaa taaataaata tattttgctt    98400
ctagtgtaaa cctcctactg acatgtatca tttattttgg aataaaacat tgcatctgac    98460
actttaacaa tatagtaaat cacttacttt atgtgtatag ttactagttg cttatcact     98520 gttgaaatta tttaagaaag gtaaatagtg gagattaatg tgtgtgtgtg tctgtgtttg    98580
tgtatgtgtg tgttcttaaa caacactgag agagtttatt aagcaagttc tgagaagata    98640
gtgagttttc aacagaattt taaaagcatt tatggcatca caatggatgc ctatgtttta    98700
gcctatacta tggaaatttt tcctactgct ctaagcaact gggaaattta taagtaata    98760 tgatgttgaa atgtgcaaat tacattgatt gatggatgca gccaattta aaaataaata    98820 tcacttttt ttctaggaca tgtattttc aggatttata taagattaca tttgtctatg     98880
cataactaat tgtaataatt tatgtattag tgcacaggga ttaccgaaaa tatttcatgc    98940
atctacatct gagcatgcat ttgaattggt tattgaccac tgaattttg gtgtaggaaa     99000 aatatgtagt gaaacaatgt tacaaaaaga ttacaattgt ttggaatgat taccttcatt    99060
gactttaagc agtaaaatca tttgctcaac aaggttgggt gttttgtgag gctgtataac    99120
catagtgtcc ttttgccttt agtttgtctg accacaggcc tgtgatagag cttccccatt    99180
gtgagaactc tgaaattatc atccgactat atgaaatgcc ttattttcca atgggatttt    99240
ggtcaagatt aatcaatcga ttacttgaga tttcacctta catgctttca gggagaggta    99300
agtatctaat gaagacttat tagatttta gagactatta atttagactt attaattttt    99360
agagaaatta gggagatggc atatgaaaag taatatgcca ttttctcaga gtttacttgt    99420
ttggaaggca gctgaagaat tagaaaataa gctcataaaa ccttggagta ggcaatctaa    99480
```

```
agacacacaa gcacatataa cctcatctaa tttgtcagga agaaaattcc ttaggtgctc    99540
actcagatct tgactgtgat tacattgtag ggactgtaat tatctctttt ctgttgcaca    99600
gccactaaga catttacaaa aaaagagcaa atccggtgtt tataatgcta actctttctt    99660
ctaaaataaa tagagacatt ttggtactcc aaagggaaaa tatcattttg gggattaaaa    99720
ttagctttac acaggtgtta ctggtttcca aaataaacct taccttgatt ggaattaatc    99780
aacatatagg tagttacatt gcattaaaaa gttcagaaag ttttgcgttt agcatgatca    99840
aaaacttctt tttaaaaatt atgaggattt atttatgatt ttctttcttc atctgtcgag    99900
catattaaac tgcttaacag catcaacctg aaatggatct taatgtgcag gggatttaac    99960 tcttttatt gtaaagttgt ggataaaata tttaatagat atggatgagg actcatatca    100020
gtaacaaccc aatactttat ttcaaaatga atagatctgt attacaatca cttgtgttgt    100080
gtgcagtaga ttttttccct ttaacttagg aagcagttaa taattaatgg ctccattttt    100140
tagaacgagc acttcgccca aacagaatgt attggcgaca aggcatttac ttaaattggt    100200
ctcctgaagc ttattgtctg gtaggatctg aagtcttaga caatcatcca gagagtttct    100260
taaaaattac agttccttct tgtagaaaag gtaaggaaat caatttgaat gttttcaatt    100320
gcaacactaa agaaatttaa acttaaaaaa aaaaaaaact ttaccttaaa gctttgcgac    100380
agtatgaggt ttagacaagg tgttgagctc tgttttgaat catgtaggct gtattctttt    100440
gggccaagtt gtggaccaca ttgattctct catggaagaa tggtttcctg ggttgctgga    100500
gattgatatt tgtggtgaag gagaaactct gttgaagaaa tggcattat atagttttaa    100560 tgatggtgaa gaacatcaaa aaatcttact tgatgacttg atgaagaaag cagaggaagg    100620
tatgttttga tacaacttac aaatgctttt aagtgatcct tcaatactta tgaagtgact    100680
tttaataaat gtaaatattc ttatccataa gggatgagtt gaaaaatagt atattcaatt    100740 ataggggacag ttcagaaaac tgaattatat ttattaccaa taaatcttg tattctagat    100800 tcagaaaatg ttgatttgag ggtttgaatg ctggcttatt gagcaacata acctcatctg    100860
tgaaaccgga ataccaacca catctatctc atagaactgt tataaagatt caaatagaca    100920
atacatggac ctaatttacc aacatgtctg ccatataata acagctgcag cttcatgaat    100980
gtggcaaaag cagagagtag ataactttct agtcagatgt ctggtagtct gcagcagttc    101040
agaattctac aagtgaacgt aggaataagt ttttaaaatt ccaagtagat agatactaag    101100
tgaatcttta aaatgttctc aaatttccta gagaaatata ggattggtta gaaagggagg    101160
gattagaaat tatagaaaat attccattat tttttcacat caaaaccaca aatttatgta    101220
tctccttaaa tgttgttttt atttaaaaaa tgtttattta cttctcagga gatctcttag    101280
taaatccaga tcaaccaagg ctcaccattc caatatctca gattgcccct gacttgattt    101340
tggctgacct gcctagaaat attatgttga ataatgatga gttggaattt gaacaagctc    101400
cagagtttct cctaggtaat tcttttttgtt aatttgagaa taaaaattag gatgtaattt    101460
tctccttata atttagaaaa tagatttcat aattatattg tcatagattt tactgtcttc    101520
atatatttgt tataattttt gtatttggaa tgatatattt taaaggaata taatattaca    101580 gatctgaat ttgttttgca cataatcatg tagactagga tcaagatgag gatgagatta    101640
tcatggaagc agaaatattt atgaaatata tctttgtatt tgccttaatt gccagggata    101700
tgggaggcaa ataagacagt tttcaggtga gttaagtgaa gcagccatat tttataaaat    101760
gacagaatag gtaaaggaag cacacctcag tgtagccata gcagggggttt tatgactcag    101820
```

```
tgtgacaatg ctgaattctc atagaaatat tcattaaaag ccttgaaatt aaagtcaaaa   101880
gtgttacatg gtgacatact caaatacttt tttttttttt tttgatatgc tgaacaattt   101940
acatttcttg gttccgtgaa ttcaatcagt gattttcagt agagtatgat ggaaatcatt   102000
gaattcatgt agcatgttta ggtgctcatt gagaaaaggt gaagtcatgg taaccatgtt   102060
tcaatattct catttgtatc ttgacttcct gcacatggat ttttgggcct aaaagatgtt   102120
tttaaaacat gctcatacac ttcagaagat gaaaagtgta tgcattataa ctactttggg   102180
aaagaaacag tcaacatatg ttactgtatg tcattctgta gattacatgt gtggtttctc   102240
atgtctctca gaataaaagc taatgtcttt acaagacctg cgatgctgtg atctgtctgg   102300
ctcctcggtt atcatttta aaaaagata tactttgtac aaattttttt aattgacaag   102360
taaaaattgt atatatttat ggtgtacaac atgatgtttt gatatatgta tatgttgtgg   102420
aatggagaag tttagctatt taacatatac attatctcaa atatttatgt ggtgagaact   102480
attaaaatct actctcatag caatttacaa gtatacagta tgttattatt aactgtaggc   102540
tgacatactc aagtttttaaa cattcctgag agtcattggg acaactatga aatgcattag   102600
attgatttaa tataaagcat ttgaagacaa ttttgacctt actttgttta gttttttgttg   102660 ttgttgtgtg tatacattta attttaatca aattacccca gaataatgc ctaagatctg   102720 tcagtcagga cataatatta ttagcaaaaa gttgtccaaa atttgagaca tgatatttaa   102780
agctaaataa actcctttat acccctctta ttggcattga ttgggaagtt taggttgaat   102840
ttaaatgctt tggaactcag gaagttaatg tattagtaat agtgggttaa cataaaatgc   102900
tgaattgtcc ttgctgaatc ctacatctta accccagact tcaaggtata caggaaagta   102960
ccagacatgg tgcatccttc ctctgaagaa atcccaaact gtcagacaca gatccctaaa   103020
atatttcttt ttcctgcatt aaaatgtgtt tcagatgaat ggacacgttt tgagtagtgt   103080
atgtggaaac gtcatttaca aagtctgttt agttggccag gtgtagtagc tcactcctgt   103140
aatcccagca ctttgggagg ccgaggtggg tgtatcacga ggtcaggagt tgaagaccag   103200
cctgaccaag atggtgaaac ctcatctcta ctaaaaatac aaaaaaatta actgggtgtg   103260
gtggtgggca tctgtaatct cagctactcg ggaggctgag gcagagaatt gcttgaacct   103320
gggaggcgga ggttgcagtg agccgaggtt gtgccactgc actccagcct aggcgacaga   103380
gcgtctcaaa acaaaacaaa acaaaaaaca aaaagcaaa gtctgtttag ctacccatat   103440
aggaaaatgt ttgtgattac tctcccttct ctagacccat gtcccataaa tccataaatc   103500
ccatgttcat ttacagaaag cagtctagat aggagtttct cagtctttga gctgttgcca   103560
ttttggcttg gataactaac tctttcttat cgagggtcat cctgtgcact gcagaatgtt   103620
tggcagcatc tctgtctatc cactagatgt cagtagtatc tcccccttccc tcagatgtga   103680 caatcaaaaa tgtctccgga tgttgccaaa gataaggggt ggggttgaat accagtgatt   103740
taaacaaatt aggtgtatcc ttctaaaaac attttacagg tagcgactcc agcatcttta   103800
tattagagta atctggagaa ggttatgcct ctctcaattt ccctcttttc cattttttatt   103860 tgtagggcag caatgcattc aggcttttgg taactctttt tcccaagata gcagtaacta   103920
ttatgcagtg agtaatacga cccaccttaa tagatatgaa tagacttgtt ttgtgaatat   103980
attttaaaat ataaatgtat gggattctgt tcatgcgtct gagaagccac agggtacatt   104040
tcctctttgt ggagctattt attttttctgg agagccaaga caggtatttc cacttcagtg   104100
gtgtgatttg aggggttagg aaaatttcct tgccttcaat tttctttcca acctagatgt   104160
cacaaataca taatagtagt ccttaacttt attttttgttt tcagtcacct gaaagacatg   104220
```

```
acaatccata ctccatatta atgcagcggc gattctcaaa tagagaaggg ctttaaaaaa   104280
ttagaaatct ctgccgggcg cagtggctca tgcctgtaat ctcaacactt tgggaggccg   104340
agatgggcgg atcatgaggt caggagatcg agaccatcct ggctaacacg gtgaaacccc   104400
atctctacta aaatacaaa aaattagcca ggcgtggtgg tgtgggcggc tgtagtccca   104460
gctactcggg aggctgagtc aggaaaatgg catgaacctg ggaggcggag cttgcagtga   104520
gccgagatcg cgccactgca ctccagcccg ggcgacagag cgagactctg tctcaaaaaa   104580
aaaaagaaaa aaaaaagaa aaaaaaaaca actagaagtc cctactccaa cttgaaattt   104640
ggatgtatct ccctagagta tgtttcttct ctatgctgca ttgcaatttt tctttgttgt   104700
tgatagttgt ccagattgag gggaggcaga acaagatgca tctatatgtt tccatctctc   104760
cgaccgattc tctcccttcc ccctctactt gctttctttc tcttttccct cttctgttta   104820
cccgattcta tttctgattc cagtatgtaa cagttccctc tgaagctctc tcaataccaa   104880
caatcctaac taatggtttt taaaagtcaa atattaagta ctggagggat agaatgagag   104940
aataccaaga ctgataagat gcaaataata ctttaacat atttacaatc taatagaaat   105000
acaagacatg ctcaaataag ttaattattt taatatactc tctctgagca taaaatataa   105060
ttatatatgc tcattataga catataaaaa ataaataggt agaggcttc catagatgtg   105120 taatttcacc acttgaaaat tactatattt cctatagac tgttttgtgt gtattcactt   105180
atatccatca agtgactaca tttcaaggca ctatatgaga accataaata ttgtacaaac   105240
aggatttgct aaatgtcggt ggagagtaac agtccacggg gctgatcatg gtcagtttgt   105300
gaggcaggcc tccaaactcc ttggggattg agatgatgga gtagcagagc tcttcaaggg   105360
tatggaggcc tgaaggtaca aagcatgctc aggaaatttt ggctattgcg gtttgtctag   105420
agcacttgtt ctcaacctta cctgctcatt actaattcta ctaagtacag aattaaaaga   105480
agaaaaaaat ctaatgacca tttcctcctg ggactaatta gatcaaaatc tttgaaccca   105540
gacattagcg tttaaaaag ctcctcagat gtactattca gccaggactg gggcagggaa   105600
agctactgaa ctccagcctt gagaatgaga agtagaacaa gaggagaact ttaaaaggat   105660
ttaggggcca ctatatgact atggagctga atttagattt gatttagtag gcaacgcgga   105720
ataatttgtt tctgaacagg agagtgacac aatcaaagtg gaatgatagg aaaattaatt   105780
ttgcaagaga gagagaatga gttggaagta aggaactcag aaggcctcct gggactcagc   105840
agaaagctct gaggccacca aatgggtgtg gtggtagtgg aaatggagaa gaagggaatg   105900
taaatgaggc tacacagtgg actgccactg ttagccgtgg ggttagacca cagcaagagt   105960
taaaataatt cttcaatttt aactccagaa gggcctcaaa aagacttttt gtcttgttat   106020
catcagctat atgaaggta gaataaaaac tagttaggag aaaaggtaat aaatgtggct   106080
tttgataggc tgtgattgag ttggaagggc ataccagtga aatcaccaac acaaagttgg   106140
aagtgtagga aagcacttag gaggtggcta aagtgaaaa tgtgaaaatt ctctacatta   106200
aagggataga tgaagtcaca gaagtggatg acataattga gcagggtatg tgtagaggga   106260
agacgggaag gttaaggaca aaatctttac atatatcttt cttggagtag aaggaagagg   106320
aaatgttaaa ggagatttga ttcaatgaaa caagtaggtc aggtttctat tcaaatttac   106380
aacagatata attacaacag atataattta tttagttttt ttcgcttgga cagcttaatt   106440
taagtgcttt gtattttctt ttcaaaaggt gatggcagtt ttggatcagt ttaccgagca   106500
gcctatgaag gagaagaagt ggctgtgaag attttttaata aacatacatc actcaggctg   106560
```

```
ttaagacaag taagaaattc aataatataa ttatattaaa ttgcacatta ttaatctact 106620
ggaactctta ttttgcatac agttgtgaaa atgcaaaata atgaccacat ttctacttaa 106680
gtttaattat gcaatcctag tttgtctttt cgttgtggag tagaaagttt tgtgttattt 106740
ctcctgttga gaaacaaaac actgtatctg agaatcctta taatcgtgat acatagtgtg 106800
ttgtaaaact ttttgtaaga ctcacttaca ctcctctttt tactttagaa ccttgctgtt 106860
caaaatgtgc tccatggaca agcagccagg cattacctag gagattgtta gaaatgtaga 106920
aacttgggac ttttcagtgc catattattg ttcctgatac tccacagtag tcagactcct 106980
agctgcctcc acctgcttcc agaccttgaa gcctagcaag ctcctgactt cgccttctgt 107040
tttcttcaga gtatttatct tttacttttc tggtctaggg agagaatgat ttttattttt 107100
attgaacatg acttctgtgt gttcagggtg aaagaagaag tttaatgcat gatctcacat 107160
tgctaatttg attgaaggtt agaaatctta aactaaaact ctcactgata agcttgcacc 107220
tctcttttct ggatttatcc actttaataa gaactgctat tgattacttg ctacaaagat 107280
ggagaaagtt agcatgctta tcctatttcc tactccctgt ccctgtccac ttcctaaaac 107340
ttaaaattgg ttgcattaat tttcctgata tagtaacaat tataacttgg aatgattttc 107400
aaaacttttg ttttttttagt ataccaactc tagacagcat ggactgactc cttgctatgt 107460
gagatgagga aaattaacgc tattctttct ccttttccca tcaccttctc aagttcttta 107520
atttattcta ttattttttat gtagtgaaag tttataacat ttatattctg gtctgtactc 107580
ataattaaat tgttcacatt ttgtctatag tttggttctg agaacaaaac caataaatgc 107640
catttatata tttttttatt tgtacagaac caaaatattt ctacttctag ataaagaaat 107700
gcaaccttct gtcactaact tcttttacta atagaatagt aacattccaa atatcaaagt 107760
caaatggatt ctctattgtt atgtatttat catcaattta taaaaataaa ggcatatttt 107820
aatttggtca cattttttacc ctgatttaaa aaaaaatttg tttttagaga tggagtctca 107880
ttaggttgac caggctggtc tggaactcct ggcctcaagt gatcctctca ccttaacctt 107940
ctgagtacca gtggtgattt attttatgta gcttttttgag gttttctgat tatatacata 108000
tattttttaaa aaacgtactt caggaaaaga tatatatttt catcatgact tcaagtgttt 108060
ctaagttctt aatcatacag tttgtataac agaatctact ttcttcttga agacattcct 108120
cattcagcac atgacttact gctctaaaca ggagagatgg attttctaggc tgcttgtgca 108180
gtgattaatc tatgagttag tttcctcgcc ctctttgatt actctcaata tttcttggat 108240
tccatccatt ctcttggttg gattgtcctt agttttttgtt gaagaatatc ttcgagtaat 108300
tttttttaaga aaaggtgttt gtgaggtaaa tgttttcagt ccttacatgt taaaaatatc 108360
ttagttttgc cctcccatgt ggtggatatg tcatcacact ttatttttta ggaatctagg 108420
cttgaaacaa ttttcttcaa aatttgaaga aaattccatt gatttttagt gcccactgtt 108480
gctaatgaaa agtctgcagt cagtcagatg tttgctccta tctaggatac ctttaatttc 108540
attttgaaaa ctgaaaattt gaccttttga atttcatttg ttttcagtgt tctgaacctt 108600
tacaagtatg tgtttgtgtg taggttgttt ttcattccat ctaattcatt attttgtgaa 108660
aaattgtctt ctgtgtattc tcttctatta tttattattt cctccctaac atttattaat 108720
cattttatt gacaactact atgtaccagg ttaggtgatg ggacatatga tatatatata 108780
gtagtaagct aaacccagtc aaggctctgc ttctctggag cctatatcta gttacttatg 108840
attcattatt gcttatcatt gctccaagag tatatgttag atgacaagcc ttttgggtct 108900
atcatccatg tttgagttcc ctcttcaagt tttatctata atttgtgtta cttacttgac 108960
```

```
tgtctcttac aggtttctaa tattttttag aattgcatca tctattattt agctttctgg 109020
tgaattttgt tttgataatc atattttcca tttccagcaa ttctttccat ccctctggt  109080 tgttcctttg tagccatgtt tttggataaa atgtccatag gtgtttctgt tcatgtcaat 109140
tagaattttt ttttgtatta cttgcattat tgctttttc tctgaggtta tttgctctgt  109200
gggttcatct tgatctttct cttttatctt gtcagttttc caaattgagt agttttgggt 109260
gacttcgtat gaagtaagta ctctattgat tgttaaagaa ggactgtatt gattattaaa 109320
ggtaactaga atgggcattc ttcacattca tgtaggtttg cttgttcaag ttaccacttt 109380
ctgaacaaga aggttagacc atagactttt aagggctgca tactgcaaag ggatactctg 109440
ttctttaggt tacatgggca gggatcactg ctgagaccat acctgccaaa ggaaggcagg 109500
ctttgctctc tagatgctgg acttgaaatt gtttccctc tgcttagtgc tgcattattt   109560
tttttgcttc ttaatctgct gcagagtatc tagatcaggg tgtccaatct tttggcttcc 109620
ctgggccgta ttggaagaag aattgccttg ggccatatat aaaatacact aacactaatg 109680
atagctgatg agcttaaaaa aattacaaaa aaaaaatctc ataatgtttt aagaaagttt 109740
atgaatttgg gttgggccac attcaaagcc atcctgggcc acatgcgacc tgtgggccac 109800
aagttggaca agcttgttct agatacttca gactctgttc tacatctctt catagatcaa 109860
taacttgcag caatgagttt atcagataaa ttatgttcac ttttcatcca taaaaaaagt 109920
catgggaggt actcaccata ggattggttt aatccagtca ctctggccaa ttttctttaa 109980 aattcctta accttggtat attggtttaa ttccttcaga atggcttttc ccattgtgat  110040
aaactggttc caggcttcac gagtacttat tccaagtaca gaaggaaaga gggtacctct 110100
tttgagtact tgtatttcaa aggaatcaaa tggcctacat aataaccat taaataaata   110160 gatgtctctc agccccagtg agtcatctgt gcttttctca acaagcacta tgttcagggc 110220
aatgctttgt gctaattggc tttaggcctt tgttaccaaa ctgatcactg tggccctgag 110280
ggtgctgtta cttagaatat tcccacttt tctgagaggc tgatgttggg gtcacttccc   110340
cctgaactaa agtccagggg ctgcatgggt gagggttgag taactcagta ctctaaggag 110400
gaaaggaagg ggaatataca ctgttagtta acagtggtta ttcctgtatt ctctcttgtt 110460
tggattctac tggggatttc tttctttttt tgagtctta ttgacattag gaatgagaga   110520
tagaaacagg gtgagagagg aagtaaaatt aaatgtgaat tcttccatct tataccagaa 110580
ctcaactgta tttttggaat ctatatatcc ttactttcc cttgatttat tacaaaaaat   110640
tcttagtggc tacactaagt aaattttgta acctttaaaa aatacatagt tataatattt 110700
taagtactct gagtaataga agatttcatg tgagtacaaa atatcctggg ggcattttaa 110760
ttattagtaa caacagtcac actgtagttc tagaaccaaa ttgaacattt tatatataga 110820
agcttatctg tgaatcaaat ctgacataat ctcttttaat gtgtaggtaa tttcttatat 110880
aaattgattt tttggccttg ctgtcagcat gcatttcaaa ttttacacca tgtgtttggg 110940
gagctatggt ggaaattagt acattaaaaa tgtctacaga gccaattagt gtataagcag 111000
ggaggcaaac taagggaatg gtggaagaaa ttaaaaaaaa aggggtgtgc ataatgtgct 111060
tcttctctta aaaaaaaaaa aagaaaaaga caacaacaaa aagaaagaaa aatgacattt  111120
gacggtcatt ctaccagtag tcatggggca gatctatatt atactgtact attacgctgt 111180
tttttctttg caattagtga gttgcttttc caggatagaa aatttggatt agacctctgt 111240
ctgtgcctat gaaaacaagc agagctaact taactccttc tcatcagttc taaccaactg 111300
```

```
acatgggcat taaaaaaaag attttatcta ctaagcaaat atgatcacag tctgaagctt    111360
tgttcttgga aaatcccctc tcagggtgtt cagcctttct tcttcagctt gcagaattct    111420
ccatgtttca gtttcctgat aaatcagtgg gcgccgctac tccacatctt tgaagctggt    111480
tgttaagaag cagtgcttct gcagcaatca cagtttaaag catgaatcaa tttaacatca    111540
cacaagctat acatttcaac agagttacag tttcagagta aagtgcaata tacagtataa    111600
agcgaatctg gaattcaagc ccaacaatgt cataaaagag gctgtgaagt ctcacatgat    111660
gtgggccaca gagagggttg ttgccattgg atcttagctc aaatactacc acatcttcgg    111720
agtggcctgc catgggccac ccttactaag gcaatccctc tgtccaagcc aaaatgatat    111780
ctcggacttt ttttgaattg cagagagatt gttgcagcca gggattgcct tagtaagggt    111840
ggcccatggc gggcctctct gaggatgtgg taatatttga gataagatct gaatggcaag    111900
acttcagcca tgtgaagggt ggagggattt ctagggaaag gggtcagcac aggcaaagac    111960
cctatgatgg gaagaagctg ggcacagctt gggattgaat gaatgccaat gtggctgaag    112020
ggtggtgatt gaagaggagg gggagacgag aaggtctgga aggcctgggg catgatcaga    112080
tcaggtgctg aggccgtgga agtagatggg attttcatct aagggaaatg ggaagtcatt    112140
agagagtttt caggagggga tgatatgtat ttttttaaaa ttgagcatta tcctcggtaa    112200
acttttgtag tcgttaaacc agagattata agcaggtttt acctcatatg ccagttgcag    112260
ctgattagta gtggctatag agaatcctgg gctgagaagg atactgtggc taaccagaat    112320
tcagtagatg agtttgacgt ggcctgttag tatgactaca ctgtgtgcac tgtttctgca    112380
ttaaatgtct gataaaaaca gagccaaagg aaaaatagaa cttaaaaatt taattctgac    112440
agtacagttg acccttgaaa acataaagg ttggggtgct gacccttgt gcagtcacaa    112500 atttgcatat aactttttgac ctcccccaaaa aactgaacca ctgatagccc actgttgact    112560
ggaagcttta ctgataacat aaacacttga ttaacacatg ttttatatgt tatctgtatt    112620
atatactcca ttcttaccat aaagcaagct agagaaaaga gtattttatt taaaaaatca    112680
taatgaagag aaatatattt aatcttcgtt aagtagaagt ggatcattat aaaggtcttc    112740
accctcatca tcttcacatt gagtgggctg aggaggggga ggtagaggaa aggttggtct    112800
tgctgtctca agagtggcag aggtggaaga aaatttatgt atatgtggac tcatgcactt    112860
caatcccatg ttgtccatag gtcaactgta gtttcaaaac cagcttttta ttactgaaaa    112920
tacgggaaaa aaaactcaga gaagaaatgg aaagtttgct atgatccagt catacagaga    112980
aatccatgtt cagcctgttg atgcacttta aagaaggaga tacgtgggta aaacctgatg    113040
ttgaattact cttacatgat tttggacttt tgcaggagct tgtggtgctt tgccacctcc    113100
accaccccag tttgatatct ttgctggcag ctgggattcg tccccggatg ttggtgatgg    113160
agttagcctc caagggttcc ttggatcgcc tgcttcagca ggacaaagcc agcctcacta    113220
gaaccctaca gcacaggatt gcactccacg tagctgatgg tttgaggtaa gtaggtcatg    113280
ttgttttcta ttcagtgcat gacaagtgtg atccagactt gctctcaggt tctgagaaca    113340
cttcccagta acactgtgcc ccagtaacaa tttataaaca atttggatga aaactaccat    113400
ttccctgatc aaattttgta atttcagaaa ataagagtat ggaaaccatg cagaacctca    113460
tagcaagtag taatagactt tgaacccaca agttctgctc tagaacccat catcttaacc    113520
ctgtactgat ctgccttcta taaaaatgta taagttaggc ttcacagtat caaagtaagt    113580
gtcaattaca tgattccaat gaggaaagat gagtccatac ttctcaaggg gactagagtg    113640
attcatgttg gattcttcgg catgaccatc tcacatgtct cagaggcaca cctaaccctg    113700
```

```
catccagagc aagctttgga gagggagcac actggagtgg aaaggctgtg gtctttgaag   113760
acaaaaggcc tgggattcat cactattcca cacatttagt aactgtgatt ttatatctct   113820
gattcccatt ttttaaatag tctgtgaacc atgactaata tttaatgcat aaaattatga   113880
tgacttctgt aataattgga gacattccag atgaaactct tgatgtcccc tctgccattg   113940
ctccccaacc ccagtcaccc tgttacacct gagagtcacc ttacattcct ttcttcctct   114000
ctcatttcac agctaatcct tcagcaaatc ttttcagctc tgccaccaaa atatatctta   114060
atgcttctaa caatttctct cactaacgtc taaatctgag ccagtatcat ctctcattgc   114120
ctactggtcc cctgcttcta cctctgtctc atgatagtcc cattcctcac ccagcctctg   114180
gagtgatttt tctaacatga aagttggatc aggacttgtt cctgttatta cccctcccct   114240
gccttatttc ttgggtacag tgctcagcca ctcccatccc tgaggttcct tgcagatacc   114300
agaggcttta tatctgctgt tgatttcact caggaatgtc tgactcccag atgtgctctc   114360
tacttattat aaaggattat ctgaatcttt ctgaatcctt tcatttagga ctctcagcag   114420
agaggatgtc cgcaacgacc ctttgtctct ccagccccta taggactatt gctgcctagg   114480
attctttatg ttttcatttt ttaaaaactt atttattgtc tgtcttgcca tcagaatcta   114540
agtaccatga aagaagggac ttttcgtctt gtttgccatt gtatctctag ctcctaaaat   114600
agtaagcctt cagaattact gtgttgacag taggggaagg gggagaaagg aggaaagaag   114660
gaaaacagtg cctggggcat agaagccaag cagtgtatgc aactttcctt ctcttctttc   114720
tcttctgaaa tgctatgaat atgccttta ggtagtatcc agaaatgttc cttcctgaaa   114780
gggtccagaa actactgaaa actgtacaga ttatgaaatg aaacagggtg cagggatttg   114840
gatttgagtt gatgtttctg cttttgaaca ccagggggaa tcttgggtta cattaatcta   114900
ggtaaagtgc agaatagtct cctgtatttc agtgccctct ttccttcatt taactaactc   114960
taggttctag ttttttccta attcttccac aaatccccaa agtgtttatt tataaagtga   115020
agaattgcta ttttttaaca ctgttcgaaa caccttatct ctaaaatgac ttattctagt   115080
tctctgaaac cttactttaa ataacaaatc cagcagtttc tgatgaagta aatgaaatgt   115140
cagcatattt taaaataatt tgcctaattt gttcttagca taatgccaga aaagctttct   115200
ggattttgta tcacaaaagg ctagtagatt tcagtagcta tcaatcttct accagcacta   115260
agtatatttt aaaaactcag cattaaggtt tattttccca agtatgtttc agcacaggaa   115320
ataaaatcat gctcctttgg agtcccttaa atgctggagc tgtttagagt gacatacaag   115380
aactttcttc acgttacatg ctctctcttc ctccatcttg cttttaactg ttagcttact   115440
tctccaattc aatccacttc gtttgaactc tttatcataa ttctataaaa cttatgaaaa   115500
tacagtcaac tgcattttct gtatgtttct gtgtttcaat atcttcaaaa tggaatgtac   115560
tgccttggta catcacccac tatgaatctg ttatttctgt tatatcccac agttgccagg   115620
ccaggatact tgtcccatcc aggccaaaca ccttcccccg aaagcaagta tgcatttgtc   115680
caccaggtcc ttgactctat tttacattat cttttagtc aattcattta tttttatgcc   115740
actcctgctg tcttggttca gtatgtccag ggaattatca gaatttcttt tctaaaataa   115800
aaatctgttt atgcttgcaa ttccttgaca gttctcaatt atctgcaaag tgcatccaaa   115860
cttcttggca tagcatcaaa gatctttctg tatgcctctt gcttcccttt gcggcccctg   115920
ccaccccact gcccacactg cattctagcc gtgatgacag gcttgaattt tcagttatgc   115980
tcatgtctgt ccatcattgt atttgttatt cctctctttc caccaagttg tctgcctaga   116040
```

```
gagctcattt tccttaagaa tttcttcaca aaccatctct actatgaagc tcaagtgtgt   116100
catgaagtgt tagcttctcc aacttgtgtt tcttgcagac actctgtgca agacattgac   116160
ttaggtgcta aagagggaaa gctagatatt atattgttct tgaggttgaa agcttacagt   116220
ctagtaggag agtcaacttt gctgtcttta cctcagtgtt tttctccctc tgtgcttccc   116280
tagcacgtgg tacttacata tttctggaat cttgattaaa cacctgtttg aggactgtct   116340
gagcacaatc cttctggatt gtgacaccct caagggagca gagatacaaa gatggctttg   116400
tatactaaat gactggccct catagatacc tagtacatat ttgtcaaata aatgaatgca   116460
ttctattttt ggaataattc tattcagaat cagataaagt ttactttaag ctatgaagaa   116520
agaagtctct tagcaactct tacaataatc acaatcaaag aatgactgtt taacttaata   116580
taaaccagtt tgttttaata aaatatttga caatagtcat ggttacacaa tgcataaatt   116640
atggctaaat tattatcagg aaggaaaaat ctttacttat tatttcaaaa gctattttgc   116700
tagtctatta aaagctatta gaactgcact tcttaagatt aaattctata attgaacatt   116760
ttaactaacc aagatattat ctctttgcca ctgacattat ttcaaattaa gcttaactat   116820 ttcttttttag cctttggaaa gtattctgaa agagtctgtg ttctataaat atacttaaag   116880
aggcatgtct tataaaggat ttggatacta ttcaatgatg tatgacttgg ctttagcttt   116940
tttattctta atctctcagc ttttctcttc agcagggaa gagtacctaa tggcctttca   117000
gtaatccctt ggtaaatttt tctttcaagc ccattactta ctgtgaaggt caacttcatt   117060
agtgtattta tcttattttt ttcagcccaa aataggtata ttgaaatgaa tgggcctaat   117120
gtcaaatgtc ccgactacat cctggaagag agagaatctt cagctgtatt agttgatgca   117180
gttaaataat atgtactctc caggccctca tacaattgaa agttcagggt atcgttgctg   117240
ctctgcttct aatccttcca gaagtgattg gtgctaggtg atggagtaac tattaattga   117300
tataatgtga gccaaaacca acagtcacga ataagcaaag gatttaaatt taactccatt   117360
aagtcttgtg agaaattatt ttcaacatag gttataacat acctgtgaca tcacatgaaa   117420
tgctgtagtc aatttgacat catggggcag agaagacaga gttggaaatc agaattttat   117480
agacatctaa tgtgataata acattagtag ctgagatgcg gtaagctctt tgaccatgtt   117540
tccagaatgg ataagacctg gttgagatga aaactttaca ctgtttttt atattaacta   117600 tcttttactc tttgcctgaa atgtccaact ctagttgctc gtgattgcgt gggtcagtct   117660
ccagaaggtt ggactttaat attcccgtc atcttttcca agacaaaatt gtattcattc   117720
taactcttag ccccaaattt tctttttta ccttaatatc taacatgatt aggtttatgg   117780
taaattatat actcaaacag aagaagagac taatagcaag caaaagtctt atattttcat   117840 ttgtttcat ccaaaagta gaaaatattt tccaaacatt gggaaacatt ttagtcagaa   117900
aaataaatat caatgataaa tagaatagag aaaaatttta aagctgagct aaacctctat   117960
gtggttttag gaaatcaaa actattaaat aaatggcaag tacaacaaaa tcccatcaat   118020
tcttatttaa catacttaca ttttgaaata gttaaaatat tcatatgatc attgagagaa   118080
ttcagaattg cctttaagta attgttcaca tatacaaaag aaaagtctcc aaaaattggg   118140
tctttgcctg agatagattt gtcttaaaat tgaaatcatt cacttatcag atttgaccct   118200
tttttaaagc ataactttgc tgtgtaatat tagacttata tgttttgatt tccttctaca   118260
atatctctta actttaaggg acaaagtgag cacagaattt ttgatgcttg acatagtgga   118320
catttatatt taaggaaatt aggacaaaaa ttattaaat gtaatcacat ttgaataaga   118380
tttcctgtgc attttctggc agatacctcc actcagccat gattatatac cgagacctga   118440
```

```
aaccccacaa tgtgctgctt ttcacactgt atcccaatgc tgccatcatt gcaaagattg    118500
ctgactacgg cattgctcag tactgctgta gaatggggat aaaaacatca gagggcacac    118560
caggtaggtg atcaggtctg tctcataatt ctatcttcag gatggataac cactgacctc    118620
agatgtgagt tcagaagagt caaaaggaaa acagagtcta tcacattgtg aacagaggtt    118680
tattttgtga aaaatgcaa gcatcacatt gtgatttta tcattgtatt ttgtaggaaa    118740
aaaacaattg atgtaatttt tcagggcaaa aactgaataa aaagaagaga atgtttgata    118800
tcaagttata tgttttaaag ttagatttgt agattcttta gatactctag aggtcataaa    118860
aagtaacagc aaaaacttta gtctaggtat tgttggcact tgtgaggcaa atcaaattca    118920
ggtccacaaa ttcttttta taattctgaa acccaaagaa ctctgaaaat cccaagattt    118980
tttaaaaaat gactaatttg gtgtcaaaac ctaagcaagc tgacttgttg cttattacaa    119040
tctttatttc tcatgctcag tgtgaatatg catacatttt gctgcagaaa tatatacatg    119100
tttgagtaca gggggctggc cgtgacccta ctgagggttt ctgtacacat cactgtctac    119160
cctgtggaat cttacctccc tttcttagtt cccaatcctg aaaagcagtt atggggccag    119220
tgctctgtac agacatgttg tctcagacat cagtttgagc aggaagtaaa tcatttaggg    119280
gttggcattt gtttggagtg tggggaacac tctatcttta gggaaacttt atatagttag    119340
ttatttgtaa gtaaaattac aggtggctat acatcatctt gctgattgca actcaattaa    119400
atcaccgtgc ctggcacaga agaaaatatg ctacaggata tctcactagg gaaaaggttc    119460
tagttcgttt cctgcgcact caacttttgt acttagataa gcaaatggcc ccagattcca    119520
atgcctggtt ttattttgc tccaaataca tatatactct tttgttttgg atagttacat    119580
tttagaagta gactgtgtat tctcataaac acttcaaagt gtatgttctg gctgagagtg    119640
tctctgtgtt gttcaataat aataagacta attatcattt tttgagtacc tgctgtgcgt    119700
caggcccagt gccacgtata ttagagacaa gatctcttat cctcatgcca gggctggaag    119760
ttagctatta gtttctcatt tgccaaatga gaaaactgag gctcagggag attatgtaac    119820
ttgcagaata tcactcagta attggccaag ataagaattc agtctaaatg agaaccagat    119880
ccagagatat ttggctttaa attctatagt ctctcctaaa ccatatgcaa ctctaacatg    119940
aagaagctta tttaatcttc actattaaaa aagtcaaaac aaaacaacag agccatgaat    120000
agcaaatatt gtcaatgaga ggtttggaaa aacagtctta aaggatgaaa ttccatagac    120060
ctgatatatt tccacctgga aaaagtgggc atgggacagt gattttctct tgaaagatct    120120
gctcattttt gtcatgggac atgaaggtgg actggaccac tcagtttctt ctttctgcat    120180
ctcccaaccc agtctttctg ttcatggggt gaaaatctgt tgttgaagcc ttgtctgctt    120240
aattggacag tggatctctc gggtcccgt gggctgtgcg cttgtacttg agctctgctt    120300
cttcactctg tggtctaggc cagctagcag ccagctgagt tcaccttggt tcagactcat    120360 ggccttcat tttcagtatc tgacttcctg gttttgctga aaacctgtct aaaatgtaat    120420
atccatctga ttcttcatac caagccacac aattcttcct gatcccttt aatctccaat    120480 attgaatggt ggtaacataa atatggagac agatcatgtc agaaacccag ggcctaatct    120540
tttcttttct gcctactctt ctcacaggct gcttagtact ttgtaagctt ttttttttt    120600 tctggctgta acctagattt tctctttatc attactctat ttattattgt tagagcactt    120660
ctgattatct cagccctaaa ctctgcctcc aattttaaat aacaataact cccactcctg    120720
ctaatactgc tactactact accatcacca aacttttct tccccaaagc agttctgttt    120780
```

```
gggaaggaaa cagttccctc tcatacaatt tcagttatct tcttgtcttt tccgtttaat    120840
gaatcttcct gttaatgtta catcttttaa catggaaact tctagagaaa caaaagacga    120900
tggatttgtt aaacctttg ggtgtatttt tatactaact cttactgcag cgtgtgcatt     120960
atgagtgtag gtccattacg gctgtattag gagcagaacc ttccagagca tgagcgatgt    121020
gctgggcttg tgcttagctc tatccatgag ttaagtatct caatccttag gaccctctga    121080
catatgtgct attattattt ctagtctata gatacagaga ctaaagttta gagaatataa    121140
aaaaacattt acaaggtcct atgggacaaa aactgtagga caaaatgcaa acccaagcag    121200
cctgagagca gagctcctgg tccagcactg tgatagctgg ggacgcagag acagaaacaa    121260
tgcaattatt gacagggacc atggtgctgt gtctgtccac attttgaaga taattatggt    121320
ttggatattt tcacctttaa ataacttgga gagtttcaac attaactcag tcagatggat    121380
acatttatat catatcctgc tgggagtgac agttaattct gggtcctatg gcaattgcac    121440
ttttgactga gatgaatgct gactgatggc tttaacattt aactaatgcg atagtattta    121500
acacacccat ataaatacta tagtcttcgg gtaaataaaa tgttaccggc tggacataca    121560
tgaatatctg atggagatta tggaacatac tctactcata cttctctgaa agtaaaaaat    121620
aaaagatatg tttcagtaca caatgtgata tgtactcaga cttaattcat aaatttctct    121680
tatccttcat ccgtggatct tttctttatt tacttattgc gtttgttaaa atgcaggctt    121740
ctctgaaaaa ttattttaa aaatagtttt tagacaatga atcatatttt ctcaagtatt     121800
ttaacattgt aatcattatg ataattatcc aaggggaaat tatacttatt ttttattcat    121860
ttattcattc atttggcaac aatacattga acatttacta agcatcaaac tggctctacc    121920
acttaatagt ggcatgatgt tcatcaagaa attgttagtg caatcaagaa cactagaaat    121980
tcattggatg aatttaaaga agcttttaga agggtattat attataattg aggcacttta    122040
tgaatatata aataatatta tgttttcatg ctagagatca tgccaatgaa gatatttact    122100
ttgaaaagga gaagattaga agtttaaaag cattttccata ttgaagtaaa tattcatttc    122160
catatcttca cagttatctt tctctgagtt ctctgactca ttgtgaaaaa aaatcccaac    122220
cttcttcaca gctctaccat cttcggattg ttgcctagag gggtaaaaac tattgtaaaa    122280
ggatgtgtgc actggatgag aatttagaat tagacgaaat gaccccctaga gtctttcct    122340 gctttaagag cctgtgattc caaattctaa cagtacattt atcaagaaaa aatatgctga    122400
acatttaaat agttttgaa tagtacctag atataataga tacctaataa atgtgctcaa     122460
tgaataataa ataactggtt aagatttaaa taagcctcca aaatctcttc cacattctaa    122520
gaagggaagc ataaaggttg ttaatgaact agtgactgtg tgggtagctc attatttta    122580 agtactcttg actttgctgt tcattatctg tgtggcctta ggaaaataca cacatttctg    122640
aaaggattat gtcgtttgta aaatagaaag tccttatctg tctaccacag atgattctta    122700
tgcaaatcaa atgaaatgtt caataaggtg tctgtaaaat agtagagaga gatgaattag    122760
gagctattgt gatttgttta cattatgtca caggtgcact ttattaggga tatgttttat    122820
cttaattaca caattcttta acttagattt tgagaattat attatggtta tataggaaaa    122880
tgcccttatt ctaaggaaat gtataatata tttaggtctg aaacattgta tctgtaacaa    122940
tatagtatgt aaattatgct aattcacatg ataattatat gtaattatat taatatatta    123000
ctatgtatac aatatattta catgcatata tgtggggaaa tgttatcagt tagtgtagta    123060
ggggttatca tactcaaatt cgatgtctcc atccttccaa ctcttcatgc ttttccagca    123120
tggtgaggac tgctgagctc catctttttgc tggtagtctc tctgtcaaat agaactgttt    123180
```

```
ccaaattcag tcatttgctc cttgaaggct atgaattcat acttcgttat attttttctgg    123240 ctgcatattt aaattacttt aacaatcata taagttcatt gtaaaaattt tggaaataaa    123300
aaggaagata aaatgcacag ataattttag caaatgaaat aataattata ttgggatgta    123360
tttcttccta gattttaatt atgtacattc ccatcaactt tttatttttga aaatgtttaa    123420 gcctaaagaa cagttgaaag agtagtacag gctgggtgca gtggctcctg cctgtaatcc    123480
caacactttg ggaggccgag gtgggtggat cacttgaggt caggagttca agaccagcct    123540
gaccaacatg gtgaaaccct gtcactacta aaaatacaaa aatcagctgg gcacggtggt    123600
gggcacctgt aatcccagct actcgggagg ctgaggcagg agaatcgctt gaacccagga    123660
ggcagaggtt gcagtaagcc aagatcacac ccctgcactc cagcctgggc aagagagtga    123720
gactccatct caaaaaaaaa aaaaaaaaa aaagaaaga aagagtagta caatatacat    123780
tcatactcat atacccgacg cataaattca ttgattattt acttttttgcc ctacttgttc    123840 tttcttgctc tctttgcgta tgaatgaatc attgaaatta agttgtagac atcatgccat    123900
atcacctctg aacagtgtgt atatttctttt agaataagga tgtttactta cataatcata    123960
ataccattat cacagctaag aaaattaatt cagttgattt tttccacata tttgataact    124020
ttctgtctat ccacgattat gtcttacata ttctttttaat ttatgtcata gcatatcatc    124080
ttagaaagtg atccctaagt tactgcatgg tatacattgt ttaaccattt ccctttgtga    124140
ttggatgtct ttaggttgat tatattttta ttattatcac aaatgttgaa atcactcttt    124200
ttttctgaag aatttaaaag taatttatct gtcttatgga ataaaatatt tatttcccct    124260
taaaagaatt tcaggcatga acccaagaga gaaggcttttt ttttttgttt tagttgttgt    124320 ttttatttttt atttttttatt tttttgggtag aaggagcaga gagacaagtt caggaaataa    124380
tgagagtgtt agaattttgt tcaggttaaa gtgagttgga gtgaagttta gaaatctcct    124440
ttctactcat ctctcctgtt tttaaaacac tgtcctggaa atagttaata ttaggaacga    124500
gaaaaatggt ataggttttc ctagtacact ttatttctta attatgaaat tctacttaat    124560
aacttaccat tgaatgttta tccttattat cattcaaggt aatttttattg aagattgaag    124620 atatttataa taaagattga aggatttttat tgtcctgtgt ggtcaacctt gggggggtgag    124680 atgttatgag acaggacaat taattgactt gatcaaggta ccttgttata aaataacac    124740 agcctggttt agaacatctc ttcctgactc tcttatttgg catatagcct aagtgtatgc    124800
ctccttggat gtatgagccc tgatgttggt catatttatt attttatctg cttactttca    124860
gggtttcgtg cacctgaagt tgccagagga atgtcattt ataaccaaca ggctgatgtt    124920
tattcatttg gtttactact ctatgacatt ttgacaactg gaggtagaat agtagagggt    124980
ttgaagtttc caaatgagtt tgatgaatta gaaatacaag gaaaattacc tggtaagttc    125040
tgttttctct acaatgaaga tttttttttct taatatcagc agcttcattt ttatttaatt    125100
gtagttgtat gcttaattcc ttaaacagat gatcattttt tttgtttagt gcataaatat    125160
tcttaaatct tgtgatatat aataaaaaat cacctgaaaa aggtagcagt tttaggctttt    125220 ttaaaaaatc cgcaattaat attggtgtag ttaatattat atttagaaac atagagaagg    125280
aaattgctgt tagaactcca catttggtga tttttaattt tcataaagaa ttactgtgta    125340
ctcattatcc tggaatgttt tcgttttctt ggagtgaaat aatttacatg caggaatgga    125400
agactgaatg atctataata ataatttttc ataagaatcg gtaaatgtgt atttaatgtt    125460
atcaaagctc atttggaatg gttgtctcat gctttcaaga aattagagga ctttgtaatt    125520
```

```
cattccttaa ccattacttt agttctcacc acaaaataac attttaagtt tatttagctc   125580
tttctcatat tttctgcttt cccttttcatt taaaaaatac ttttgagtgt acacaatgtg   125640
ccatgtacag gaaatagagc tttatctttt ttgggtataa cttcaagatc atggcaaaag   125700
aaaacttatt attaattgga taaaccttag atataatcta ggttatttcc cttattttac   125760
tagttttcta gtgaaaatat tcaggtctct gctgggtaca gtggcttacg cctgtaatcc   125820
cagcactttg ggaggcccag gcaggcagat cacttgaggc caggagctgg agaccagcct   125880
ggccaacatg gtgaaaccct gtctctacta aaaatacaaa aagtagctgg gcatggtggc   125940
atgtgcgtgt agtcccagct accaaggagg ctgaggcacg agaatagctt gaacctggga   126000
ggttgcagtg agccgagatt gcgccactgc actccagcct aagcaacaaa gtgagactcc   126060
atcttaaaaa aaaaaattca gttctgtgtt ctgcatcaac cagaataagc tacgcctctt   126120
ataaaaaaca aatgtgcaca aaccatctgt gaggacataa ggattaaatg cttgcttact   126180
ttgagtatta aaataaaaag tagaagcttt attatatgag taaaagtgtt tccaaagtct   126240
atttgaaatg caggtacaga atgaaaatct gttattttat taaatcgtta tttgggtctc   126300
tttttattcc ataaaaaaaa aatcttttcc acatctctta gtggagatca agttaacaaa   126360
attagcttta attttgtgac aagtaaattt acataaaatat aggattatgg agataatatt   126420
tttctttgca atgtctggac ctttttataaa cattgagagg aaatataacc attcttactt   126480
atttagtatg ctagcatgat gtttttttaat gtttttagatc cagttaaaga atatggttgt   126540
gccccatggc ctatggttga gaaattaatt aaacagtgtt tgaaagaaaa tcctcaagaa   126600
aggcctactt ctgcccaggt attcttaaag ttttgttaat attttgtaca gaacatcatt   126660
tgcatatatg catatatata taatcttcaa atatatatac ttaaacacat aaacacacag   126720
agacagaatt aaaaatagtt ataaggcaaa cctcctataa ttttcaccat cccaggcaca   126780
aaaaaaggac attgccaaaa cctcacatgc tcccatatgc ctgtctcctc ttctcttctt   126840
tgaaatgcct gcccattatt ttgcccattt ttctgttgac tcttttgcct acaaatcaaa   126900
tcagaaaaaa attttttatat ataacatact aatcctttct tggttttata tgttgcaatt   126960 tcttttttcga gctggtggct tgcttttttaa atttcttgta gggtgcccgt taatgaatgg   127020
aatttcttaa ttttaatata tataaattta acaattcttc tttttccttc ttttcctggt   127080
tattcctatt tggtcctgtt gtagagccca tctttctttt agagctacaa aaatatttac   127140
ctgcaatttc ttcaaacatt ttaaaagttt gcttttgaca agattttaat ccattggaat   127200 tgacatttttt atctgtatcc cattccttttt tttaatgtgg aagactaatt ttttcaggtt   127260
gatttactaa atggcttctc ccctttttgtc ccatagatct gatgtgtcca ttttgtaatt   127320
tattaaagat aatgtgcata tccacgtgta cactgtcttc cactgatcaa ctcatttatt   127380
tttcctccag tattaccctg tcttaattcc tgtagcttta taatgatctc ctctccctat   127440
ttatttttct catccaggaa tattttaacc agtcttaggc ttagcttttc tatataaaat   127500
ttagaatcat gctgtcaaat cttatgaaaa accacattgt cgtttggatt ggtcttggat   127560
tgaatatgtt gacaatctgg agatgatatc cttatgatat taagtctttg tattctttttt   127620 cttatttatt tatttattta gaggcagggt ctcactctgt cacccaggct ggagtgctgg   127680
agtgcagtgg caggatcaca gctcaatgca gctttgacct cctgggctca agtgatcctg   127740
tcgcctcagt ctccatcagc caattgtgtg ccaccagacc tggttaactt ttcctttaat   127800
ttttttgtag agaaagggtc tcactctgtt gcccaggctg tcttgaact cctgccctca   127860 agcaatcctc ccgcctaggc ctcccaaagt gcatgagcaa ctgcacctgg ccaagtcttc   127920
```

```
ctattctgga atggcatgaa ttctctctgt ttacttaggt cttctcaagc gtctttcaat   127980
aaagttttgt aatgctacat acaggtcttg catatctttt gctggatttt cttgctgcaa   128040
attgctttaa atgcagttca tggcttgaga tttgttttt aactgcccag ttaacgtaaa    128100
tctggtctat gaattgtatt gacaacaagc ttgtgagtag caatttttca gcaacctttt   128160
gctccctctc cccgctccct gcacagtccc agaacaactt tccttatata ccaatgaagg   128220
tggaaatgtg gacaggttga tttctccttc ttgtttatgc tgaatatgca gtcctttggg   128280
gtcccagctt tataggtaca gtccctttac taagactgtc tatcttggga aggccctaga   128340
ctccaacttc tctcccatgg gccccacaaa gcatccaaga gtatacattt atattatctc   128400
actttgtctt ggcagacaaa tgtcttcagg gcaagtctgg ctttaggggt ccactgacct   128460
ctctggtttc tgtctctcac tgtgatttcg gcctgataat tccttatggt gtcagatctt   128520
caatgttttt aatacattgt ttttaaaaaa atcatttagc attttaaatt gttttagtt    128580
ggaagatttg cccaagtaac cttgtccacc atattatctg aaagagaact cttgtcatgt   128640
tttacactga tacacatttt aataaatgtg ggttatcttt atgttgtgag ctcttgattt   128700
ggtattataa ttaattggaa aagttttaac tttaagtatt ctgatcaaaa tagtcaagta   128760
caactataat gactttatca aatattacat aattttctt ctacttggtt tacttgtttt    128820
ttaatttagg ttaccatcaa tgttagtcac atgaactttt atattatgt ccacagtaaa    128880
aattttcat agcttgttgt ttttctttct tgtttttca ttttcaatta tacttaccct     128940
atacttaaca gaatacttaa caaatatgta tatatgac aatattaaaa agcttagaca     129000
tacttatttt atgtttaaaa tataacatat actaggcaag acaggaaaac tcatcacttt   129060
tatgaaatga ggcacagaca gagtaatggg cttcttggt gtctcctgag tggcgggcag    129120
gtggccatgt cacagctcta atcccagttt cctgacttct ggttctgttt tcttacggtg   129180
ccttcacact gtctctccag atcaaaaaca gaatctagag atgacttcta aattttgtta   129240
ccaaagactg aaattcctgt tcctttcaac tactagaagc tcaactaaat tgttggccca   129300
agggttttc tctcactggc ggtggctctg caatatagaa ttgcatgcag agtacctcct    129360
gactccgcta aaatcctgtt taattgaccc ttgagatttt cttttcaagt taaaaaaaat   129420
actacacata ccaaagagta tcaagcacag tttaaaaata catatttgtc ttttcatgta   129480
attttatttg tagtttagat tactaatctt ggtgatctag ttgggttcca gtttaacagt   129540
tttaggtttt gcttgacaga gctataacac ttcagtctat atttgatttt tcaagggaaa   129600
tgagttaact cgataagtac tgttttgtta tcttaaact ttctcaggtc tttgacattt    129660
tgaattcagc tgaattagtc tgtctgacga gacgcatttt attacctaaa aacgtaattg   129720
ttgaatgcat ggttgctaca catcacaaca gcaggaatgc aagcatttgg ctgggctgtg   129780
ggcacaccga cagaggacag ctctcatttc ttgacttaaa tactgaagga tacacttctg   129840
aggtaaatcc aaatgctctt taaatctttc ataatttaaa gcatatacca tttggaaagt   129900
tacttaggaa taaattaaat aagagccaat gtaggattat tattcaatta gccttctgtt   129960
agaacaagag tattcaagag caaatgtgtt ttgctttaga atcacagcat atgtcttagc   130020
tcagggtccc tagaaacaga gcctgagatg ggttatcttg cacaagtgat ttaaggaaag   130080
agaatcttag agagaagtag aggaagccag aaagggcaga ggaaaaagct cagcagaaat   130140
gtggtttctg aagaggtcca gcctcagtct ctgcccacaa ggagctctgg aatatgaata   130200
ggagcacaga attttcccac tgccaggcaa gggagccagt ctttcattct cacatattgt   130260
```

```
tcagtcattg gctgcaatct gctgggaggt gggggtagtg taactttcaa ggcatttctg   130320
ggcaagctgc ctcctgtcat ctgagggtat tctgtgataa atagcacatc tctgaactat   130380
agtagccaac actcagggta gctggggatg gcgtacctga tggataaagg agatctggac   130440
atggctccta aaagtggatc aatacattgt gttggcaaat ataagataag tttctagact   130500
tcaaagacaa cctagtattt tgactgctgc ctgaagataa atattgtgcc tcaacattag   130560
ttctgaggtt aaacaatctt tttttttaa ttgatcattc ttgggtgttt ctcgcagagg   130620
gggatttggc agggtcatag gacaataatg gagggaaggt cagcagataa acaagtgaac   130680
aaaggtctct ggttttccta ggcagaggac cctgcggcct tccgtagtgt ttgtgtccct   130740
gggtacttga gattagggag tagtgatgac tcttaacgag catgctgcct tcaagcatct   130800
gtttaacaaa gcacatcttg caccgcccct aatccattta accctgagtg gacacagcac   130860
atgtttcaga gagcaccggg ttgggggcaa ggtcatagat caacagcatc ccaaggcaga   130920
agaattttc ttagtacaga acaaaatgga gtctcctatg tctacttctt tctacacaga   130980
cacagcaaca atctgatttc tgtatctttt ccccacattt cccccttttc tactcgacaa   131040
aaccgccaac gtcatcatgg cctgttctca atgagctgct gggtacacct cccagacggg   131100
gtggcagccg ggcagagggg ctcctcactt cccagaaggg gcggccgggc agaggcgccc   131160
cccacctccc agacggggcg gcggccgggc ggggctgcc ccccacctcc cggatggggt   131220
ggctgcccag cggagacgct cctcacttcc cagacggggc ggctgctggg cggaggggct   131280
cctcacttct ccgacggggc ggctgctggg cggaggggct cctcacttct cagacggggc   131340
agctgccagg caaaggggct cctcacttct cagacggggc ggctgccggg cagagggact   131400
cctcacttct cagacagggc ggccaggcag agatgctcct cacctcccag acagggttgc   131460
ggccgggcat aggctctcct cacatcccag acggggcggc agggcagagg cgctccccac   131520
atctcagaca atgggcggcc gggcagagcc gctcatcact tcctagacgg gatggcggcc   131580
gggaagaggc gctcctcatt tcccagactg gcagccggg cagaggggc tcctcacatc   131640
ccagacgatg ggcggccagg cagagacgct cctcacttcc cagacggggt ggcggccggg   131700
cagaggctgc aatctcggca ctttgggagg ccaaggcagg cggctgggag gtggaggttg   131760
taggtagcca agatcacgcc actgcactcc agcctgggca actttgagca ctgagtgaac   131820
gagactccgt ctgcaatccc ggcacctcgg gaggccgagg ctggcagatc actcgcggtt   131880
aggagctgga gaccagcccg gccaacacag cgaaacccg tctccaccaa aaaaatatga   131940
aaaccagtca ggcgtggcgg cgcacgcctg caatggcagg cactctgcag gctgaggcag   132000
gagaatcagg cagggaggtt gcagtgagcc gagatggcag cagtacagcc cagcttcggc   132060
tcggcatcag agggagacgg tggaaagaga gggagaggga gaccatgggg agagggagac   132120
ggagagggag agggagagga acaatcttct tatatggttt gaaggaatga gaattcacac   132180
tgaaaaataa ttttaattt tagtttcaga tgtcatcttg ataggcaaaa cttgtctgcc   132240
aattaactca tttattgctg aaaattaaat aaaattggca ttgttttttaa aagtaatgca   132300
agaaagcaaa aagagttatg ttgataacag aatcctttat tctgtacaag ttctagttgc   132360
ttaagcttaa atcaaatcct gctaagtata ttttctttc ttaacaggaa gttgctgata   132420
gtagaatatt gtgcttagcc ttggtgcatc ttcctgttga aaaggaaagc tggattgtgt   132480
ctgggacaca gtctggtact ctcctggtca tcaataccga agatgggaaa aagagacata   132540
ccctagaaaa gatgactgat tctgtcactt gtttgtattg caattccttt tccaagcaaa   132600
ggtatggtag tgaatttgat caatggggaa attacagatc ttttaaacga ctgaattgtg   132660
```

```
tgcataattg ttattgcatc agcaaagatt gttcattttt agcctatttt cattggtttg   132720
catatattaa agggaattgt ggaaggtcac agagatattt gttgttttc tgaatacaga    132780 tctagctgag acatttataa aataagtcaa ccatttattc aggcctacca gccctgctcc   132840
tggtattacc tcaactgtgg ctctatctct ttacttctcc tcagatcaat gaatctttgt   132900
agggcctctt caaggataaa ttctcattca ttcattcttt gaaaaaaaa aaatatatat    132960 atatatatat atgaaaccca ttgtgtgcca ggcttaaaca taccagttat ctaactacca   133020
aattaagaaa aaattaaat aaatgaatta ataaattctt aataggtgaa aatgacttag    133080
ctcttatcaa ttgcagggtt cttgtcccaa agaaatatat ctacatagca aaatttcagg   133140
tgtgagttgt aggttggtga ctgtaatatt tggggcagga tgatttccag gaggcattaa   133200
gattataccc tatatatttc tctggtttaa gttagtattg gaaaaaaagt actagaaaaa   133260
tgtgaagcct gttttttgta cctgaaatat caactccact ggcagtttcg gagttgaaat   133320
tatttgaata tggtcaaaga aaaatttcaa tggatggaat tgggcaagga cgactttatt   133380
caagcctatc acagcagggg agagagatca gactgaacta aactccactg aaacaaaagg   133440
tgggagagtt ttaagcgcag gggtgagcta atggaaacgt actggagcac cttgttggaa   133500
ggaagtggga gcagttgtca atgtgattag gccatctgtg tttgctaatt gtcccttatt    133560
gaaggtaggc tcctactctc ccacagacac tggggaattc cttccttcct tccatccctc   133620
cctccctccc tccctccctt ccttccttcc ttcttctttt tttttttttt gaaggagttt   133680
tgctcttgtt gcccaagctg gagtgcaatg gcatgatctt ggctcactgc aacttccacc   133740
tcctaagttc aagcgattct ctagcctcag cctcctgagt agctgggatt acaggcgtgc   133800
accaccaaac ctggctaatt ttttacattt ttagtagaaa cgggatttca ccatgttagc   133860
cagactgatc tcaatctcct gacctcaggt gatctgccca ccgcagcctc ccaaagtgct   133920
gggattacaa gtgtgagcca ccacgccagg cctctgtctt gataattaca tttcaaagga   133980
atggctccca ggtccttgga aaagacattc ttggggtata aaactgggaa gagtctggga   134040
aaaggggcag agaaagaatt tataattcca agtcttctaa agtaaatact ctaagaaaag   134100
ggaggttagg aatttatagt tgagaagtct atctaaagtt taataaagtg gaggagaaca   134160
ttaaggccat tttagtcaac atacatgttc tttttgtaac aatttcaaca ttttccttt    134220 tagcaaacaa aaaaatttc ttttggttgg aaccgctgat ggcaagttag caattttga    134280 agataagact gttaaggtaa atgttgaatg cattctacat ctaaatttat tttaagtctt   134340
ttgttttata tatatctcac accctcttta tgggattata aactccctga gagcaagaat   134400
cataaattat gctgtatttg tattgcttca taaaatcttg aacacagtag atcctctgaa   134460
aatacttgct gattgactgt atattttata tgaatgaact aagaataaaa tgataaatga   134520
catctgattg ataatattgg gaatggaaat aattcaattt gtacataact gaggcagata   134580
attccttata aatatattgt ggaaaaaaaa caaaaatata cttaagtttt aaatatggct   134640
tgccattaac ttttcttaa gcattgaaga aatcatttaa ttttcttttc ttcagattcc   134700
tatttagtca ttaaagcatt catttctcta tccatctatt catctttggt tccatctatt   134760
cactcaactt cctacccgtt cattctccta ttgccaaaaa gcttattatc tgatgagaga   134820
cagggaagta gagtataacc cttaggttat ttcttttgta attttacat gggaaaaga    134880 atagattgaa tgtaacaata atatttcgaa tatgacctaa atttttttat gtataatatt   134940
tgtacatatt tatggggtac atgtgatatg ttgttacatg catagaatgt gtaatgatca   135000
```

```
agtcaggta tttaggatat ccatcaccat gagcatttat ttctctgtgc tgagaacatt   135060
tcaagtctcc tagttatttt gaaatgtttt taactgtagt cactttattg tactattgaa   135120
cattagaact tattcctcct atctaactgt atgtttgtac ccgttaacca gcctcccttc   135180
atcctcccct tctcccacac acccatatcc tcccaagcct ctggtaacta tcattctact   135240
ctctacctcc atgagatcaa cttttttagc tcccacatat gagtgagtac atgtgatatt   135300
tgtctttctg tgcttggctt atttcactta acataatgac ctccagttcc atccatgttg   135360
ctgtatatga catgatttca ttcctttta tggtcaaata gtattccgtt atgtaaatac    135420
acacattttc tttatgcatt cattcattca tgggtgctta ggttgattcc acttttttt    135480 ttagctattg tgaatagtgc tgcgataaac atggggatat aggaatccct ttgatatact   135540
gattcccttt cctttagatt agtatcagta gtaacattgt tggattgtat ggtagttcta   135600
tttttaattt ttttgagaaa tcaccatttt gttttccgta gtggctatag caatttacat   135660
acacaccaat agcatatggg cattcgtttt tttccgcatc cttgccagca tgttattttt   135720 tgtcttttt ataatagcca ttctaattgg gtgaagaaga tttcattgtg gttttcattt     135780
gcatttttac tgatgattag ttaatgttga gcattttttt tcatatatcc attggccatt   135840
actatgtctt cttttgcaaa tgtctattta gatcctttgc caacttttg tttttgtttta   135900 agacagggtc ttgctttctt acccaggctg gctcacagtg gcatgatcat agcttgttgc   135960
agccttgacc ttctgcactc aagtgatcct ccaacatcag cttcacgagt agctgggact   136020
acaggcgtgt gctaccatac ctggctgttt attttttgta gagatgcggc tccactatgt   136080
tgtccagact gatctcaaac tcctgggctc aagcaatcct cctgcctcat cttctcaaag   136140
tgctgggatt acaggcatga gccaccatac ccagcccttt gcctactttt aaatggagtt   136200
cttttttttt tttcctgttg aattgctttt tcgagtttct tgtgtattct ggatgaatag   136260
tttgcaaata tttcctcaca tttaatggat cctctctata ttgttgatag tttcctttgc   136320
tgtgcagaag cttttagtt tattatagtc ccatttgtct aattttgttt ttgttgcctg    136380
tgcttttggg atcttaacca taaactcttt gtctagacca atgttctgaa atgtttcccc   136440
tgtttccttt taatagtttc atagcttctg gtcttacatt taagtcttta atccatcttg   136500
agttgaattt tgtaaatggt gagagagtgg ggcctacttt catccttctg catactgata   136560
tccagctttt ccagcacaat ttattgaagg tggtattctt tctcccatgt atgctttgg    136620 tgcctttgtt gaaaattagt tggctttaaa tatgtgggtt tatttctggg tcctctacat   136680
tggtctacct acctgtgttt ttgccaatac tgtgctgttt tggttactct agccttgtaa   136740 tatatttca agtcaggtag tgtgatgcct ccagctttgt tcttttgct caggattgtt     136800 ttggctattt tggctctttt tcggttccac tcaagtttta gaaatttttt tttctatttc   136860
tgtgagaaat atcattggag ctttcatggg aatttcattg aatctgtaga ttgctttggg   136920
tagtatggtc attttaacaa tattaattct tccagtctgt gagcatgaat atctttccat   136980
ttgtttgtgt cctcttcaat ttctttcatg tttttcaggt ttccttatag agatcgttca   137040
tcatctttgt taaatttact cctaggtatt ttattaattt tttgtagcta cttcaaatgg   137100
gattgctttc ttgattttc agctactttg ttgttgttgt tgtatagata tgctactgat    137160
ttctgtatgt tgatttgaa tccttactac tactcattta tcagaactaa gagtttttt     137220 taatggaatc tttaggtttt tgagtttaa ttttaatatc tctaatcatt taagatggaa    137280
agtagttttt tgaaagcaca gatttatgg agttttgttc tgtggatact caatttgctg    137340
agtgtgtttt ctttttttt tggcaaagct taaaggagct gctcctttga agatactaaa    137400
```

```
tataggaaat gtcagtactc cattgatgtg tttgagtgaa tccacaaatt caacggaaag   137460
aaatgtaatg tggggaggat gtggcacaaa gattttctcc ttttctaatg atttcaccat   137520
tcagaaactc attgagacaa gaacaagcca actgtaagtt attttttatc tgtacaagta   137580
atttatcatt atactttgt tttttcctta taatcattaa taatactgtt gataattcat    137640
aaggaagatc ttttaaaatg cataatttat tttctatcat aaaattaaac tttcattata   137700
aaaaattttg aaaattccag aaagcagaag ggtatttta agaagtcact caacctaatc    137760
acttttaggg ataaaatatg taaactcatt gtaatcttag tagtatttat caatctaaat   137820
tttttaacaa ttttttattat ctgtgtttca aattagacat gaaattggaa gacaatcaac  137880
tttgtatttc accaaattca cggactatac atatgcaatt tgggtaactt ccattaagta   137940
ttgattgtag gaaagataga cagcaagtat tcttgcttgt ccaaagttgt ttctagattt   138000
gataattata cagatgtcta ctcacagcca agttagtgat accagtttca aacaagaata   138060
aaataaaata ttaatataaa cctctttcaa gtttgctttt tttcagtggt attttaatca   138120
aatctttgca gttggttctt atttatcaca ttcctcagtg ataagcagta taggattgtg   138180
gataagagca taaatcatag ttcagatatt gctttgccat ctattggttt tgtgaacttg   138240
ggcaataacc tttcacatct tcagtcatct cttacctgag gattgtaata ttctctatct   138300
caaagagata tttggaggag taaataagaa tgttaatata tggatcttaa ttaacataat   138360
gaccagcacc tggtaagctg tcaataaaca ttagctatta ttattattat tagctttgag   138420
tcacaaatcc ctaccttagg gaatatcctg gtttcccatt atccatcaaa tttcccaaga   138480
ttggcacttg ggagtaatct ttgactcctt tgttttttgc tcccttatc cacttgaccc    138540 tcctaattgt catttgaatc tttgtacttc tcactgttct cagtgctggt accatgggcc   138600
agactgccat ccattatctg tggccacatt aacaagagca tccagttctc accctctgat   138660
tatactctct tcaacatatt ttcagcattg cagacagagg gacctttcta aaatgtacat   138720
caatctgatg caattttcct gcttaaaacc cttcagtggt atcccattgt cctttatatg   138780
aagtccaaat tccttaagac agcctactgg gcccttcata attcagtgct tgcttacctg   138840
tctagattca tattttgcaa gcttttttgcc atctgtgctt tacccaaact gaaattgact   138900
cagatctcta agacaacctg ttattacctt tcacccccaa cctttgaatg tggtcttctc   138960
cttacctgga tgactattat gcccctgcc tatttcagtc caagcaccac ttgctctgag    139020
tggcaggtta ggtgactttg tgcttccatt gcatctaatg ttttccttca cagtagctat   139080
aattgtattt gttaaagtag tttctcaata ccactaaatc tactggcttt caacattggc   139140
tgtgcattta gaaaccacta ggtagctgaa aataatatga tacctgggcc ctacctcaga   139200
ccaattaaat cagaccagtt aagcctggga tggggatcag atttttttttt tcaggttctc   139260 aagtgattct aaagtatatt tgaggttaag atatactgcg gagtgcagtg tattataagt   139320
tcccatgaat gaggattttt atttctgtct ttacatattt atttactagt atgtggtaa    139380 catttggatc aactcattct cattctgtaa tacccacatt ttaaaaaatg aatgtaaaaa   139440
tgtcttttat tattttattt tttcaaattt aattttagat tccaggaata catgtgcagg   139500
tttgttacaa agtatagtg cgtgatgctg aggtttggaa tacaactgaa ctcacaaccc    139560
agaaagtggg catagtgctt gataggtagt ttttcatctt tgctcccctt cctgtaattt   139620
ccacttttaa cccaattata caagcctgaa aaccttaaa aagaaagggc ctccagttta    139680
tttttttatt tcatagcaca ttttatggga ttatggatat cagttaactc tttaaagttc   139740
```

```
catataagat ttggagcata gatgctttac tagagagcat ccataaagat caagctctca    139800
aagatgctca tctcccaaaa gagattggga cctagatgca taaacactta aatataaata    139860
tttgctctct tctgaacaag tatctcctgt ggccttggtc tctaccccac aaaacagaca    139920
tcacatcact aatcaggggt tgcctcatca tcagtaccct catcatcatc agtacacacc    139980
gactgagagg catgttgggt aatgaaagat gactgccttt gaagccggaa gactccatag    140040
gacttttgga gttctaggtc tgcaacatgt ttttagtcct aggtcggcaa gcatgatgtt    140100
agtcatagga ccttgagcaa attatttagc atttgtacat gtttctttct actattaaaa    140160
acattgagat ttatcatatt ttatgttttt ttattaagga tcaagcaaga taacacacaa    140220
aagtatttta taaaatacgg aaattccatg caaaactttg tcctaattgg aactattttc    140280
tattaaatac agcaaatatc caagaaggaa ttacctaaag cgtagtggct ctctgacaac    140340
acatcatatt tttacctcct tttccagaat agaaagaaaa gggggaggaa aaaaaatctt    140400
cctactctag gatatactaa tgattgttaa atctttatgg tattttcatg ttatctatct    140460
gatttaaatg caattttgac tatttttaca tattcctcgt tgttcattca tactgtagtg    140520
ccttcttcta ttcccccact taacagactg cttgattata tcagaggtgc ttatctgtgc    140580
aactgtttac tggacgaggg gtatgtagaa atacattgt cctcatcctt atgaaattac     140640
actcataatc tagtgtgagg gatgcactaa taaagacaat tttatattta ataaggtcta    140700
taatatgaca gtgacaccag tggggaaaag ggactggttg gtctattttg ataggtcagg    140760
gaagaaatcc agaggagccg acatttaagt tcatcctcaa aggccaagta ggagtttgcc    140820
atgctgatgt ggcccaaggt agccaatctg tttgtgaaat atgtacaatg ccagatgtct    140880
taggttgaaa gggaaatatt ttaaggtgtt cgtaatttt cttatgttt aaaagggaa       140940 aatggcaaat attttacttt ctgtttatgt ttggatgatg tggattttg ttttctataa      141000 tttgactggc ttaactgcaa agatatccct tgctttaaaa tttgaagaca ctgcaactaa    141060
attttatttc agcatttat attttataac tctaggtata aaaggctaac acttaatttt      141120
ctgagcattc atgaaacaaa gttttgcaag acattcaaa agttacagat ataatatttc       141180
cttcagaaat ttagatatag tacaaaattc tacaaagagc cacatagaat tgaaactaaa    141240
agtaagacca aagtaaacat tggacataat ctttatttta ttatcacaag aaattaatat    141300
aaagtaacca aaagtaagta aagtaccaaa gcatgttata tattcaattc agaatggtta    141360
gggaagaata tgaaataatt gcaatagtct agcttgttta gttttcaaaa tagtgttttt    141420
acattaagaa ctaatataag gttgtattac acgtagaaat tttaagaaga aaacaaatag    141480
tgatgacttt ctatttttt ttctctgtag gttttcttat gcagctttca gtgattccaa       141540
catcataaca gtggtggtag acactgctct ctatattgct aagcaaaata gccctgttgt    141600
ggaagtgtgg gataagaaaa ctgaaaaact ctgtggacta atagactgcg tgcactttt     141660 aaggtaaatt ctgtggtttt taattttatt cccaaaagaa ttatctttgc acttcatgtg    141720
tcacagagga aggattttc ttcctttctg cctctgaata gagaattttt ttaaaatgca      141780
gaaaaaaatt tgtaatgctt ctcagcacca tcttttcaga tcaagaaaat tttgtcttca    141840
gaacataaaa gaataggcac ataatgtgca tagttttctc atggtattac aaagaatgtt    141900
ctcgaatgaa aatactacat tattgaaaat gagcatattg gagtctctgc tagctttgac    141960
atagttctgt cacagtgtca aatatactat ttataattaa attatgggcc ccaggattat    142020
ctgctctaaa gaaaaagagt cacaaaataa tagacaaata tgggggaaa tgcaatggac      142080 tgaccgaggc gctaaggagt ggggatcaag accccagaat gagagcatag tgcttagtct    142140
```

```
gatgcagcct gtgagtgaca aatccatagc aagcacattc tttctgtgct ggtgctgaga  142200
aacaggacca ttttcaagct tatttgctag ccactttata tttttatttt gttttgattt  142260
taccatatag atctatgata ctcttgagaa cattttagat tacacactat atctgtaaaa  142320
ggatacttca aagtttcctg tcttagattc atctgacagt ttttctatgg attgtgagaa  142380
gggctcacag tttatgttca gaagggccaa caggtctcct tgataaaggg ttccttactt  142440
cctgaagtac caaaacgatt aggattcttt tatttctgga cacttcattt ttgtcatgaa  142500
ttagactatt cactggttct gggaaaaaat tcagtggttt gtatcgatat cttttacatg  142560
tgaatgacta taattttatg ttcctttgta acattgagac ttcatgtaaa acttttgact  142620 ctaactttt tttttctttta tcctgggcac atgtatgcta tttttactga attagatagc  142680
tttggtattt ataaaaattg tatccctctt attcataatt tcctgaaaat gaagggctat  142740
tgttatcttt gataatttat gcttcaagta aagaagtgtg gctctttggc atctgtattt  142800
agcaaaattt gctttgtata attttaatga tgcataatgg tggtggtgtc atgttttaat  142860
aatttaaaat gttgtttatg ttatcatatg taaatagcat ttatctctta attggtggta  142920
aaattattaa tgtatacttt atggttctag ggaggtaatg gtaaaagaaa acaaggaatc  142980
aaaacacaaa atgtcttatt ctgggagagt gaaaaccctc tgccttcaga agaacactgc  143040
tctttggata ggaactggag gaggccatat tttactcctg gatctttcaa ctcgtcgact  143100
tatacgtgta atttacaact tttgtaattc ggtcagagtc atgatgacag cacagctagg  143160
caagtttctt tccttagat attttttcata ttctctaagt cttataaaat atgcctttat  143220
tttacgttta cattttctct gaactttcca gtgtcatatg gatggtcttg gagggtcaca  143280
cagtgaaaca taagactggt ataaattgtg aatagggtca ttacagaagt ggagggagta  143340
aatgctctca gtcccacaag agaagcagat tactgcagct gaacactcag tttgggtctt  143400
acttgctttt ttccttttta cctaaggcaa aaatgggaaa tacatggtat tgaatatatt  143460 ttacttttg agcaaagaaa ataaagaaaa tgtttgtttt aatcatagtc tagcctccca  143520
gcttgttaaa gaatctcatt tggttttttca ttctataaca aatctttttt cttgcagcaa  143580
tacatgctga actgcacaac ctacaaatat tgacaaatca tattttactc aaactttgtc  143640 ttttttttgct tctattttta tatttaaata tgataaaatt gtgatagcac ataaaatata  143700
ttttctgcat aaatatattt gcgtcttcct ttgataataa tttgttttag aaaataacaa  143760
taatagcata tatacaaaag tttacaaaaa cgacactatg gggtttaatt ctgaaaaaaa  143820
ctagaattta tgtaacttta gcaaataatg aatgttttga acatggtgaa gaaaatatat  143880
tcattgcaag tatatgtgaa agaggaacat gtgttttttct agcaccttca cctatttttc  143940
atttatagac tttagagttg cacaggagtt acaattagat gctcttaatg actgtaaaact  144000 attaagatac atgtccacac aagcagagca gtaggtctct caataggttg tctcagtagt  144060
cttattctac caaagttgtt gcattctcta gttgaattgt atgtactttg ggacccaaat  144120
agcttgctta taactgaagt tatagtggaa tgtctatggg ttatagtttg attttaaaat  144180
aaagatcaat tggaggatag cctacaaggt gctgcatgag ctggcttcac tgtacctctc  144240
ctgcctccat catctaccac attcctacca gatcttgctt gtctagatga acatccagtt  144300
cttctcaatt actatgctat attttgcctc agggatttgc acatgctgtt tatttctttg  144360
cttagttaac atagctttttt ttcatgctta tttaactcat atgctttgaa atgttagctc  144420
ctgtgtcaaa acctctgaga agccaacact gattaggtca aagttccgc tttgggttcc    144480
```

```
cataacagct tcttgcata gttttgatca tggtcatatt ttttttttcat taatgctagt   144540 ctcttcacta gaatataaac tccaagacgg ttgggttagt gtgttttttgt ttacccctttt  144600 tttcccagga tctagcctag ggcctacata gaagactttt gatgcaaatt tgttgaataa   144660
attagtgaat gatttgaaaa gaaaatatga tattttgaca tagtatcagt atatccatcc   144720
atctaagtgt ccatctaaat actcatattt gtactaaata ctcatatttg taccttacca   144780
tatccaaaga acttttcaca cacattacct cgtttaacat tgtaactttg ggaagggtaa   144840
tgtataaata ctgagcctat tttatagaaa ggttaagctg ttttctcaga ctcacataat   144900
taagaattgc agcaaggagt ggatcacaga ttttgttatt tttaaaaaa atgctggtct    144960 ttattcaata taattgaagg gtcacctaga aatagaatt gtgaattcag ttccaaggta    145020
tttgtgtctt aaactatgaa caactttact tttttttcag gccagtttaa tatatagttt   145080
taacagaaaa cttacatatt ttgttttttgt aaaggaagcc ttaaaatgt catgctggta    145140 ttgggctaca accggaaaaa tactgaaggt acacaaaagc agaaaggtaa catttagaag  145200
gatactgttt tccaaacagg gcaatgatgt gaatgatggt aacatattat gtgtttcata  145260
aatttgtaga aaatattaca tatggtataa tcaggaattt taattggtag tttatagtgt   145320
aaagaactta gacataaatt ttcaaaatta caagtgatat gaagtgttaa atatttatat   145380
tttcagctga agtagaggtg tcaatcacta gctcaacctt aaacgaaatg tgaatatttt   145440
ttacaactta tctatatcta cataatgtct aattttgaac agtgtttgaa aaagctttta   145500
tttcttttag aatatgaaat gttaatttat taaatgttga tactctattt gaaatttaat   145560
agtttctata atgtattata aaactttttcc aagtatagtt ttttataaat aataatttag   145620
tacattagtt atagctgtgt ttatatttac atttatctaa gtcaactaaa aatacatgag   145680
ccaaactgaa ataaaataag aatgttttat gatggatctt tgaaacatga tttcatttttt  145740 ttctttttct agagatacaa tcttgcttga ccgtttggga catcaatctt ccacatgaag   145800
tgcaaaattt agaaaaacac attgaagtga gaaaagaatt agctgaaaaa atgagacgaa   145860
catctgttga gtaagagaga aataggaatt gtctttggat aggaaaatta ttctctcctc   145920
ttgtaaatat ttattttaaa aatgttcaca tggaaagggt actcacattt tttgaaatag   145980
ctcgtgtgta tgaaggaatg ttattatttt taatttaaat atatgtaaaa atacttacca   146040
gtaaatgtgt attttaaaga actatttaaa acacaatgtt atatttctta taaataccag   146100
ttactttcgt tcattaatta atgaaaataa atctgtgaag tacctaattt aagtactcat   146160
actaaaattt ataaggccga taatttttttg ttttcttgtc tgtaatggag gtaaacttta   146220
ttttaaattc tgtgcttaag acaggactat tgcttgtcga tttttctaga aatctgcacg   146280
gtataatgaa aatattaaga cagtttccca tgtaatgtat tccttcttag attgcatcga   146340
aatgcactat catatatgct tgtaaatatt caaatgaatt tgcactaata aagtcctttg   146400
ttggtatgtg aattctcttt gttgctgttg caaacagtgc atcttacaca acttcactca   146460
attcaaaaga aaactccatt aaaagtacta atgaaaaaac atgacatact gtcaaagtcc   146520
tcatatctag gaaagacaca gaaactctct ttgtcacaga aactctctgt gtctttccta   146580
gacataaatg agttgttttt caactctatg tttgaatgtg gatacctga attttgtata   146640 attagtgtaa atacagtgtt cagtccttca agtgatattt ttattttttt attcatacca   146700
ctagctactt gttttctaat ctgcttcatt ctaatgctta tattcatctt ttccctaaat   146760
ttgtgatgct gcagatccta catcattcag atagaaacct ttttttttt cagaattata   146820 gaattccaca gctcctacca agaccatgag gataaatatc taacactttt cagttgctga   146880
```

```
aggagaaagg agctttagtt atgatggata aaaatatctg ccaccctagg cttccaaatt   146940
atacttaaat tgtttacata gcttaccaca ataggagtat cagggccaaa tacctatgta   147000
ataatttgag gtcatttctg ctttaggaaa agtactttcg gtaaattctt tggccctgac   147060
cagtattcat tatttcagat aattccctgt gataggacaa ctagtacatt taatattctc   147120
agaacttatg gcattttact atgtgaaaac tttaaattta tttatattaa gggtaatcaa   147180
attcttaaag atgaaagatt ttctgtattt taaaggaagc tatgctttaa cttgttatgt   147240
aattaacaaa aaaatcatat ataatagagc tctttgttcc agtgttatct ctttcattgt   147300
tactttgtat ttgcaattt ttttaccaaa gacaaattaa aaaatgaat accatattta    147360 aatggaataa taaaggtttt ttaaaaactt taaatgcttt taagcatgtt tatgaatttt   147420
taaactttgt gatagtgttt tgcttttcac ataggtct gttatccatc tcataggaaa    147480
ctttgtatta atttgtatat gggacattcc acaataagaa agtgcaacta aagttttttc   147540
cttgataact tatggaatat ttaaatttaa ttttctataa tacatatagt tgccaggatc    147600
ccaggacaaa atctgatggg catgatacat tctattttca agttctctta aaaagttttt   147660
gtaagtaaac ttgtttgctc ttgagtactg aaacaaaata taagacttta gagcaaatga   147720
catatacaaa aaaaggcac agtcacttca actgttttct gattagaagc ctaaaataac    147780
ttgctaatta tgatcaaaat acaagcatat tatcgtaaca aaatattctt ttgggaaaat   147840
tttgaattaa gaaaagggag cctctttgac tctaattctg gtaggtactc tatcgattat   147900
gtgtgaacta tttcaactaa aacgcaactt attttcatc aaggcagtga aatatattga    147960
tgaaacatag cagaattacc aaaaaaagat tgtcaatttt cctaagttaa atgtaaggat   148020
gcaaatgttc taatattgag gggagataaa attcaaaacc attgggactt tgcttctta    148080 tccatcactt tgggtagctg aacacctaac ctggtaaatt gaatgttttt catggaggct   148140
tatcagcaat tcagtaaaat agtaaactat gtcaactcgg gagaaactga catcctcatt   148200
ctccatgcta gccagtttct catccagggt gtcattgttt ctaataacaa ttcagaatct   148260
ggctgcttaa aggcacctac gtacgtggtt cttttctaatt tgtcaaggca tttggagtga   148320
tcctatcacc ctgatttcaa gcaaaagaca gggaggcacc tgacccaaag gcctgctgtc   148380
tgaacacact ctgaatgggt gagcagagat gtgctttaag atagaaccta aggtggttct   148440
ctctatgtgc tgccctcaca ctgctcttga tttctaccct tacctgggaa gtctctactt   148500
gatgtctgtc ttaggctaag aaaaagagaa gagaaaggga atgagtatta gcatctggat   148560
tctggggctg cttcttggcc tctgtgagaa tccactgttt cacagcaatc acagcctaga   148620
aaactagact ttatggagta aacaataggt atcattctga cctgggcttc accacaatca   148680
cccactgaac actcccaaga gaaggttgtt accatttatt tatgaaaata ccaaactatg   148740
tgatacatac tctattagaa gtattatgga aaaatagaga atatgtctac ctggccagag   148800
aatagaggat ctggatcaca aaaaaagtac aaatatttaa gcagagactt aggacaaatg   148860
ggcattcaac aatttaggac acatgggcat tctacaattt ccagagtgaa gtaaacattc   148920
taggcagata aatcacacat gtgctgtctt aggaatgtga gcttatttg aaagcatccc    148980 tatcaaatac gtgctaaaac ttgtgacaag ttcccattcc tagagtactt acaggataca   149040
cttaagtgac tgaagatgca agagaaatat atatttgtgt atggatatag cattttatca   149100
ttaattgaga gattataaag ctaatgagct tttctttgca gagggagtat ttgttaggat   149160
gaaatgggga gagatgtttc aaacaccaag tttatcttat aggttaagaa atcctagaag   149220
```

```
gaatccatga ctttatgtat atatacaata tatgacaaga gatttcccca tctcattaca   149280
aaatgagcac aaagtaacta actcaaagct tttgctatta tgataaaagt ttaaaaggct   149340
agtacatagc agaaatgtga tttactataa cgggggtcca ggggataaaa tatttgcaag   149400
ctgattgtct catgttggca atgttttcat ttcctactac gttaggtaac acagatgaga   149460
ttgtacatca gagtaagaag gcaaccacta atagaagctg catgcgggca aaagactatt   149520
ctctgaccat aagcttagtt tagatggatc cttgctgcaa tcactaaatt cataaatctg   149580
tgctagtatt ggatcaggaa atctctgcac aagcagataa ataaaaactt tctgctttgg   149640
ctgaaataac tgcttttagg aaaagaaaga gtatatgctt attaatatag cttgggatgt   149700
ggacctcttt gacgagacta tacaattcaa ggtagacaaa gtatgcctaa aaataaatct   149760
aaaataaact tgtatattca aatggaacat attctttaat aatgtcattt ttaagggctc   149820
tgcatttatt ccataaatgc tgccattatt gttcagtttt tcttaattac ctgcattcac   149880
tttagaaaac agaaaaaaaa aaaaaaaaa aaaaacaga aacagttgca aagaaagca    149940 gccagaaaga acatacattt agaattgaaa aagaccttgg tctaaattct agatttggca   150000
t                                                                   150001

<210> SEQ ID NO 3
<211> LENGTH: 9239
<212> TYPE: DNA
<213> ORGANISM: Homo sapines

<400> SEQUENCE: 3
gcgctggctg cgggcggtga gctgagctcg cccccgggga gctgtggccg gcgcccctgc     60
cggttccctg agcagcggac gttcatgctg ggagggcggc gggttggaag caggtgccac    120
catggctagt ggcagctgtc agggtgcgga agaggacgga gaaactctga agaagttgat    180
agtcaggctg aacaatgtcc aggaaggaaa acagatagaa acgctggtcc aaatcctgga    240
ggatctgctg tgttcacgt actccgagca cgcctccaag ttatttcaag gcaaaaatat    300
ccatgtgcct ctgttgatcg tcttggactc ctatatgaga gtcgcgagtg tgcagcaggt    360
gggttggtca cttctgtgca aattaataga agtctgtcca ggtacaatgc aaagcttaat    420
gggaccccag gatgttggaa atgattggga agtccttggt gttcaccaat tgattcttaa    480
aatgctaaca gttcataatg ccagtgtaaa cttgtcagtg attggactga agaccttaga    540
tctcctccta acttcaggta aaatcacctt gctgatattg gatgaagaaa gtgatatttt    600
catgttaatt tttgatgcca tgcactcatt tccagccaat gatgaagtcc agaaacttgg    660
atgcaaagct ttacatgtgc tgtttgagag agtctcagag gagcaactga ctgaatttgt    720
tgagaacaaa gattatatga tattgttaag tgcgttaaca aattttaaag atgaagagga    780
aattgtgctt catgtgctgc attgtttaca ttccctagcg attccttgca ataatgtgga    840
agtcctcatg agtggcaatg tcaggtgtta atattgtg gtggaagcta tgaaagcatt     900
ccctatgagt gaaagaattc aagaagtgag ttgctgtttg ctccataggc ttacattagg    960 taatttttc aatatcctgg tattaaacga agtccatgag tttgtggtga aagctgtgca   1020
gcagtaccca gagaatgcag cattgcagat ctcagcgctc agctgtttgg ccctcctcac   1080
tgagactatt ttcttaaatc aagatttaga ggaaagaat gagaatcaag agaatgatga   1140 tgaggggaa gaagataaat tgttttggct ggaagcctgt acaaagcat taacgtggca   1200 tagaaagaac aagcacgtgc aggaggccgc atgctgggca ctaaataatc tccttatgta   1260
ccaaaacagt ttacatgaga agattggaga tgaagatggc catttcccag ctcataggga   1320
```

-continued

```
agtgatgctc tccatgctga tgcattcttc atcaaaggaa gttttccagg catctgcgaa    1380
tgcattgtca actctcttag aacaaaatgt taatttcaga aaaatactgt tatcaaaagg    1440
aatacacctg aatgttttgg agttaatgca gaagcatata cattctcctg aagtggctga    1500
aagtggctgt aaaatgctaa atcatctttt tgaaggaagc aacacttccc tggatataat    1560
ggcagcagtg gtccccaaaa tactaacagt tatgaaacgt catgagacat cattaccagt    1620
gcagctggag gcgcttcgag ctattttaca ttttatagtg cctggcatgc cagaagaatc    1680
cagggaggat acagaatttc atcataagct aaatatggtt aaaaaacagt gtttcaagaa    1740
tgatattcac aaactggtcc tagcagcttt gaacaggttc attggaaatc ctgggattca    1800
gaaatgtgga ttaaaagtaa tttcttctat tgtacatttt cctgatgcat tagagatgtt    1860
atccctggaa ggtgctatgg attcagtgct tcacacactg cagatgtatc cagatgacca    1920
agaaattcag tgtctgggtt aagtcttat aggatacttg attacaaaga gaatgtgtt    1980 cataggaact ggacatctgc tggcaaaaat tctggtttcc agcttatacc gatttaagga    2040
tgttgctgaa atacagacta aaggatttca gacaatctta gcaatcctca aattgtcagc    2100
atctttttct aagctgctgg tgcatcattc atttgactta gtaatattcc atcaaatgtc    2160
ttccaatatc atggaacaaa aggatcaaca gtttctaaac ctctgttgca agtgttttgc    2220
aaaagtagct atggatgatt acttaaaaaa tgtgatgcta gagagagcgt gtgatcagaa    2280
taacagcatc atggttgaat gcttgcttct attgggagca gatgccaatc aagcaaagga    2340
gggatcttct ttaatttgtc aggtatgtga gaaagagagc agtcccaaat tggtggaact    2400
cttactgaat agtggatctc gtgaacaaga tgtacgaaaa gcgttgacga taagcattgg    2460
gaaaggtgac agccagatca tcagcttgct cttaaggagg ctggccctgg atgtggccaa    2520
caatagcatt tgccttggag gattttgtat aggaaaagtt gaaccttctt ggcttggtcc    2580
tttatttcca gataagactt ctaatttaag gaaacaaaca aatatagcat ctacactagc    2640
aagaatggtg atcagatatc agatgaaaag tgctgtggaa gaaggaacag cctcaggcag    2700
cgatggaaat ttttctgaag atgtgctgtc taaatttgat gaatggacct ttattcctga    2760
ctcttctatg gacagtgtgt tgctcaaag tgatgacctg gatagtgaag gaagtgaagg    2820
ctcatttctt gtgaaaaaga aatctaattc aattagtgta ggagaatttt accgagatgc    2880
cgtattacag cgttgctcac caaatttgca aagacattcc aattccttgg ggcccatttt    2940
tgatcatgaa gatttactga agcgaaaaag aaaaatatta tcttcagatg attcactcag    3000
gtcatcaaaa cttcaatccc atatgaggca ttcagacagc atttcttctc tggcttctga    3060
gagagaatat attacatcac tagacctttc agcaaatgaa ctaagagata ttgatgccct    3120
aagccagaaa tgctgtataa gtgttcattt ggagcatctt gaaaagctgg agcttccacca    3180 gaatgcactc acgagctttc cacaacagct atgtgaaact ctgaagagtt tgacacattt    3240
ggacttgcac agtaataaat ttacatcatt tccttcttat ttgttgaaaa tgagttgtat    3300
tgctaatctt gatgtctctc gaaatgacat tggaccctca gtggttttag atcctacagt    3360
gaaatgtcca actctgaaac agtttaacct gtcatataac cagctgtctt ttgtacctga    3420
gaacctcact gatgtggtag agaaactgga gcagctcatt ttagaaggaa ataaaatatc    3480
agggatatgc tccccccttga gactgaagga actgaagatt ttaaacctta gtaagaacca    3540
catttcatcc ctatcagaga actttcttga ggcttgtcct aaagtggaga gtttcagtgc    3600
cagaatgaat tttcttgctg ctatgccttt cttgcctcct tctatgacaa tcctaaaatt    3660
```

-continued

```
atctcagaac aaattttcct gtattccaga agcaatttta aatcttccac acttgcggtc    3720
tttagatatg agcagcaatg atattcagta cctaccaggt cccgcacact ggaaatcttt    3780
gaacttaagg gaactcttat ttagccataa tcagatcagc atcttggact tgagtgaaaa    3840
agcatattta tggtctagag tagagaaact gcatctttct cacaataaac tgaaagagat    3900
tcctcctgag attggctgtc ttgaaaatct gacatctctg gatgtcagtt acaacttgga    3960
actaagatcc tttcccaatg aaatggggaa attaagcaaa atatgggatc ttcctttgga    4020
tgaactgcat cttaactttg attttaaaca tataggatgt aaagccaaag acatcataag    4080
gtttcttcaa cagcgattaa aaaaggctgt gccttataac cgaatgaaac ttatgattgt    4140
gggaaatact gggagtggta aaaccacctt attgcagcaa ttaatgaaaa ccaagaaatc    4200
agatcttgga atgcaaagtg ccacagttgg catagatgtg aaagactggc ctatccaaat    4260
aagagacaaa agaaagagag atctcgtcct aaatgtgtgg gattttgcag gtcgtgagga    4320
attctatagt actcatcccc attttatgac gcagcgagca ttgtaccttg ctgtctatga    4380
cctcagcaag ggacaggctg aagttgatgc catgaagcct ggctcttca atataaaggc     4440 tcgcgcttct tcttcccctg tgattctcgt tggcacacat ttggatgttt ctgatgagaa    4500
gcaacgcaaa gcctgcatga gtaaaatcac caaggaactc ctgaataagc gagggttccc    4560
tgccatacga gattaccact ttgtgaatgc caccgaggaa tctgatgctt tggcaaaact    4620
tcggaaaacc atcataaacg agagccttaa tttcaagatc cgagatcagc ttgttgttgg    4680
acagctgatt ccagactgct atgtagaact tgaaaaaatc attttatcgg agcgtaaaaa    4740
tgtgccaatt gaatttcccg taattgaccg gaaacgatta ttacaactag tgagagaaaa    4800
tcagctgcag ttagatgaaa atgagcttcc tcacgcagtt cactttctaa atgaatcagg    4860
agtccttctt cattttcaag acccagcact gcagttaagt gacttgtact ttgtggaacc    4920
caagtggctt tgtaaaatca tggcacagat tttgacagtg aaagtggaag ttgtccaaa    4980 acaccctaag ggcattattt cgcgtagaga tgtggaaaaa tttctttcaa aaaaaggaa    5040 atttccaaag aactacatgt cacagtattt taagctccta gaaaaattcc agattgcttt    5100
gccaatagga gaagaatatt tgctggttcc aagcagtttg tctgaccaca ggcctgtgat    5160
agagcttccc cattgtgaga actctgaaat tatcatccga ctatatgaaa tgccttattt    5220
tccaatggga ttttggtcaa gattaatcaa tcgattactt gagatttcac cttacatgct    5280
ttcagggaga gaacgagcac ttcgcccaaa cagaatgtat tggcgacaag gcatttactt    5340
aaattggtct cctgaagctt attgtctggt aggatctgaa gtcttagaca atcatccaga    5400
gagtttctta aaaattacag ttccttcttg tagaaaaggc tgtattcttt tgggccaagt    5460
tgtggaccac attgattctc tcatggaaga atggtttcct gggttgctgg agattgatat    5520
ttgtggtgaa ggagaaactc tgttgaagaa atgggcatta tatagtttta atgatggtga    5580
agaacatcaa aaaatcttac ttgatgactt gatgaagaaa gcagaggaag agatctcttt    5640
agtaaatcca gatcaaccaa ggctcaccat tccaatatct cagattgccc ctgacttgat    5700
tttggctgac ctgcctagaa atattatgtt gaataatgat gagttggaat tgaacaagc    5760 tccagagttt ctcctaggtg atggcagttt tggatcagtt taccgagcag cctatgaagg    5820
agaagaagtg gctgtgaaga tttttaataa acatacatca ctcaggctgt taagacaaga    5880
gcttgtggtg ctttgccacc tccaccaccc cagtttgata tctttgctgg cagctgggat    5940 tcgtcccgg atgttggtga tggagttagc ctccaagggt tccttggatc gcctgcttca    6000
gcaggacaaa gccagcctca ctagaaccct acagcacagg attgcactcc acgtagctga    6060
```

```
tggtttgaga tacctccact cagccatgat tatataccga gacctgaaac cccacaatgt   6120
gctgcttttc acactgtatc ccaatgctgc catcattgca aagattgctg actacggcat   6180
tgctcagtac tgctgtagaa tggggataaa aacatcagag ggcacaccag ggtttcgtgc   6240
acctgaagtt gccagaggaa atgtcattta taaccaacag gctgatgttt attcatttgg   6300
tttactactc tatgacattt tgacaactgg aggtagaata gtagagggtt gaagtttcc    6360 aaatgagttt gatgaattag aaatacaagg aaaattacct gatccagtta aagaatatgg   6420
ttgtgcccca tggcctatgg ttgagaaatt aattaaacag tgtttgaaag aaaatcctca   6480
agaaaggcct acttctgccc aggtctttga cattttgaat tcagctgaat tagtctgtct   6540
gacgagacgc attttattac ctaaaaacgt aattgttgaa tgcatggttg ctacacatca   6600
caacagcagg aatgcaagca tttggctggg ctgtgggcac accgacagag gacagctctc   6660
atttcttgac ttaaatactg aaggatacac ttctgaggaa gttgctgata gtagaatatt   6720
gtgcttagcc ttggtgcatc ttcctgttga aaaggaaagc tggattgtgt ctgggacaca   6780
gtctggtact ctcctggtca tcaataccga agatgggaaa aagagacata ccctagaaaa   6840
gatgactgat tctgtcactt gtttgtattg caattccttt tccaagcaaa gcaaacaaaa   6900
aaatttcttt ttggttggaa ccgctgatgg caagttagca attttgaag ataagactgt    6960 taagcttaaa ggagctgctc ctttgaagat actaaatata ggaaatgtca gtactccatt   7020
gatgtgtttg agtgaatcca caaattcaac ggaaagaaat gtaatgtggg gaggatgtgg   7080
cacaaagatt ttctcctttt ctaatgattt caccattcag aaactcattg agacaagaac   7140
aagccaactg ttttcttatg cagctttcag tgattccaac atcataacag tggtggtaga   7200
cactgctctc tatattgcta agcaaaatag ccctgttgtg gaagtgtggg ataagaaaac   7260
tgaaaaactc tgtggactaa tagactgcgt gcacttttta agggaggtaa tggtaaaaga   7320
aaacaaggaa tcaaaacaca aaatgtctta ttctgggaga gtgaaaaccc tctgccttca   7380
gaagaacact gctctttgga taggaactgg aggaggccat attttactcc tggatctttc   7440
aactcgtcga cttatacgtg taattacaa cttttgtaat tcggtcagag tcatgatgac    7500
agcacagcta ggaagcctta aaaatgtcat gctggtattg ggctacaacc ggaaaatac    7560 tgaaggtaca caaaagcaga aagagataca atcttgcttg accgtttggg acatcaatct   7620
tccacatgaa gtgcaaaatt tagaaaaaca cattgaagtg agaaaagaat tagctgaaaa   7680
aatgagacga acatctgttg agtaagagag aaataggaat tgtctttgga taggaaaatt   7740
attctctcct cttgtaaata tttattttaa aaatgttcac atggaaaggg tactcacatt   7800
ttttgaaata gctcgtgtgt atgaaggaat gttattattt ttaatttaaa tatatgtaaa   7860
aatacttacc agtaaatgtg tatttttaaag aactatttaa aacacaatgt tatatttctt   7920
ataaatacca gttactttcg ttcattaatt aatgaaaata atctgtgaa gtacctaatt     7980 taagtactca tactaaaatt tataaggccg ataatttttt gttttcttgt ctgtaatgga   8040
ggtaaacttt atttttaaatt ctgtgcttaa gacaggacta ttgcttgtcg atttttctag   8100
aaatctgcac ggtataatga aaatattaag acagtttccc atgtaatgta ttccttctta   8160
gattgcatcg aaatgcacta tcatatatgc ttgtaaatat tcaaatgaat ttgcactaat   8220
aaagtccttt gttggtatgt gaattctctt tgttgctgtt gcaaacagtg catcttacac   8280
aacttcactc aattcaaaag aaaactccat taaaagtact aatgaaaaaa catgacatac   8340
tgtcaaagtc ctcatatcta ggaaagacac agaaactctc tttgtcacag aaactctctg   8400
```

```
tgtcttttcct agacataata gagttgtttt tcaactctat gtttgaatgt ggataccctg    8460
aattttgtat aattagtgta aatacagtgt tcagtccttc aagtgatatt tttatttttt    8520
tattcatacc actagctact tgttttctaa tctgcttcat tctaatgctt atattcatct    8580
tttccctaaa tttgtgatgc tgcagatcct acatcattca gatagaaacc tttttttttt    8640
tcagaattat agaattccac agctcctacc aagaccatga ggataaatat ctaacacttt    8700
tcagttgctg aaggagaaag gagctttagt tatgatggat aaaaatatct gccaccctag    8760
gcttccaaat tatacttaaa ttgtttacat agcttaccac aataggagta tcagggccaa    8820
atacctatgt aataatttga ggtcatttct gctttaggaa aagtactttc ggtaaattct    8880
ttggccctga ccagtattca ttatttcaga taattccctg tgataggaca actagtacat    8940
ttaatattct cagaacttat ggcattttac tatgtgaaaa ctttaaattt atttatatta    9000
agggtaatca aattcttaaa gatgaaagat tttctgtatt ttaaaggaag ctatgcttta    9060
acttgttatg taattaacaa aaaaatcata tataatagag ctctttgttc cagtgttatc    9120
tctttcattg ttactttgta tttgcaattt tttttaccaa agacaaatta aaaaaatgaa    9180
taccatattt aaatggaata ataaaggttt tttaaaaact taaaaaaaa aaaaaaaa     9239
```

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

```
<211> LENGTH: 19
<212> TYPE: DNA
<213> ORGANISM: Artificial sequence
<220> FEATURE:
<223> OTHER INFORMATION: Primer

<400> SEQUENCE: 11
ggcgagttat ccgcaccat                                            19

<210> SEQ ID NO 12
<211> LENGTH: 24
<212> TYPE: DNA
<213> ORGANISM: Artificial sequence
<220> FEATURE:
<223> OTHER INFORMATION: Primer

<400> SEQUENCE: 12
ccaaaaccag catgacattc ttaa                                      24

<210> SEQ ID NO 13
<211> LENGTH: 23
<212> TYPE: DNA
<213> ORGANISM: Artificial sequence
<220> FEATURE:
<223> OTHER INFORMATION: Probe

<400> SEQUENCE: 13
tgagagccat ggccacagca caa                                       23

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
agtccaacta ttgacaggtt                                           20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
agtgcactag cagcttggag                                           20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tccaggtggc tactgaggca                                           20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
```

```
cagccaagat caagtccgga                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ccacacctct acgacagggc                                               20
```

METHODS FOR REDUCING LRRK2 EXPRESSION

SEQUENCE LISTING

The present application is being filed along with a Sequence Listing in electronic format. The Sequence Listing is provided as a file entitled BIOL0282USC1SEQ_ST25.txt, created on Dec. 11, 2020, which is 216 KB in size. The information in the electronic format of the sequence listing is incorporated herein by reference in its entirety.

FIELD

Provided are methods for reducing expression of LRRK2 mRNA, and optionally reducing expression of LRRK2 protein, in an animal. Such methods are useful to prevent or ameliorate at least one symptom of a neurodegenerative disease. Such symptoms include loss of motor function, aggregate formation, and neuron death. Such neurodegenerative diseases include Parkinson's Disease, including non-LRRK2 mediated Parkinson's Disease.

BACKGROUND

The leucine-rich repeat kinase 2 (LRRK2) gene encodes a protein called Dardarian. The LRRK2 gene is active in the brain and other tissues throughout the body. One segment of the dardarin protein is enriched with leucine and may be involved in signal transduction and cytoskeleton assembly. Other parts of the dardarin protein are also thought to be involved in protein-protein interactions. Additional studies indicate that dardarin has an enzyme function known as kinase activity, including phosphorylation and GTPase activity.

Genomewide association studies have found an association between LRRK2 and Parkinson's Disease. Indeed, LRRK2 is the greatest known genetic contributor to Parkinson's disease. Nonetheless, Parkinson's disease has not been considered to be a genetic disease. The majority of Parkinson's disease cases are idiopathic. Approximately 10 percent of Parkinson's disease cases have been linked to a genetic cause. Mutations in the LRRK2 gene are the most common cause of Parkinson's disease in this relatively small group, representing one to two percent of total Parkinson's cases.

Currently there is a lack of acceptable options for treating neurodegenerative diseases such as Parkinson's Disease, including non-LRRK2 mediated Parkinson's Disease. It is therefore an object herein to provide methods for the treatment of such diseases.

SUMMARY OF THE INVENTION

Provided herein are methods for reducing expression of LRRK2 mRNA, and optionally reducing the amount of LRRK2 protein, in an animal. In certain embodiments, the animal has Parkinson's Disease. In certain embodiments, the animal has non-LRRK2 mediated Parkinson's Disease. In certain embodiments, compounds useful for reducing expression of LRRK2 mRNA are oligomeric compounds. In certain embodiments, the oligomeric compound comprises a modified oligonucleotide.

In certain embodiments, LRRK2 mRNA expression is reduced in a cell or tissues. In certain embodiments, the cell or tissue is in an animal. In certain embodiments, the animal has Parkinson's Disease. In certain embodiments, the animal has non-LRRK2 mediated Parkinson's Disease.

Also provided are methods useful for ameliorating at least one symptom of Parkinson's Disease. In certain embodiments, symptoms are loss of motor function, aggregate formation, and neuron death.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

"Administering" means providing a pharmaceutical agent to an animal. "Administered prior to the detection of the at least one symptom" is prophylactic administration and means providing the pharmaceutical agent to an animal before a symptom of Parkinson's disease is apparent through observation or clinical diagnosis.

"Animal" means a human or non-human animal.

"Antisense activity" means any detectable and/or measurable change attributable to the hybridization of an oligomeric compound to its target nucleic acid. In certain embodiments, antisense activity is a decrease in the amount or expression of a target nucleic acid or protein encoded by such target nucleic acid compared to target nucleic acid levels or target protein levels in the absence of the oligomeric compound. In certain embodiments, antisense activity is a change in splicing of a pre-mRNA nucleic acid target. In certain embodiments, antisense activity is an increase in the amount or expression of a target nucleic acid or protein encoded by such target nucleic acid compared to target nucleic acid levels or target protein levels in the absence of the oligomeric compound.

"Ameliorate" or "amelioration" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom is loss of motor function, aggregate formation, or neuron death. In certain embodiments, amelioration of these symptoms results in improved motor function, reduced aggregate formation, and or preservation of neurons.

"Bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include, but unless otherwise specific are not limited to, adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

"Conjugate group" means a group of atoms that is directly or indirectly attached to an oligonucleotide. Conjugate groups include a conjugate moiety and a conjugate linker that attaches the conjugate moiety to the oligonucleotide.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Duplex" means two oligomeric compounds that are paired. In certain embodiments, the two oligomeric compounds are paired via hybridization of complementary nucleobases.

"Gapmer" means an oligomeric compound comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage ("phosphodiester internucleoside linkage"). Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage.

"MOE" means methoxyethyl. "2'-MOE" means a —OCH$_2$CH$_2$OCH$_3$ group at the 2' position of a furanosyl ring.

"Non-bicyclic sugar moiety" means a modified sugar moiety that comprises a modification, such as a substituent, that does not form a bridge between two atoms of the sugar to form a second ring.

"Non-LRRK2 mediated Parkinson's Disease" is a diagnosis of Parkinson's disease not associated with a causative LRRK2 genetic mutation. Causitive LRRK2 genetic mutations include G2019S, R1441C, R1441G, I2020T, and Y1699C. Diagnosis of Parkinson's disease may be accomplished by any method including evaluating an individual's medical history, observation of signs and symptoms, and standard clinical tests or assessments. Genetic testing for a mutation associated with LRRK2, such as G2019S, R1441C, R1441G, I2020T, and Y1699C, may reveal whether an individual has non-LRRK2 mediated Parkinson's disease. An individual having a diagnosis of Parkinson's disease, but without a causative LRRK2 mutation, has non-LRRK2 mediated Parkinson's disease. "Identifying an animal having non-LRRK2 mediated Parkinson's Disease" means identifying an animal having been diagnosed with Parkinson's Disease or predisposed to develop Parkinson's Disease without a causative LRRK2 mutation.

"Nucleobase" means an unmodified nucleobase or a modified nucleobase. As used herein "an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methylcytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

"Nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e. no additional nucleosides are present between those that are linked).

"Oligomeric compound" means a compound comprising an oligonucleotide and optionally one or more additional features, such as a conjugate group or terminal group.

"Oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

"Parkinson's Disease" is a progressive neurodegenerative disease that affects nerve cells in the brain, primarily the substantia nigra. "At least one symptom of Parkinson's disease" includes loss of motor function, aggregate formation, or neuron death.

"Reducing or inhibiting the expression or amount" refers to a reduction or blockade of the expression or amount relative to the expression or amount in an untreated or control sample and does not necessarily indicate a total elimination of expression or amount.

"Single-stranded" in reference to an oligomeric compound means such a compound that is not paired with a second oligomeric compound to form a duplex.

"Standard cell assay" means the assay described in Example 1 and reasonable variations thereof "Standard in vivo experiment" means the procedure described in Example 2 and reasonable variations thereof.

"Sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. Modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Therapeutically effective amount" means an amount of a pharmaceutical agent that provides a therapeutic benefit to an animal. For example, a therapeutically effective amount improves a symptom of a disease.

The present disclosure provides the following non-limiting numbered embodiments:

Embodiment 1. A method comprising administering to an animal having Parkinson's disease or non-LRRK2 mediated Parkinson's disease an oligomeric compound comprising a modified oligonucleotide, wherein the modified oligonucleotide consists of 12 to 30 linked nucleosides, and wherein the modified oligonucleotide has a nucleobase sequence that is complementary to a LRRK2 nucleic acid.

Embodiment 2. A method comprising identifying an animal having Parkinson's Disease or non-LRRK2 mediated Parkinson's disease and administering to the animal having Parkinson's Disease or non-LRRK2 mediated Parkinson's disease an oligomeric compound comprising a modified oligonucleotide, wherein the modified oligonucleotide has a nucleobase sequence that is complementary to the nucleobase sequence of a LRRK2 nucleic acid.

Embodiment 3. The method of embodiment 1 or 2, wherein the modified oligonucleotide has a nucleobase sequence that is at least 90% complementary to LRRK2.

Embodiment 4. The method of embodiment 1 or 2, wherein the modified oligonucleotide has a nucleobase sequence that is at least 95% complementary to LRRK2.

Embodiment 5. The method of embodiment 1 or 2, wherein the modified oligonucleotide has a nucleobase sequence that is 100% complementary to LRRK2.

Embodiment 6. The method of embodiments 1-5 wherein the administering results in amelioration of at least one symptom of Parkinson's Disease.

Embodiment 7. The method of any of embodiments 1-6 wherein the oligomeric compound is administered prior to the detection of the at least one symptom.

Embodiment 8. The method of embodiment 6 or 7, wherein the at least one symptom of Parkinson's disease is loss of motor function, aggregate formation, or neuron death.

Embodiment 9. The method of any of embodiments 6-8, wherein the amelioration is the slowing of progression of at least one symptom.

Embodiment 10. The method of any of embodiments 6-9, wherein the amelioration is the delay of onset of at least one symptom.

Embodiment 11. The method of any of embodiments 6-10, wherein the amelioration si the reduction of severity of at least one symptom.

Embodiment 12. The method of any of embodiments 6-11, wherein the amelioration is the reduction of frequency of at least one symptom.

Embodiment 13. The method of any of embodiments 1-12, wherein expression of LRRK2 mRNA is reduced in the animal.

Embodiment 14. The method of any of embodiments 1-13, wherein expression of LRRK2 protein is reduced in the animal.

Embodiment 15. The method of any of embodiments 1-14, wherein the animal is a human.

Embodiment 16. The method of any of embodiments 1-15, wherein the nucleobase sequence of LRRK2 nucleic acid is the complement of SEQ ID NO: 2 or SEQ ID NO: 3.

Embodiment 17. The method of any of embodiments 1-16, wherein the oligomeric compound is single-stranded.

Embodiment 18. The method of any of embodiment 1-17, wherein the modified oligonucleotide comprises at least one modified nucleoside.

Embodiment 19. The method of embodiment 18, wherein the modified oligonucleotide comprises at least one modified nucleoside comprising a modified sugar moiety.

Embodiment 20. The method of embodiment 19, wherein the modified oligonucleotide comprises at least one modified nucleoside comprising a bicyclic sugar moiety.

Embodiment 21. The method of embodiment 20, wherein the modified oligonucleotide comprises at least one modified nucleoside comprising a bicyclic sugar moiety having a 2'-4' bridge, wherein the 2-4' bridge is selected from —O—CH$_2$—; —O—CH$_2$—CH$_2$; and —O—CH(CH$_3$)—.

Embodiment 22. The method of any of embodiments 18-21, wherein the modified oligonucleotide comprises at least one modified nucleoside comprising a modified non-bicyclic sugar moiety.

Embodiment 23. The method of embodiment 22, wherein the modified oligonucleotide comprises at least one modified nucleoside comprising a non-bicyclic sugar moiety comprising a 2'-MOE or 2'-OMe.

Embodiment 24. The method of any of embodiments 18-23, wherein the modified oligonucleotide comprises at least one modified nucleoside comprising a sugar surrogate.

Embodiment 25. The method of embodiment 24, wherein the modified oligonucleotide comprises at least one modified nucleoside comprising a sugar surrogate selected from a morpholino, a PNA, a F-HNA, a THP, or a modified THP.

Embodiment 26. The method of any of embodiments 1-25, wherein the modified oligonucleotide has a sugar motif comprising:
a 5'-region consisting of 1-5 linked 5'-nucleosides;
a central region consisting of 6-10 linked central region nucleosides; and
a 3'-region consisting of 1-5 linked 3'-region nucleosides; wherein each of the 5'-region nucleosides and each of the 3'-region nucleosides comprises a modified sugar moiety and each of the central region nucleosides comprises an unmodified DNA sugar moiety.

Embodiment 27. The method of any of embodiments 1-26, wherein the modified oligonucleotide comprises at least one modified internucleoside linkage.

Embodiment 28. The method of embodiment 27, wherein each internucleoside linkage of the modified oligonucleotide is a modified internucleoside linkage.

Embodiment 29. The method of embodiment 27 or 28, wherein at least one internucleoside linkage is a phosphorothioate internucleoside linkage.

Embodiment 30. The method of embodiment 27 or 29, wherein the modified oligonucleotide comprises at least one unmodified phosphodiester internucleoside linkage.

Embodiment 31. The method of embodiment 27, wherein each internucleoside linkage is either an unmodified phosphodiester internucleoside linkage or a phosphorothioate internucleoside linkage.

Embodiment 32. The method of embodiment 28, wherein each internucleoside linkage is a phosphorothioate internucleoside linkage.

Embodiment 33. The method of any of embodiments 1-32, wherein the modified oligonucleotide comprises at least one modified nucleobase.

Embodiment 34. The method of embodiment 33, wherein the modified nucleobase is a 5-methylcytosine.

Embodiment 35. The method of any of embodiments 1-34, wherein each nucleobase of each nucleoside of the modified oligonucleotide is either an unmodified nucleobase or is a 5-methylcytosine.

Embodiment 36. The method of any of embodiments 1-35 wherein the oligomeric compound comprises a conjugate group.

Embodiment 37. The method of any of embodiments 1-16 or 18-36, wherein the oligomeric compound is paired with a second oligomeric compound to form a duplex.

Embodiment 38. The method of any preceding embodiments, wherein the animal has Parkinson's disease.

Embodiment 39. The method of any of embodiments 1-37, wherein the animal has non-LRRK2 mediated Parkinson's disease.

Embodiment 40. The method of any of embodiments 1-37, wherein the animal has LRRK2 mediated Parkinson's disease.

Embodiment 41. The method of any of embodiments 1-40, wherein the administering is to the central nervous system.

Embodiment 42. The method of any of embodiments 1-41, wherein the administering is intrathecal administration or intracerebroventricular administration.

Embodiment 43. The method of any of embodiments 1-42, wherein the administering does not cause toxicity in the periphery.

I. Certain Oligonucleotides

In certain embodiments, provided herein are oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)—2' and analogs thereof (see, e.g., Prakash et al., U.S. Pat. No. 8,278,425), 4'-CH$_2$—O—N(CH$_3$)—2' (see, e.g., Allerson et al., U.S. Pat. No. 7,696,345 and Allerson et al., U.S. Pat. No. 8,124,745), 4'-CH$_2$—C(H)(CH$_3$)—2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and
each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Kumar et al., Bioorg. Med. 10 Chem. Lett., 1998, 8, 2219-2222; Singh et al., J. Org. Chem., 1998, 63, 10035-10039; Srivastava et al., J. Am. Chem. Soc., 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. Pat. No. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

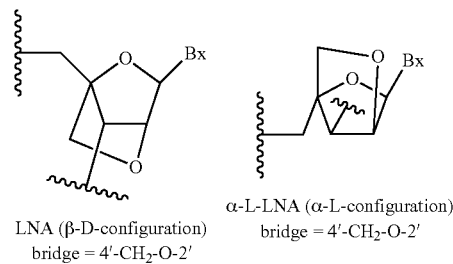

LNA (β-D-configuration)
bridge = 4'-CH$_2$-O-2'

α-L-LNA (α-L-configuration)
bridge = 4'-CH$_2$-O-2'

α-L-methyleneoxy (4'-CH$_2$—O-2') or α-L-LNA bicyclic nucleosides have been incorporated into antisense oligonucleotides that showed antisense activity (Frieden et al., Nucleic Acids Research, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

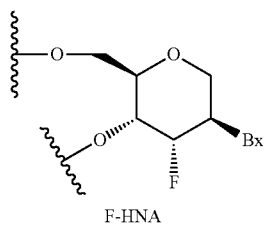

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

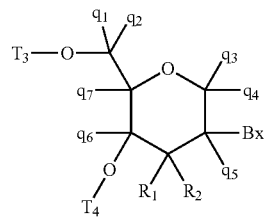

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

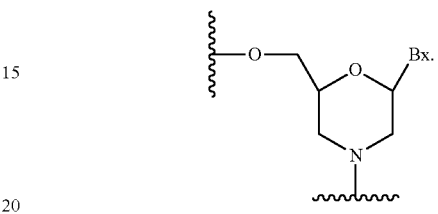

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp).

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino ($-CH_2-N(CH_3)-O-CH_2-$), thiodiester, thionocarbamate ($-O-C(=O)(NH)-S-$); siloxane ($-O-SiH_2-O-$); and N,N'-dimethylhydrazine ($-CH_2-N(CH_3)-N(CH_3)-$). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-$CH_2-N(CH_3)-O-5'$), amide-3 (3'-$CH_2-C(=O)-N(H)-5'$), amide-4 (3'-$CH_2-N(H)-C(=O)-5'$), formacetal (3'-$O-CH_2-O-5'$), methoxypropyl, and thioformacetal (3'-$S-CH_2-O-5'$). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleoside comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N. Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups.

One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Duplexed Oligomeric Compounds

In certain embodiments, oligomeric compounds described herein comprise an oligonucleotide, having a nucleobase sequence complementary to that of a target nucleic acid. Oligomeric compounds are single-strands and in certain embodiments, oligomeric compounds are single-stranded. In certain embodiments, a single-stranded oligomeric compound comprises or consists of a modified oligonucleotide and optionally a conjugate group. In certain embodiments, an oligomeric compound is paired with a second oligomeric compound to form a duplex. Such duplexed oligomeric compounds comprise a first oligomeric compound having a region complementary to a target nucleic acid and a second oligomeric compound having a region complementary to the first oligomeric compound. In certain embodiments, the first oligomeric compound of a duplexed oligomeric compound comprises or consists of (1) a modified or unmodified oligonucleotide and optionally a conjugate group and (2) a second modified or unmodified oligonucleotide and optionally a conjugate group. Either or both oligomeric compounds of a duplexed oligomeric compound may comprise a conjugate group. The oligonucleotides of duplexed oligomeric compounds may include non-complementary overhanging nucleosides.

IV. Antisense Activity

In certain embodiments, oligomeric compounds are capable of hybridizing to a target nucleic acid, resulting in at least one antisense activity. In certain embodiments, oligomeric compounds selectively affect one or more target nucleic acid. Such selective oligomeric compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an oligomeric compound to a target nucleic acid results in recruitment of a protein that cleaves the target nucleic acid. For example, certain oligomeric compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are oligomeric compounds that are sufficiently "DNA-like" to elicit RNase H activity. In certain embodiments, one or more non-DNA-like nucleoside in the gap of a gapmer is tolerated.

In certain antisense activities, an oligomeric compound or a portion of an oligomeric compound is loaded into an RNA-induced silencing complex (RISC), ultimately resulting in cleavage of the target nucleic acid. For example, certain oligomeric compounds result in cleavage of the target nucleic acid by Argonaute. Oligomeric compounds that are loaded into RISC are RNAi compounds. RNAi compounds may be double-stranded (siRNA) or single-stranded (ssRNA).

In certain embodiments, hybridization of an oligomeric compound to a target nucleic acid does not result in recruitment of a protein that cleaves that target nucleic acid. In certain embodiments, hybridization of the oligomeric compound to the target nucleic acid results in alteration of splicing of the target nucleic acid. In certain embodiments, hybridization of an oligomeric compound to a target nucleic acid results in inhibition of a binding interaction between the target nucleic acid and a protein or other nucleic acid. In certain embodiments, hybridization of an oligomeric compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, oligonucleotides described herein are complementary to a target nucleic acid comprising a single-nucleotide polymorphism (SNP). In certain such embodiments, the oligonucleotide is capable of modulating expression of one allele of the SNP-containing target nucleic acid to a greater or lesser extent than it modulates another allele. In certain embodiments, an oligonucleotide hybridizes to a (SNP)-containing target nucleic acid at the single-nucleotide polymorphism site.

In certain embodiments, oligonucleotides are at least partially complementary to more than one target nucleic acid. For example, oligonucleotides described herein may mimic microRNAs, which typically bind to multiple targets.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligomeric compounds comprise oligonucleotides that are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligomeric compound comprising an oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. LRRK2

In certain embodiments, oligomeric compounds comprise or consist of any oligonucleotide comprising a region that is complementary to a target nucleic acid, wherein the target nucleic acid is LRRK2. In certain embodiments, LRRK2 nucleic acid has the sequence set forth in GENBANK Accession No: NT_029419.11 truncated from nucleotides 2759000 to U.S. Pat. No. 2,909,000 (incorporated herein as SEQ ID NO: 2) and GENBANK Accession No: NM_198578.3 (incorporated herein as SEQ ID NO: 3).

In certain embodiments, contacting a cell with an oligonucleotide complementary to SEQ ID NO: 2 or SEQ ID NO: 3 reduces the amount of LRRK2 mRNA, and optionally reduces the amount of LRRK2 protein. In certain embodiments, contacting a cell with an oligomeric compound complementary to SEQ ID NO: 2 or SEQ ID NO: 3 ameliroates one or more symptoms of Parkinson's disease. In certain embodiments, the symptom is loss of motor function, aggregate formation, and neuron death. In certain embodiments, contacting a cell with an oligonucleotide complementary to SEQ ID NO: 2 or SEQ ID NO: 3 improves motor function, reduces aggregate formation, and or preserves neurons.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in CNS tissue, including brain tissue, such as substantia nigra.

VI. Certain Pharmaceutical Compositions

In certain embodiments, described herein are pharmaceutical compositions comprising one or more oligomeric compound or a salt thereof. In certain embodiments, the pharmaceutical composition comprises a pharmaceutically acceptable diluent or carrier. In certain embodiments, a pharmaceutical composition comprises a sterile saline solution and one or more oligomeric compound. In certain embodiments, a pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS.

In certain embodiments, pharmaceutical compositions comprise one or more or oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300.

The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal, intracerebroventricular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or f such as for sugar anomers, or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated. Unless otherwise indicated, compounds described herein are intended to include corresponding salt forms.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: In Vitro Inhibition of Murine LRRK2 mRNA

Modified oligonucleotides targeted to a murine Leucine-Rich Repeat Kinase 2 (LRRK2) nucleic acid were tested for their effects on LRRK2 mRNA in vitro. bEND cells cultured at a density of 4,000 cells per well were transfected using Cytofectin reagent with 70 nM modified oligonucleotide. After a treatment period of approximately 24 hours, RNA was isolated from the cells and mouse LRRK2 mRNA levels were measured by quantitative real-time PCR using the murine primer probe set RTS3043 (forward sequence GGCGAGTTATCCGCACCAT, designated herein as SEQ ID NO: 11; reverse sequence CCAAAACCAGCATGACATTCTTAA, designated herein as SEQ ID NO: 12; probe sequence TGAGAGCCATGGCCACAGCACAA, designated herein as SEQ ID NO: 13). LRRK2 mRNA levels were adjusted according to total RNA content, as measured by RIBOGREEN. Results are shown in the table below as percent inhibition of LRRK2, relative to untreated control cells.

The oligonucleotides in the table below are 5-10-5 MOE gapmers. The gapmers are 20 nucleotides in length, wherein the central gap segment has ten 2'-deoxynucleosides and is flanked on both sides (in the 5' and 3' directions) by wings with five 2'-MOE modified nucleosides each. The internucleoside linkages throughout each gapmer are phosphorothioate (P=S) linkages. All cytosine residues throughout each gapmer are 5-methylcytosines. The modified oligonucleotides listed in the table below are 100% complementary to the target, mouse LRRK2 mRNA (GENBANK Accession No. NM_025730.3), incorporated herein as SEQ ID NO: 1. "Mouse target start site" indicates the 5'-most nucleoside of SEQ ID NO: 1 to which the gapmer is complementary. "Mouse target stop site" indicates the 3'-most nucleoside of SEQ ID NO: 1 to which the gapmer is complementary.

TABLE 1

Inhibition of mouse LRRK2 mRNA levels by gapmer modified oligonucleotides

| Oligo ID | Start Site | Stop Site | Sequence | % inhibition | SEQ ID NO |
|---|---|---|---|---|---|
| 422427 | 451 | 470 | AGTCCAACTATTGACAGGTT | 62 | 14 |
| 422439 | 2043 | 2062 | AGTGCACTAGCAGCTTGGAG | 63 | 15 |
| 422445 | 3070 | 3089 | TCCAGGTGGCTACTGAGGCA | 61 | 16 |
| 422467 | 5625 | 5644 | CAGCCAAGATCAAGTCCGGA | 61 | 17 |
| 422484 | 7166 | 7185 | CCACACCTCTACGACAGGGC | 64 | 18 |

Example 2: In Vivo Reduction of LRRK2 in Mice

Modified oligonucleotides complementary to mouse LRRK2 mRNA, shown in the table below, were synthesized and tested for their ability to modulate LRRK2 transcript levels in vivo. The oligonucleotides are 5-10-5 MOE gapmers. The gapmers are 20 nucleotides in length, wherein the central gap segment has ten 2'-deoxynucleosides and is flanked on both sides (in the 5' and 3' directions) by wings with five 2'-MOE modified nucleosides each. Each internucleoside linkage throughout each gapmer is either a phosphorothioate (P=S) linkage or a phosphorothioate (P=O) linkage. All cytosine residues throughout each gapmer are 5-methylcytosines. The oligonucleotides are 100% complementary to the target, mouse LRRK2 mRNA, SEQ ID NO: 1.

To test the ability of the oligonucleotides to inhibit LRRK2 mRNA expression in vivo, wild type Black 6 mice received a single 700 μg intracerebroventricular (ICV) injection of an oligonucleotide listed in the table below or PBS vehicle alone. Each treatment group consisted of four mice. Eight weeks after the single ICV injection, the mice were euthanized and RNA was isolated from the midbrain. RT-qPCR was performed as described in Example 1. The average results for each treatment group are presented in Table 2 below as percent inhibition of mouse LRRK2 mRNA expression, relative to the mouse LRRK2 mRNA levels in PBS treated animals.

TABLE 2

Reduction of LRRK2 with modified oligonucleotides in vivo

| Oligo ID | Inhibition of mouse LRRK2 mRNA (% PBS) |
|---|---|
| ASO A | 51.3 |
| ASO B | 70.1 |
| ASO C | 50.3 |

Example 3: Dose Dependent Reduction of LRRK2 In Vivo

The oligonucleotides listed in Example 2 were tested for dose responsive inhibition of mouse LRRK2 in wild type mice. Black 6 mice received a single ICV injection of an oligonucleotide at a dosage listed in the table below or PBS vehicle alone. Each treatment group consisted of three mice. Two weeks after the single ICV injection, the mice were euthanized and RNA was isolated from the midbrain. RT-qPCR was performed as described in Example 1. The average results for each treatment group are presented in the table below as percent inhibition of mouse LRRK2 mRNA expression, relative to the mouse LRRK2 mRNA levels in PBS treated animals. An inhibition value of 0% indicates that the average level of mouse LRRK2 mRNA in the treatment group was equal to or greater than the average level of mouse LRRK2 mRNA in the PBS treated group.

TABLE 4

Reduction of LRRK2 with modified oligonucleotides in vivo

| Oligo ID | Dose (μg) | Inhibition of mouse LRRK2 mRNA (% PBS) |
|---|---|---|
| ASO A | 10 | 1.0 |
|  | 30 | 12.3 |
|  | 100 | 23.3 |
|  | 300 | 53.7 |
|  | 700 | 59.1 |
| ASO B | 10 | 0 |
|  | 30 | 0.6 |
|  | 100 | 36.6 |
|  | 300 | 52.4 |
|  | 700 | 65.7 |
| ASO C | 10 | 11.7 |
|  | 30 | 0 |
|  | 100 | 31.2 |
|  | 300 | 48.2 |
|  | 700 | 49.1 |

Example 4: Prophylactic Reduction of LRRK2 with Modified Oligonucleotides in PFF Model Wild type mice received a single ICV injection of 700 μg of an oligonucleotide listed in the table below or PBS vehicle alone. Each treatment group consisted of eleven or twelve mice. Two weeks after oligonucleotide treatment, preformed fibrils (PFFs) of α-synuclein were injected into the striatum, resulting in formation of α-synuclein aggregates in several brain regions and motor deficits, as described (see Luk et al., Science, 2012, 338, 949-953). One control group did not receive injection of PFFs. Fifty-five days after the oligonucleotide treatment, motor function was tested in a wire hang test. The results are presented in Table 5 below as the average length of time the mice of each treatment group remained on the wire.

One day after the wire hang test, all of the mice in each treatment group were sacrificed except for the group that received no oligonucleotide and no PFF injection; only four mice in that group were sacrificed. Animals were perfused with ice-cold PBS. Ipsilateral hemispheres were fixed and processed for immunochemistry. Contralateral midbrain and striatum were dissected and frozen until RNA analysis, while entire contralateral cortex was dissected and frozen until protein analysis. LRRK2 mRNA expression was analyzed by RT-qPCR as described in the examples above, and the results are shown in Table 5 below as average percent inhibition relative to the wild type control group that received neither oligonucleotide treatment nor PFF injection.

LRRK2, α-synuclein, and hyperphosphorylated α-synuclein (p-α-syn) protein levels in the cortex were analyzed by western blot. Contralateral cortex tissue was first homogenized in RIPA buffer and centrifuged at 13,300×g. The supernatant was subjected to western blot for LRRK2 protein level, and 0-tubulin was used as a loading control. The results indicated that LRRK2 protein levels in the cortex were significantly lower in the oligonucleotide treated animals than in the animals that did not receive oligonucleotide treatment. The pellet was resuspended in RIPA buffer, centrifuged at 100,000×g, and the resulting insoluble material was further suspended in 2% SDS buffer, followed by an additional 100,000×g spin. The resulting supernatant was analyzed by western blot for α-synuclein and p-α-syn. The results showed that PFF injection resulted in recruitment of endogenous mouse α-synuclein into insoluble aggregates, as reported in Luk et al. The aggregates were also hyperphosphorylated. Oligonucleotide treatments reduced formation of the aggregates, as evidenced by a reduction of insoluble mouse α-synuclein and p-α-syn in the western blots. p-α-syn aggregates in the substantia nigra were visualized by immunohistochemistry. The average number of aggregates observed for samples of equal size from each treatment group is shown in Table 5 below. One-way ANOVA test of the results showed that the differences between the PBS treated and oligonucleotide treated animals were significant.

TABLE 5

Prophylactic treatment of PFF mice with LRKK2 modified oligonucleotides

| ISIS No. | PFF injected | Time in wirehang test (sec) | Inhibition of LRRK2 mRNA (%) Midbrain | Striatum | No. of p-α-syn aggregates |
|---|---|---|---|---|---|
| PBS | No | 193 | 0 | 4.0 | 0 |
| PBS | Yes | 94 | 0 | 0 | 42 |
| ASO A | Yes | 187 | 52.0 | 49.0 | 12 |
| ASO B | Yes | 175 | 43.0 | 24.8 | 21 |

Example 5: Reduction of LRRK2 with Modified Oligonucleotide in PFF Model

The effects of oligonucleotide reduction in wild type mice after the injection of PFFs was evaluated using ASO B (see Example 2). Mice were treated as described in Example 4 except that oligonucleotide treatment occurred two weeks after PFF injection instead of two weeks before PFF injection. Each treatment group consisted of ten animals. Fifty-five days after PFF injection, the mice were assessed in a wire hang test, as described in Example 4. One day after the wire hang test, the mice were sacrificed, the midbrain, striatum, and substantia nigra were collected, and LRRK2 mRNA and p-α-syn aggregates were measured, as described in Example 4. The results are shown in the table below as the averages for each treatment group. An entry of "nd" indicates that data was not collected for that treatment group. The results show that even when the modified oligonucleotide was administered after the onset of the PFF model, motor function was improved and the number of pathological aggregates was reduced.

TABLE 6

Treatment of PFF mice with LRKK2 modified oligonucleotides

| Oligo ID | PFF injected | Time in wirehang test (sec) | Inhibition of LRRK2 mRNA (%) Midbrain | Striatum | No. of p-α-syn aggregates |
|---|---|---|---|---|---|
| PBS | No | 227 | 0 | 0 | nd |
| PBS | Yes | 58 | 0 | 0 | 49 |
| ASO B | Yes | 141 | 62.3 | 43.6 | 38 |

Example 6. Prophylactic Reduction of LRRK2 with Modified Oligonucleotides in PFF Model in a Long Term Study Modified oligonucleotides were tested in a long term study to determine if long term treatment with modified oligonucleotides is protective of dopaminergic neurons. Accumulation of α-syn aggregates in the substantia nigra pars *compacta* compromises survival of dopaminergic neurons over time (Luk 2012, Tran 2014).

The effects of oligonucleotide reduction in wild type mice after the injection of PFFs was evaluated using ASO B (see Example 2) or control oligonucleotide 676630, a 5-10-5 MOE gapmer with mixed phosphodiester and phosphorothioate backbone with no known target. Mice were treated as described in Example 4 except mice received a second ICV dose of ASO B at 90 days, and were sacrificed at 180 days post first ICV treatment. Each treatment group consisted of 12 animals. At sacrifice, midbrain, striatum, and substantia nigra were collected, and LRRK2 mRNA and p-α-syn aggregates were measured, as described in Example 4, and dopaminergic cells were quantified by immunohistochemistry using anti-tyrosine hydroxylase (TH) antibody. The results are shown in the table below as the averages for each treatment group. The results show that in the group treated with modified oligonucleotide complementary to LRRK2, the number of pathological aggregates was reduced over a long treatment course. Additionally, quantification of TH-positive neurons showed that ASO B-mediated LRRK2 suppression rescued TH-positive cells in the ipsilateral substantia nigra pars *compacta* as compared to control treated mice.

TABLE 7

Prophylactic treatment of PFF mice with LRKK2 modified oligonucleotides in long term study

| Oligo ID | PFF injected | Inhibition of LRRK2 mRNA (%) Midbrain | Striatum | No. of p-α-syn aggregates | No. of dopaminergic cells |
|---|---|---|---|---|---|
| 676630 | Yes | 0 | 0 | 160 | 5880 |
| ASO B | Yes | 61.7 | 0 | 48 | 7522 |

Example 7. Effect of Central Delivery of LRRK2 Modified Oligonucleotides on Kidney and Lung LRRK2 Levels Prior studies have shown that genetic ablation of LRRK2 resulted in accumulation of autophagic vacuoles in kidney's proximal tubule epithelial cells and lung's type II pneumocytes. See, e.g., Herzig, M. C., et al., LRRK2 protein levels are determined by kinase function and are crucial for kidney and lung homeostasis in mice. Hum Mol Genet, 2011. 20(21): p. 4209-23; Hinkle, K. M., et al., LRRK2 knockout mice have an intact dopaminergic system but display alterations in exploratory and motor co-ordination behaviors. Mol Neurodegener, 2012. 7: p. 25; Tong, Y., et al., Loss of leucine-rich repeat kinase 2 causes age-dependent bi-phasic alterations of the autophagy pathway. Mol Neurodegener, 2012. 7: p. 2. Therefore, the effect of LRRK2 modified oligonucleotides administered to the central nervous systems by intracerebroventricular administration on LRRK2 levels in the kidney and lung was measured.

Wildtype C57BL/6J mice were treated with 700 μg modified oligonucleotides or PBS via intracerebroventricular administration. Tissues were harvested 56 days later. LRRK2 mRNA was measured by RT-QPCR in the cortex, midbrain, and kidney and lungs of the mice to determine if central delivery of modified oligonucleotides is specific to reducing LRRK2 in the CNS. While ASO A and ASO B significantly reduced LRRK2 mRNA in the midbrain and cortex, neither ASO A nor ASO B affected LRRK2 mRNA in the kidney or lung when injected intracerebroventricularly. Furthermore, hematoxylin and eosin histology revealed no abnormalities, i.e. vacuoles in the kidney and lungs. Therefore, central delivery of ASO A and ASO B specifically targets LRRK2 in the brain without affecting systemic LRRK2 levels or causing histological abnormalities in the periphery including kidney and lungs.

TABLE 8

LRRK2 mRNA levels in cortex, midbrain, kidney, and lung compared to PBS administration after intracerebroventricular administration

| Oligo ID | Inhibition of LRRK2 mRNA (%) | | | |
|---|---|---|---|---|
| | Cortex | Midbrain | Kidney | Lung |
| ASO A | 49.5 | 51.7 | 6.8 | 13.4 |
| ASO B | 60.4 | 70.5 | 19.2 | 6.8 |

The invention claimed is:

1. A method comprising administering to an animal having Parkinson's disease an oligomeric compound comprising a modified oligonucleotide, wherein the animal has a causative LRRK2 genetic mutation for Parkinson's disease, and wherein the modified oligonucleotide:
   a) consists of 12 to 30 linked nucleosides;
   b) has a nucleobase sequence that is at least 90% complementary to the nucleobase sequence of SEQ ID NO: 2 or SEQ ID NO: 3; and
   c) comprises at least one modified nucleoside comprising a modified sugar moiety and/or at least one modified internucleoside linkage,
wherein the administering results in amelioration of a symptom of Parkinson's disease,
wherein the symptom is aggregate formation or reduced motor function.

2. A method comprising identifying an animal having Parkinson's disease wherein the animal has a causative LRRK2 genetic mutation for Parkinson's disease, and administering to the animal an oligomeric compound comprising a modified oligonucleotide, wherein the modified oligonucleotide:
   a) consists of 12 to 30 linked nucleosides;
   b) has a nucleobase sequence that is at least 90% complementary to the nucleobase sequence of SEQ ID NO: 2 or SEQ ID NO: 3; and
   c) comprises at least one modified nucleoside comprising a modified sugar moiety and/or at least one modified internucleoside linkage,
wherein the administering results in amelioration of a symptom of Parkinson's disease,
wherein the symptom is aggregate formation or reduced motor function.

3. The method of claim 1, wherein the modified oligonucleotide has a nucleobase sequence that is 100% complementary to LRRK2.

4. The method of claim 1, wherein the administering results in improved motor function.

5. The method of claim 1, wherein the administering results in reduced aggregate formation.

6. The method of claim 1, wherein the oligomeric compound is administered prior to the detection of the symptom.

7. The method of claim 1, wherein the amelioration is the slowing of progression of the symptom, the delay of onset of the symptom, or the reduction in severity or frequency of the symptom.

8. The method of claim 1, wherein expression of LRRK2 mRNA and/or LRRK2 protein is reduced in the animal.

9. The method of claim 1, wherein the animal is a human.

10. The method of claim 1, wherein the oligomeric compound is single-stranded.

11. The method of claim 1, wherein the modified oligonucleotide comprises at least one modified nucleoside comprising a modified sugar moiety.

12. The method of claim 11, wherein the at least one modified nucleoside comprises a bicyclic sugar moiety.

13. The method of claim 12, wherein the bicyclic sugar moiety has a 2'-4' bridge, wherein the 2'-4' bridge is selected from —O—CH$_2$—; —O—CH$_2$—CH$_2$—; and —O—CH(CH$_3$)—.

14. The method of claim 1, wherein the modified oligonucleotide comprises at least one modified nucleoside comprising a modified non-bicyclic sugar moiety.

15. The method of claim 14, wherein the modified non-bicyclic sugar moiety comprises 2'-O-methoxyethyl (2'-MOE) or 2'-OMe.

16. The method of claim 1, wherein the at least one modified nucleoside comprises a sugar surrogate.

17. The method of claim 1, wherein the modified oligonucleotide has a sugar motif comprising:
   a 5'-region consisting of 1-5 linked 5'-region nucleosides;
   a central region consisting of 6-10 linked central region nucleosides; and
   a 3'-region consisting of 1-5 linked 3'-region nucleosides,
wherein each of the 5'-region nucleosides and each of the 3'-region nucleosides comprises a modified sugar moiety and each of the central region nucleosides comprises an unmodified DNA sugar moiety.

18. The method of claim 1, wherein the modified oligonucleotide comprises at least one modified internucleoside linkage, wherein at least one modified internucleoside linkage is a phosphorothioate internucleoside linkage.

19. The method of claim 1, wherein each internucleoside linkage of the modified oligonucleotide is either an unmodified phosphodiester internucleoside linkage or a phosphorothioate internucleoside linkage.

20. The method of claim 1, wherein the modified oligonucleotide comprises at least one modified nucleobase, wherein the modified nucleobase is a 5-methylcytosine.

21. The method of claim 1, wherein the oligomeric compound comprises a conjugate group.

22. The method of claim 1, wherein the oligomeric compound is paired with a second oligomeric compound to form a duplex.

23. The method of claim 1, wherein the administering is intrathecal administration or intracerebroventricular administration.

24. The method of claim 1, wherein the administering does not cause toxicity in the periphery.

25. The method of claim 1, wherein the symptom is reduced motor function.

* * * * *